United States Patent [19]

Hiraoka et al.

[11] 4,377,591
[45] Mar. 22, 1983

[54] 7-OXO-1-AZABICYCLO[3.2.0]HEPT-2-ENE-2-CARBOXYLIC ACID DERIVATIVES, THEIR USE AND PREPARATION

[75] Inventors: Tetsuo Hiraoka; Takeo Kobayashi; Noboru Ishida; Shinichi Sugawara, all of Hiromachi, Japan

[73] Assignee: Sankyo Company, Limited, Tokyo, Japan

[21] Appl. No.: 239,139

[22] Filed: Feb. 27, 1981

[30] Foreign Application Priority Data

Mar. 3, 1980 [JP] Japan .................................. 55-26254

[51] Int. Cl.$^3$ .................... C07D 487/04; A61K 31/40
[52] U.S. Cl. ............................. 424/274; 260/245.2 T; 260/239 A
[58] Field of Search .................. 260/245.2 T; 424/274

[56] References Cited

U.S. PATENT DOCUMENTS

| | | | |
|---|---|---|---|
| 4,203,902 | 5/1980 | Shih .............................. | 260/245.2 T |
| 4,218,459 | 8/1980 | Cama et al. .................... | 260/245.2 T |
| 4,260,627 | 4/1981 | Christensen et al. ......... | 260/245.2 T |
| 4,262,009 | 4/1981 | Christensen et al. ......... | 260/245.2 T |
| 4,267,188 | 5/1981 | Cama et al. .................... | 260/245.2 T |

Primary Examiner—Mary C. Lee
Attorney, Agent, or Firm—Frishauf, Holtz, Goodman & Woodward

[57] ABSTRACT

7-Oxo-1-azabicyclo[3.2.0]hept-2-ene-2-carboxylic acid derivatives of formula (I):

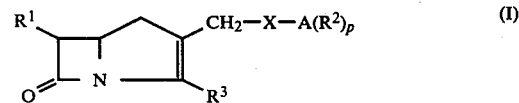

(in which:)
$R^1$ represents a hydrogen atom or an optionally substituted alkyl group;
X represents an oxy group, a thio group, a sulphinyl group or a sulphonyl group;
A represents a bivalent or trivalent saturated aliphatic hydrocarbon group;
p is 1 (when A is bivalent) or 2 (when A is trivalent);
$R^2$ represents an azido, nitro or cyano group or one of the groups of formula

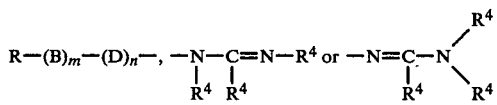

m and n are the same or different and each is 0 or 1;
R represents an amidino group or a group of formula $R^4$, —N($R^4$)$_2$ or —Y$R^4$,
B represents a group of formula

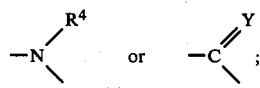

D represents a group of formula

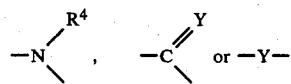

(provided that, where m and n are both 1, the groups represented by B and D must be different);
$R^4$ represents a hydrogen atom or an alkyl group and, where there are 2 or more groups represented by $R^4$, they may be the same or different; and
Y represents an oxygen atom or a sulphur atom; and
$R^3$ represents a carboxy group or a protected carboxy group)
and pharmaceutically acceptable salts thereof are valuable antibiotics and may be prepared by a process which includes heating a corresponding phosphorus-ylide compound.

14 Claims, No Drawings

7-OXO-1-AZABICYCLO[3.2.0]HEPT-2-ENE-2-CARBOXYLIC ACID DERIVATIVES, THEIR USE AND PREPARATION

BACKGROUND TO THE INVENTION

The present invention relates to a series of new 7-oxo-1-azabicyclo[3.2.0]hept-2-ene-2-carboxylic acid derivatives, to their use as antibiotics and to their preparation.

The compounds of the invention possess the following basic structure, in which the numbering shown is that used hereinafter to define the compounds:

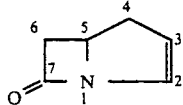

It will be seen that this structure is similar to the structure of certain penicillin derivatives, specifically the 2-penem derivatives, which possess the following basic structure:

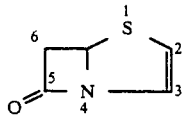

except that the sulphur atom of the 2-penem compounds has been replaced by a carbon atom and, indeed, the compounds of the invention could be called "1-carba-2-penem-3-carboxylic acid derivatives" (using the 2-penem numbering system).

A natural antibiotic having the 7-oxo-1-azabicyclo[3.2.0]hept-2-ene structure has been isolated and has been found to have extraordinarily potent antibacterial activity, as described in Japanese Patent Application Kokai (i.e. as laid-open to public inspection) No. 73191/76. This natural antibiotic is called "thienamycin" and has been found to be (5R,6S)-3-(2-aminoethylthio)-6-[1-(R)-hydroxyethyl]-7-oxo-1-azabicyclo[3.2.0]hept-2-ene-2-carboxylic acid, i.e.:

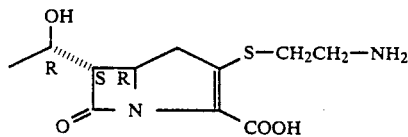

However, compounds of the thienamycin type have been found to be unstable, as described in The Journal of Antibiotics, 32, 1 (1979) and it would, therefore, be desirable to discover compounds which, whilst retaining the antibiotic activity of thienamycin, have greater chemical stability.

BRIEF SUMMARY OF INVENTION

We have now discovered a series of 7-oxo-1-azabicyclo[3.2.0]hept-2-ene-2-carboxylic acid derivatives which, like thienamycin, are potent antibiotics, but which are significantly more stable than is thienamycin.

The compounds of the invention have the general formula (I):

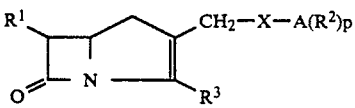

in which:

$R^1$ represents a hydrogen atom, an alkyl group or an alkyl group having one or more hydroxy, lower alkoxy, lower alkanoyloxy, amino, lower alkyl-substituted amino, lower alkanoylamino, mercapto or lower alkylthio substituents;

X represents an oxy group, a thio group, a sulphinyl group or a sulphonyl group;

A represents a bivalent or trivalent saturated aliphatic hydrocarbon group;

P is 1 (when A is bivalent) or 2 (when A is trivalent);

$R^2$ represents an azido, nitro or cyano group or one of the groups of formula

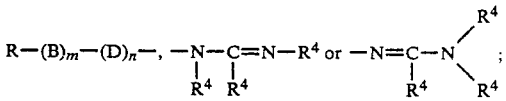

(in which:

m and n are the same or different and each is 0 or 1;

R represents an amidino group or a group of formula $R^4$, $-N(R^4)_2$ or $-YR^4$;

B represents a group of formula

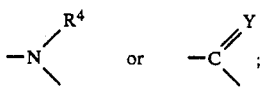

D represents a group of formula

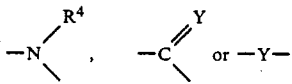

(provided that, where m and n are both 1, the groups represented by B and D are different);

$R^4$ represents a hydrogen atom or an alkyl group and, if there are two or more groups represented by $R^4$, they may be the same or different; and Y represents an oxygen atom or a sulphur atom); and $R^3$ represents a carboxy group or a protected carboxy group capable of conversion to a carboxy group under physiological conditions.

In those compounds of formula (I) where $R^3$ represents a carboxy group and/or where $R^2$ includes a carboxy group, the compounds are able to form salts and the invention thus also provides pharmaceutically acceptable salts of these compounds.

The invention still further provides a process for preparing compounds of formula (I) and their pharmaceutically acceptable salts, which process comprises:

(a) heating a phosphorus-ylide compound of formula (II):

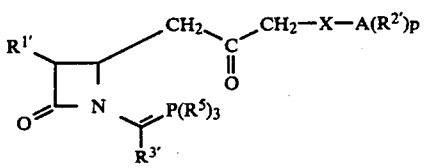

[in which:

R[1]' represents a hydrogen atom, an alkyl group or an alkyl group having one or more hydroxy, protected hydroxy, alkoxy, protected amino, lower alkyl-substituted; amino, protected mercapto or lower alkylthio substituents, R[2]' represents any of the groups represented by R[2] other than

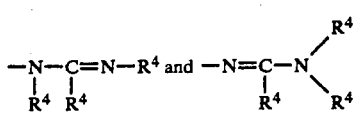

and where any reactive amino, hydroxy, mercapto or carboxy groups have been protected;

R[3]' represents a protected carboxy group;

R[5] represents an alkyl group or an aryl group; and X, A and p are as defined above)

to give a compound of formula (III):

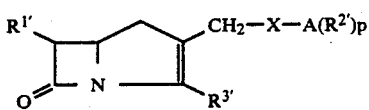

(in which R[1]', R[2]', R[3]', X, A and p are as defined above);

(b) if necessary, deprotecting any protected amino, hydroxy, mercapto or carboxy group;

(c) if desired, converting any free amino group in R[2] to a group of formula

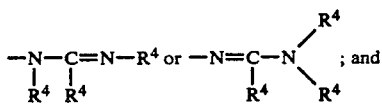

(d) where the resulting compound contains a carboxy group, if desired salifying the compound to produce a pharmaceutically acceptable salt thereof.

The invention still further provides a pharmaceutical composition comprising an antibiotic and a pharmaceutically acceptable carrier or diluent, wherein the antibiotic is a compound of formula (I) or a pharmaceutically acceptable salt thereof.

DETAILED DESCRIPTION OF INVENTION

In the compounds of formula (I), where R[1] represents an alkyl group, it may be a straight or branched alkyl group and preferably has from 1 to 5 carbon atoms. Examples of such groups include the methyl, ethyl, propyl, isopropyl, butyl, isobutyl, sec-butyl, pentyl and isopentyl groups.

Where R[1] represents an alkyl group having an alkoxy substitutent, this is preferably a lower alkoxy substituent, for example a methoxy, ethoxy, propoxy or isopropoxy group. Examples of suitable alkyl groups are those given above.

Where R[1] represents an alkanoyloxy-substituted alkyl group, the alkanoyloxy group is preferably a lower alkanoyloxy group, for example a formyloxy, acetoxy, propionyloxy, butyryloxy or isobutyryloxy group, and the alkyl group is preferably any one of those listed above.

Where R[1] represents an amino-substituted alkyl group, the alkyl group may be any one of those listed above. The amino group may be unsubstituted or it may have one or two alkyl substituents, preferably lower alkyl substituents. Suitable such alkyl-substituted amino groups include methylamino, dimethylamino, ethylamino, diethylamino, propylamino and isopropylamino groups. The amino group of the amino-substituted alkyl group represented by R[1] may also be substituted by an alkanoyl group, which is preferably a lower alkanoyl group, and suitable such alkanoylamino groups include formylamino, acetylamino, propionylamino, butyrylamino and isobutyrylamino groups.

Where R[1] represents a mercapto-substituted or alkylthio-substituted alkyl group, the alkyl group may be any one of those listed above, whilst the alkylthio substituent is preferably a lower alkylthio group, for example a methylthio, ethylthio, propylthio or isopropylthio group.

A represents a bivalent or trivalent saturated aliphatic hydrocarbon group, which can be a straight or branched chain group. Where A represents a bivalent group, this may be an alkylene or alkylidene group and is preferably a C$_1$–C$_4$ alkylene or alkylidene group, for example a methylene, ethylene, trimethylene, propylene, tetramethylene, ethylidene or propylidene group. Where A represents a trivalent saturated aliphatic hydrocarbon group, it is preferably an alkane-α-yl-ω-ylidene group and is more preferably such a group having from 2 to 5 carbon atoms.

Where R[2] represents a group of formula

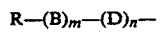

and m and n are both 0, R[2]=R and R represents a hydrogen atom, an alkyl group, an amino group, a mono- or di-alkylamino group, a hydroxy group, a mercapto group, an alkoxy group, an alkylthio group or an amidino group. In this case, R is preferably a hydrogen atom, an amino group, a mono- or di-alkylamino group, a hydroxy group, a mercapto group, an alkoxy group or an alkylthio group. Preferred mono- and di-alkylamino groups which may be represented by R and hence by R[2] are such groups where the alkyl group is a lower alkyl group, for example the methylamino, dimethylamino, ethylamino, diethylamino, propylamino and isopropylamino groups. Where R, and hence R[2], represents an alkoxy group, this is preferably a lower alkoxy group, for example a methoxy, ethoxy, propoxy or isopropoxy group. Where R, and hence R[2] represents an alkylthio group, this is preferably a lower alkylthio group, for example a methylthio, ethylthio, propylthio or isopropylthio group.

Where m is 0 and n is 1, R[2] represents a group of formula R—D— and is preferably a hydrazino, alkyl-substituted hydrazino, hydroxyamino, alkoxyamino, aminooxy, alkyl-substituted aminooxy, aminothio, alkyl-substituted aminothio, carboxy, alkoxycarbonyl, thiocarboxy, (alkylthio)carbonyl, carbamoyl or alkyl-substituted carbamoyl group.

Where R² represents an alkyl-substituted hydrazino group, there may be one or more (preferably 2) alkyl substitutents and these are preferably lower alkyl groups. Examples of suitable alkyl-substituted hydrazino groups include the methylhydrazino, N,N-dimethylhydrazino, ethylhydrazino, N,N-diethylhydrazino, propylhydrazino and isopropylhydrazino groups.

Where R² represents an alkoxyamino group, the alkoxy group is preferably a lower alkoxy group and examples of suitable alkoxyamino groups include the methoxyamino, ethoxyamino, propoxyamino and isopropoxyamino groups.

Where R² represents an alkyl-substituted aminooxy group, there may be one or two alkyl substituents and these are preferably lower alkyl groups. Examples of suitable alkyl-substituted aminooxy groups include the methylaminooxy, dimethylaminooxy, ethylaminooxy, diethylaminooxy, propylaminooxy and isopropylaminooxy groups.

Where R² represents an alkyl-substituted aminothio group, there may be one or two alkyl substituents and these are preferably lower alkyl groups. Examples of suitable alkyl-substituted aminothio groups include the methylaminothio, dimethylaminothio, ethylaminothio, diethylaminothio, propylaminothio and isopropylaminothio groups.

Where R² represents an alkoxycarbonyl group, the alkoxy group is preferably a lower alkoxy group and examples of suitable alkoxycarbonyl groups include the methoxycarbonyl, ethoxycarbonyl, propoxycarbonyl and isopropoxycarbonyl groups.

Where R² represents an (alkylthio)carbonyl group, the alkyl group is preferably a lower alkyl group and examples of suitable (alkylthio)carbonyl groups include the (methylthio)carbonyl, (ethylthio)carbonyl, (propylthio)carbonyl and (isopropylthio)carbonyl groups.

Where R² represents an alkyl-substituted carbamoyl group, there may be 1 or 2 alkyl substituents, which are preferably lower alkyl groups. Examples of suitable alkyl-substituted carbamoyl groups include the methylcarbamoyl, dimethylcarbamoyl, ethylcarbamoyl, diethylcarbamoyl, propylcarbamoyl and isopropylcarbamoyl groups.

When m and n are both 1, R² represents a group of formula R—B—D—, in which B and O are different. Of the groups R² represented by this formula, the alkanoylamino, (thioalkanoyl)amino, ureido, thioureido, alkanoyloxy, carbamoyloxy, alkyl-substituted carbamoyloxy, thiocarbamoyloxy, alkyl-substituted thiocarbamoyloxy, alkoxycarbonyloxy, (alkylthio)carbonyloxy, alkylthio(thiocarbonyl)oxy, alkanoylthio, (thioalkanoyl)thio, thiocarbamoylthio, alkyl-substituted thiocarbamoylthio, carbamoylthio, alkyl-substituted carbamoylthio, alkoxy(thiocarbonyl)thio, alkylthio(thiocarbonyl)thio, carbazoyl, alkyl-substituted carbazoyl, guanidinocarbonyl, thiocarbazoyl and alkyl-substituted thiocarbazoyl groups are preferred.

Where R² represents an alkanoylamino group, the alkanoyl group is preferably a lower alkanoyl group and examples of suitable alkanoylamino groups include the formylamino, acetylamino, propionylamino, butyrylamino and isobutyrylamino groups.

Where R² represents a (thioalkanoyl)amino group, the thioalkanoyl group is preferably a lower thioalkanoyl group and examples of suitable such thioalkanoylamino groups include the thioacetylamino, thiopropionylamino, thiobutyrylamino and thioisobutyrylamino groups.

Where R² represents an alkanoyloxy group, the alkanoyl group is preferably a lower alkanoyl group and examples of suitable such alkanoyloxy groups include the formyloxy, acetoxy, propionyloxy, butyryloxy and isobutyryloxy groups.

Where R² represents an alkyl-substituted carbamoyloxy group, there may be 1 or 2 alkyl substituents which are preferably lower alkyl groups. Examples of suitable alkyl-substituted carbamoyloxy groups include the methylcarbamoyloxy, dimethylcarbamoyloxy, ethylcarbamoyloxy, diethylcarbamoyloxy, propylcarbamoyloxy and isopropylcarbamoyloxy groups.

Where R² represents an alkyl-substituted thiocarbamoyloxy group, there may be 1 or 2 alkyl substituents, which are preferably lower alkyl groups. Examples of such alkyl-substituted thiocarbamoyloxy groups include the methyl(thiocarbamoyl)oxy, dimethyl)thiocarbamoyl)oxy, ethyl)thiocarbamoyl)oxy and diethyl(thiocarbamoyl)oxy groups.

Where R² represents an alkoxycarbonyloxy group, the alkoxy group is preferably a lower alkoxy group and examples of such alkoxycarbonyloxy groups include the methoxycarbonyloxy, ethoxycarbonyloxy, propoxycarbonyloxy and isopropoxycarbonyloxy groups.

Where R² represents an (alkylthio)carbonyloxy group, the alkyl group is preferably a lower alkyl group and examples of such (alkylthio)carbonyloxy groups include the (methylthio)carbonyloxy, (ethylthio)carbonyloxy, (propylthio)carbonyloxy and (isopropylthio)carbonyloxy groups.

Where R² represents an alkylthio(thiocarbonyl)oxy group, the alkyl group is preferably a lower alkyl group and examples of such alkylthio(thiocarbonyl)oxy groups include the methylthio(thiocarbonyl)oxy, ethylthio(thiocarbonyl)oxy, propylthio(thiocarbonyl)oxy and isopropylthio(thiocarbonyl)oxy groups.

Where R² represents an alkanoylthio group, the alkanoyl group is preferably a lower alkanoyl group and examples of such alkanoylthio groups include the formylthio, acetylthio, propionylthio, butyrylthio and isobutyrylthio groups.

Where R² represents a thioalkanoylthio group, the alkanoyl group is preferably a lower alkanoyl group and examples of such thioalkanoylthio groups include the thioacetylthio, thiopropionylthio, thiobutyrylthio and thioisobutyrylthio groups.

Where R² represents an alkyl-substituted thiocarbamoylthio group, there may be 1 or 2 alkyl substituents, which are preferably lower alkyl groups. Examples of such alkyl-substituted thiocarbamoylthio groups include the methyl(thiocarbamoyl)thio, dimethyl(thiocarbamoyl)thio, ethyl(thiocarbamoyl)thio and diethyl(thiocarbamoyl)thio groups.

Where R² represents an alkyl-substituted carbamoylthio group, there may be 1 or 2 alkyl substituents, which are preferably lower alkyl groups. Examples of such alkyl-substituted carbamoylthio groups include the methylcarbamoylthio, dimethylcarbamoylthio, ethylcarbamoylthio and diethylcarbamoylthio groups.

Where R² represents an alkoxy(thiocarbonyl)thio group, the alkoxy group is preferably a lower alkoxy group and examples of such alkoxy(thiocarbonyl)thio groups include the methoxy(thiocarbonyl)thio, ethoxy(thiocarbonyl)thio, propoxy(thiocarbonyl)thio and isopropoxy(thiocarbonyl)thio groups.

Where $R^2$ represents an alkylthio(thiocarbonyl)thio group, the alkyl group is preferably a lower alkyl group and examples of such alkylthio(thiocarbonyl)thio groups include the methylthio(thiocarbonyl)thio, ethylthio(thiocarbonyl)thio, propylthio(thiocarbonyl)thio and isopropylthio(thiocarbonyl)thio groups.

Where $R^2$ represents an alkyl-substituted carbazoyl group, there may be 1 or more (preferably 1 or 2) alkyl substituents, which are preferably lower alkyl groups, and these are preferably on the 3-position of the carbazoyl group. Examples of such alkyl-substituted carbazoyl groups include the 3-methylcarbazoyl, 3,3-dimethylcarbazoyl, 3-ethylcarbazoyl, 3,3-diethylcarbazoyl, 3-propylcarbazoyl and 3-isopropylcarbazoyl groups.

Where $R^2$ represents an alkyl-substituted thiocarbazoyl group, there may be 1 or more (preferably 1 or 2) alkyl substituents, which are preferably lower alkyl groups, and these are preferably on the 3-position of the carbazoyl group. Examples of such alkyl-substituted thiocarbazoyl groups include the 3-methyl(thiocarbazoyl), 3,3-dimethyl(thiocarbazoyl), 3-ethyl(thiocarbazoyl), 3,3-diethyl(thiocarbazoyl), 3-propyl(thiocarbazoyl) and 3-isopropyl(thiocarbazoyl) groups.

Alternatively, $R^2$ may represent a group of formula

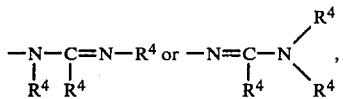

in which the groups represented by $R^4$, which may be the same or different, are hydrogen atoms or alkyl groups, preferably lower alkyl groups, such as the methyl, ethyl, propyl or isopropyl groups.

The above-mentioned groups are preferred when p is 1. Where p is 2, the two groups represented by $R^2$ are preferably on the ω-carbon atom of the hydrocarbon group A and one of the groups $R^2$ is preferably an amino group; the other group $R^2$ is preferably a carboxy group, an alkoxycarbonyl group (more preferably a lower alkoxycarbonyl group, such as a methoxycarbonyl, ethoxycarbonyl, propoxycarbonyl or isopropoxycarbonyl group), a thiocarboxy group, an (alkylthio)carbonyl group [more preferably a lower (alkylthio)carbonyl group, for example a (methylthio)carbonyl, (ethylthio)carbonyl, (propylthio)carbonyl or (isopropylthio)carbonyl group], a carbamoyl or alkyl-substituted carbamoyl group (in which the alkyl substituent or substituents are preferably lower alkyl groups, for example a methylcarbamoyl, dimethylcarbamoyl, ethylcarbamoyl, diethylcarbamoyl, propylcarbamoyl or isopropylcarbamoyl group), or a carbazoyl or alkyl-substituted carbazoyl group (in which the alkyl substituent or substituents are preferably lower alkyl groups and preferably at the 3-position of the carbazoyl group, for example a 3-methylcarbazoyl, 3,3-dimethylcarbazoyl, 3-ethylcarbazoyl, 3,3-diethylcarbazoyl, 3-propylcarbazoyl or 3-isopropylcarbazoyl group).

$R^3$ may represent a carboxy group or a protected carboxy group, which is capable of conversion under physiological conditions to a free carboxy group. Examples of suitable protected carboxy groups include the alkanoyloxymethoxycarbonyl groups (in which the alkanoyl group is preferably a lower alkanoyl group, for example the acetoxymethoxycarbonyl, propionyloxymethoxycarbonyl, butyryloxymethoxycarbonyl, isobutyryloxymethoxycarbonyl or pivaloyloxymethoxycarbonyl groups), a 1-alkoxycarbonyloxyethoxycarbonyl group (in which the alkoxy group is preferably a lower alkoxy group, for example a 1-methoxycarbonyloxyethoxycarbonyl, 1-ethoxycarbonyloxyethoxycarbonyl, 1-propoxycarbonyloxyethoxycarbonyl or 1-isopropoxycarbonyloxyethoxycarbonyl group) or a phthalidyloxycarbonyl group.

The more preferred compounds of formula (I) are those in which:

$R^1$ represents a hydrogen atom, a lower alkyl group or a substituted lower alkyl group in which the substituent is a hydroxy group, a lower alkanoyloxy group, an amino group, a lower alkyl-substituted amino or a lower alkanoylamino group;

X represents an oxy group, a thio group, a sulphinyl group or a sulphonyl group;

A represents a bivalent or trivalent saturated aliphatic hydrocarbon group;

p is 1 (when A is bivalent) or 2 (when A is trivalent);

when p is 1, $R^2$ represents a hydrogen atom, an amino group, a lower alkyl-substituted amino group, a hydrazino group, a lower alkyl-substituted hydrazino group, a lower alkanoylamino group, a ureido group, a hydroxyamino group, a lower alkoxyamino group, an azido group, a nitro group, a hydroxy group, a lower alkoxy group, a lower alkanoyloxy group, a carbamoyloxy group, a lower alkyl-substituted carbamoyloxy group, an aminooxy group, a lower alkyl-substituted aminooxy group, an aminothio group, a lower alkyl-substituted aminothio group, a carboxy group, a lower alkoxycarbonyl group, a cyano group, a thiocarboxy group, a lower alkyl-substituted thiocarbonyl group, a carbamoyl group, a lower alkyl-substituted carbamoyl group, a carbazoyl group, a lower alkyl-substituted carbazoyl group, a guanidinocarbonyl group, or a group of formula

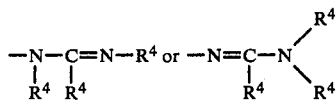

(in which the groups represented by $R^4$ may be the same or different and each is a hydrogen atom or a lower alkyl group); or when p is 2, one of the groups represented by $R^2$ is an amino group and the other is a carboxy group, a lower alkoxycarbonyl group, a carbamoyl group, a lower alkyl-substituted carbamoyl group, a carbazoyl group or a lower alkyl-substituted carbazoyl group having one or two substituents in the 3-position; and $R^3$ represents a carboxy group, a lower alkanoyloxymethoxycarbonyl group or a phthalidyloxycarbonyl group.

The term "lower alkyl" means alkyl having from 1 to 6 carbon atoms and other lower groups are to be construed accordingly.

The most preferred compounds of formula (I) are those in which:

$R^1$ represents a hydrogen atom, a hydroxymethyl group, a 1-hydroxyethyl group or a 1-hydroxy-1-methylethyl group;

X represents an oxy group, a thio group, a sulphinyl group or a sulphonyl group;

p is 1 or 2;

A represents a saturated aliphatic hydrocarbon group which, when p is 1, is bivalent and has from 1 to 4 carbon atoms or, when p is 2, is trivalent and has from 2 to 5 carbon atoms;

when p is 1, $R^2$ represents a hydrogen atom, an amino group, a hydrazino group, a ureido group, an azido group, a nitro group, a carbamoyl group, a carbazoyl group, a guanidinocarbonyl group, a formimidoylamino group or an acetimidoylamino group; or when p is 2, one of the groups represented by $R^2$ is an amino group and the other group is a carboxy group, a carbamoyl group or a carbazoyl group; and $R^3$ represents a carboxy group, a pivaloyloxymethoxycarbonyl group or a phthalidyloxycarbonyl group.

The compounds of formula (I) can exist in the form of various optical isomers and stereoisomers, due to the presence of asymmetric carbon atoms. Although all of the isomers are represented herein by a single formula, the present invention covers not only mixtures of the isomers but also the individual isomers. Preferred compounds are those in which the carbon atom at the 5-position of the azabicyclo[3.2.0]hept-2-ene system is in the same configuration as the corresponding carbon atom in the penicillins, that is to say the R-configuration.

The carboxylic acid compounds of formula (I) in which $R^3$ represents a carboxy group can be converted to pharmacologically acceptable salts, for example inorganic metal salts (such as the lithium, sodium, potassium or magnesium salts), the ammonium salts and organic amine salts (such as the cyclohexylammonium, diisopropylammonium and triethylammonium salts). Of these, the sodium and potassium salts are preferred.

Examples of compounds of formula (I) are listed below. Where appropriate, the compounds of the invention are hereafter identified by the numbers appended to them in the following list:

1. 3-(Aminomethylthiomethyl)-6-(1-hydroxyethyl)-7-oxo-1-azabicyclo[3.2.0]hept-2-ene-2-carboxylic acid.
2. 3-(Formimidoylaminomethylthiomethyl)-6-(1-hydroxyethyl)-7-oxo-1-azabicyclo[3.2.0]hept-2-ene-2-carboxylic acid.
3. 3-(Azidomethylthiomethyl)-6-(1-hydroxyethyl)-7-oxo-1-azabicyclo[3.2.0]hept-2-ene-2-carboxylic acid.
4. 6-(1-Hydroxyethyl)-7-oxo-3-(ureidomethylthiomethyl)-1-azabicyclo[3.2.0]hept-2-ene-2-carboxylic acid.
5. 3-(Aminooxymethylthiomethyl)-6-(1-hydroxyethyl)-7-oxo-1-azabicyclo[3.2.0]hept-2-ene-2-carboxylic acid.
6. 3-(Carbamoyloxymethylthiomethyl)-6-(1-hydroxyethyl)-7-oxo-1-azabicyclo[3.2.0]hept-2-ene-2-carboxylic acid.
7. 3-(Carbamoylmethylthiomethyl)-6-(1-hydroxyethyl)-7-oxo-1- 1-azabicyclo[3.2.0]hept-2-ene-2-carboxylic acid.
8. 3-(Carbazoylmethylthiomethyl)-6-(1-hydroxyethyl)-7-oxo-1-azabicyclo[3.2.0]hept-2-ene-2-carboxylic acid.
9. 3-(Aminothiomethylthiomethyl)-6-(1-hydroxyethyl)-7-oxo-1-azabicyclo[3.2.0]hept-2-ene-2-carboxylic acid.
10. 3-(2-Aminoethylthiomethyl)-6-(1-hydroxyethyl)-7-oxo-1-azabicyclo[3.2.0]hept-2-ene-2-carboxylic acid.
11. 3-(2-Formimidoylaminoethylthiomethyl)-6-(1-hydroxyethyl)-7-oxo-1-azabicyclo[3.2.0]hept-2-ene-2-carboxylic acid.
12. 3-(2-Azidoethylthiomethyl)-6-(1-hydroxyethyl)-7-oxo-1-azabicyclo[3.2.0]hept-2-ene-2-carboxylic acid.
13. 6-(1-Hydroxyethyl)-7-oxo-3-(2-ureidoethylthiomethyl)-1-azabicyclo[3.2.0]hept-2-ene-2-carboxylic acid.
14. 3-(2-Aminooxyethylthiomethyl)-6-(1-hydroxyethyl)-7-oxo-1-azabicyclo[3.2.0]hept-2-ene-2-carboxylic acid.
15. 3-(2-Carbamoyloxyethylthiomethyl)-6-(1-hydroxyethyl)-7-oxo-1-azabicyclo[3.2.0]hept-2-ene-2-carboxylic acid.
16. 3-(2-Carbamoylethylthiomethyl)-6-(1-hydroxyethyl)-7-oxo-1-azabicyclo[3.2.0]hept-2-ene-2-carboxylic acid.
17. 3-(2-Carbazoylethylthiomethyl)-6-(1-hydroxyethyl)-7-oxo-1-azabicyclo[3.2.0]hept-2-ene-2-carboxylic acid.
18. 3-(2-Aminothioethylthiomethyl)-6-(1-hydroxyethyl)-7-oxo-1-azabicyclo[3.2.0]hept-2-ene-2-carboxylic acid.
19. 3-(2-Amino-2-carboxyethyl)thiomethyl-6-(1-hydroxyethyl)-7-oxo-1-azabicyclo[3.2.0]hept-2-ene-2-carboxylic acid.
20. 3-(2-Amino-2-methoxycarbonylethyl)thiomethyl-6-(1-hydroxyethyl)-7-oxo-1-azabicyclo[3.2.0]hept-2-ene-2-carboxylic acid.
21. 3-(2-Amino-2-carbamoylethyl)thiomethyl-6-(1-hydroxyethyl)-7-oxo-1-azabicyclo[3.2.0]hept-2-ene-2-carboxylic acid.
22. 3-(2-Amino-2-carbazoylethyl)thiomethyl-6-(1-hydroxyethyl)-7-oxo-1-azabicyclo[3.2.0]hept-2-ene-2-carboxylic acid.
23. 3-(2-Amino-1-methylethyl)thiomethyl-6-(1-hydroxyethyl)-7-oxo-1-azabicyclo[3.2.0]hept-2-ene-2-carboxylic acid.
24. 3-(2-Formimidoylamino-1-methylethyl)thiomethyl-6-(1-hydroxyethyl)-7-oxo-1-azabicyclo[3.2.0]hept-2-ene-2-carboxylic acid.
25. 3-(2-Azido-1-methylethyl)thiomethyl-6-(1-hydroxyethyl)-7-oxo-1-azabicyclo[3.2.0]hept-2-ene-2-carboxylic acid.
26. 6-(1-Hydroxyethyl)-3-(1-methyl-2-ureidoethyl)thiomethyl-7-oxo-1-azabicyclo[3.2.0]hept-2-ene-2-carboxylic acid.
27. 3-(2-Aminooxy-1-methylethyl)thiomethyl-6-(1-hydroxyethyl)-7-oxo-1-azabicyclo[3.2.0]hept-2-ene-2-carboxylic acid.
28. 3-(2-Carbamoyloxy-1-methylethyl)thiomethyl-6-(1-hydroxyethyl)-7-oxo-1-azabicyclo[3.2.0]hept-2-ene-2-carboxylic acid.
29. 3-(2-Carbamoyl-1-methylethyl)thiomethyl-6-(1-hydroxyethyl)-7-oxo-1-azabicyclo[3.2.0]hept-2-ene-2-carboxylic acid.
30. 3-(2-Carbazoyl-1-methylethyl)thiomethyl-6-(1-hydroxyethyl)-7-oxo-1-azabicyclo[3.2.0]hept-2-ene-2-carboxylic acid.
31. 3-(2-Aminothio-1-methylethyl)thiomethyl-6-(1-hydroxyethyl)-7-oxo-1-azabicyclo[3.2.0]hept-2-ene-2-carboxylic acid.
32. 3-(2-Amino-2-carboxy-1-methylethyl)thiomethyl-6-(1-hydroxyethyl)-7-oxo-1-azabicyclo[3.2.0]hept-2-ene-2-carboxylic acid.
33. 3-(2-Amino-2-methoxycarbonyl-1-methylethyl)thiomethyl-6-(1-hydroxyethyl)-7-oxo-1-azabicyclo[3.2.0]hept-2-ene-2-carboxylic acid.
34. 3-(2-Amino-2-carbamoyl-1-methylethyl)thiomethyl-6-(1-hydroxyethyl)-7-oxo-1-azabicyclo[3.2.0]hept-2-ene-2-carboxylic acid.
35. 3-(2-Amino-2-carbazoyl-1-methylethyl)thiomethyl-6-(1-hydroxyethyl)-7-oxo-1-azabicyclo[3.2.0]hept-2-ene-2-carboxylic acid.

36. 3-(3-Aminopropylthiomethyl)-6-(1-hydroxyethyl)-7-oxo-1-azabicyclo[3.2.0]hept-2-ene-2-carboxylic acid.
37. 3-(3-Formimidoylaminopropylthiomethyl)-6-(1-hydroxyethyl)-7-oxo-1-azabicyclo[3.2.0]hept-2-ene-2-carboxylic acid.
38. 3-(3-Azidopropylthiomethyl)-6-(1-hydroxyethyl)-7-oxo-1-azabicyclo[3.2.0]hept-2-ene-2-carboxylic acid.
39. 6-(1-Hydroxyethyl)-7-oxo-3-(3-ureidopropylthiomethyl)-1-azabicyclo[3.2.0]hept-2-ene-2-carboxylic acid.
40. 3-(3-Aminooxypropylthiomethyl)-6-(1-hydroxyethyl)-7-oxo-1-azabicyclo[3.2.0]hept-2-ene-2-carboxylic acid.
41. 3-(3-Carbamoyloxypropylthiomethyl)-6-(1-hydroxyethyl)-7-oxo-1-azabicyclo[3.2.0]hept-2-ene-2-carboxylic acid.
42. 3-(3-Carbamoylpropylthiomethyl)-6-(1-hydroxyethyl)-7-oxo-1-azabicyclo[3.2.0]hept-2-ene-2-carboxylic acid.
43. 3-(3-Carbazoylpropylthiomethyl)-6-(1-hydroxyethyl)-7-oxo-1-azabicyclo[3.2.0]hept-2-ene-2-carboxylic acid.
44. 3-(3-Aminothiopropylthiomethyl)-6-(1-hydroxyethyl)-7-oxo-1-azabicyclo[3.2.0]hept-2-ene-2-carboxylic acid.
45. 3-(Aminomethylsulphinylmethyl)-6-(1-hydroxyethyl)-7-oxo-1-azabicyclo[3.2.0]hept-2-ene-2-carboxylic acid.
46. 3-(Formimidoylaminomethylsulphinylmethyl)-6-(1-hydroxyethyl)-7-oxo-1-azabicyclo[3.2.0]hept-2-ene-2-carboxylic acid.
47. 3-(Azidomethylsulphinylmethyl)-6-(1-hydroxyethyl)-7-oxo-1-azabicyclo[3.2.0]hept-2-ene-2-carboxylic acid.
48. 6-(1-Hydroxyethyl)-7-oxo-3-(ureidomethylsulphinylmethyl)-1-azabicyclo[3.2.0]hept-2-ene-2-carboxylic acid.
49. 3-(Aminooxymethylsulphinylmethyl)-6-(1-hydroxyethyl)-7-oxo-1-azabicyclo[3.2.0]hept-2-ene-2-carboxylic acid.
50. 3-(Carbamoyloxymethylsulphinylmethyl)-6-(1-hydroxyethyl)-7-oxo-1-azabicyclo[3.2.0]hept-2-ene-2-carboxylic acid.
51. 3-(Carbamoylmethylsulphinylmethyl)-6-(1-hydroxyethyl)-7-oxo-1-azabicyclo[3.2.0]hept-2-ene-2-carboxylic acid.
52. 3-Carbazoylmethylsulphinylmethyl-6-(1-hydroxyethyl)-7-oxo-1-azabicyclo[3.2.0]hept-2-ene-2-carboxylic acid.
53. 3-(Aminothiomethylsulphinylmethyl)-6-(1-hydroxyethyl)-7-oxo-1-azabicyclo[3.2.0]hept-2-ene-2-carboxylic acid.
54. 3-(2-Aminoethylsulphinylmethyl)-6-(1-hydroxyethyl)-7-oxo-1-azabicyclo[3.2.0]hept-2-ene-2-carboxylic acid.
55. 3-(2-Formimidoylaminoethylsulphinylmethyl)-6-(1-hydroxyethyl)-7-oxo-1-azabicyclo[3.2.0]hept-2-ene-2-carboxylic acid.
56. 3-(2-Azidoethylsulphinylmethyl)-6-(1-hydroxyethyl)-7-oxo-1-azabicyclo[3.2.0]hept-2-ene-2-carboxylic acid.
57. 6-(1-Hydroxyethyl)-7-oxo-3-(2-ureidoethylsulphinylmethyl)-1-azabicyclo[3.2.0]hept-2-ene-2-carboxylic acid.
58. 3-(2-Aminooxyethylsulphinylmethyl)-6-(1-hydroxyethyl)-7-oxo-1-azabicyclo[3.2.0]hept-2-ene-2-carboxylic acid.
59. 3-(2-Carbamoyloxyethylsulphinylmethyl)-6-(1-hydroxyethyl)-7-oxo-1-azabicyclo[3.2.0]hept-2-ene-2-carboxylic acid.
60. 3-(2-Carbamoylethylsulphinylmethyl)-6-(1-hydroxyethyl)-7-oxo-1-azabicyclo[3.2.0]hept-2-ene-2-carboxylic acid.
61. 3-(2-Carbazoylethylsulphinylmethyl)-6-(1-hydroxyethyl)-7-oxo-1-azabicyclo[3.2.0]hept-2-ene-2-carboxylic acid.
62. 3-(2-Aminothioethylsulphinylmethyl)-6-(1-hydroxyethyl)-7-oxo-1-azabicyclo[3.2.0]hept-2-ene-2-carboxylic acid.
63. 3-(2-Amino-2-carboxyethyl)sulphinylmethyl-6-(1-hydroxyethyl)-7-oxo-1-azabicyclo[3.2.0]hept-2-ene-2-carboxylic acid.
64. 3-(2-Amino-2-carbamoylethyl)sulphinylmethyl-6-(1-hydroxyethyl)-7-oxo-1-azabicyclo[3.2.0]hept-2-ene-2-carboxylic acid.
65. 3-(2-Amino-2-carbazoylethyl)sulphinylmethyl-6-(1-hydroxyethyl)-7-oxo-1-azabicyclo[3.2.0]hept-2-ene-2-carboxylic acid.
66. 3-(2-Amino-1-methylethyl)sulphinylmethyl-6-(1-hydroxyethyl)-7-oxo-1-azabicyclo[3.2.0]hept-2-ene-2-carboxylic acid.
67. 3-(2-Formimidoylamino-1-methylethyl)sulphinylmethyl-6-(1-hydroxyethyl)-7-oxo-1-azabicyclo[3.2.0]hept-2-ene-2-carboxylic acid.
68. 3-(2-Azido-1-methylethyl)sulphinylmethyl-6-(1-hydroxyethyl)-7-oxo-1-azabicyclo[3.2.0]hept-2-ene-2-carboxylic acid.
69. 6-(1-Hydroxyethyl)-3-(1-methyl-2-ureidoethyl)sulphinylmethyl-7-oxo-1-azabicyclo[3.2.0]hept-2-ene-2-carboxylic acid.
70. 3-(2-Aminooxy-1-methylethyl)sulphinylmethyl-6-(1-hydroxyethyl)-7-oxo-1-azabicyclo[3.2.0]hept-2-ene-2-carboxylic acid.
71. 3-(2-Carbamoyloxy-1-methylethyl)sulphinylmethyl-6-(1-hydroxyethyl)-7-oxo-1-azabicyclo[3.2.0]hept-2-ene-2-carboxylic acid.
72. 3-(2-Carbamoyl-1-methylethyl)sulphinylmethyl-6-(1-hydroxyethyl)-7-oxo-1-azabicyclo[3.2.0]hept-2-ene-2-carboxylic acid.
73. 3-(2-Carbazoyl-1-methylethyl)sulphinylmethyl-6-(1-hydroxyethyl)-7-oxo-1-azabicyclo[3.2.0]hept-2-ene-2-carboxylic acid.
74. 3-(2-Aminothio-1-methylethyl)sulphinylmethyl-6-(1-hydroxyethyl)-7-oxo-1-azabicyclo[3.2.0]hept-2-ene-2-carboxylic acid.
75. 3-(2-Amino-2-carboxy-1-methylethyl)sulphinylmethyl-6-(1-hydroxyethyl)-7-oxo-1-azabicyclo[3.2.0]hept-2-ene-2-carboxylic acid.
76. 3-(2-Amino-2-methoxycarbonyl-1-methylethyl)sulphinylmethyl-6-(1-hydroxyethyl)-7-oxo-1-azabicyclo[3.2.0]hept-2-ene-2-carboxylic acid.
77. 3-(2-Amino-2-carbamoyl-1-methylethyl)sulphinylmethyl-6-(1-hydroxyethyl)-7-oxo-1-azabicyclo[3.2.0]hept-2-ene-2-carboxylic acid.
78. 3-(2-Amino-2-carbazoyl-1-methylethyl)sulphinylmethyl-6-(1-hydroxyethyl)-7-oxo-1-azabicyclo[3.2.0]hept-2-ene-2-carboxylic acid.
79. 3-(3-Aminopropylsulphinylmethyl)-6-(1-hydroxyethyl)-7-oxo-1-azabicyclo[3.2.0]hept-2-ene-2-carboxylic acid.
80. 3-(3-Formimidoylaminopropylsulphinylmethyl)-6-(1-hydroxyethyl)-7-oxo-1-azabicyclo[3.2.0]hept-2-ene-2-carboxylic acid.

81. 3-(3-Azidopropylsulphinylmethyl)-6-(1-hydroxyethyl)-7-oxo-1-azabicyclo[3.2.0]hept-2-ene-2-carboxylic acid.
82. 6-(1-Hydroxyethyl)-7-oxo-3-(3-ureidopropylsulphinylmethyl)-1-azabicyclo[3.2.0]hept-2-ene-2-carboxylic acid.
83. 3-(3-Aminooxypropylsulphinylmethyl)-6-(1-hydroxyethyl)-7-oxo-1-azabicyclo[3.2.0]hept-2-ene-2-carboxylic acid.
84. 3-(3-Carbamoyloxypropylsulphinylmethyl)-6-(1-hydroxyethyl)-7-oxo-1-azabicyclo[3.2.0]hept-2-ene-2-carboxylic acid.
85. 3-(3-Carbamoylpropylsulphinylmethyl)-6-(1-hydroxyethyl)-7-oxo-1-azabicyclo[3.2.0]hept-2-ene-2-carboxylic acid.
86. 3-(3-Carbazoylpropylsulphinylmethyl)-6-(1-hydroxyethyl)-7-oxo-1-azabicyclo[3.2.0]hept-2-ene-2-carboxylic acid.
87. 3-(3-Aminothiopropylsulphinylmethyl)-6-(1-hydroxyethyl)-7-oxo-1-azabicyclo[3.2.0]hept-2-ene-2-carboxylic acid.
88. 3-(Aminomethylsulphonylmethyl)-6-(1-hydroxyethyl)-7-oxo-1-azabicyclo[3.2.0]hept-2-ene-2-carboxylic acid.
89. 3-(Formimidoylaminomethylsulphonylmethyl)-6-(1-hydroxyethyl)-7-oxo-1-azabicyclo[3.2.0]hept-2-ene-2-carboxylic acid.
90. 3-(Azidomethylsulphonylmethyl)-6-(1-hydroxyethyl)-7-oxo-1-azabicyclo[3.2.0]hept-2-ene-2-carboxylic acid.
91. 6-(1-Hydroxyethyl)-7-oxo-3-(ureidomethylsulphonylmethyl)-1-azabicyclo[3.2.0]hept-2-ene-2-carboxylic acid.
92. 3-(Aminooxymethylsulphonylmethyl)-6-(1-hydroxyethyl)-7-oxo-1-azabicyclo[3.2.0]hept-2-ene-2-carboxylic acid.
93. 3-(Carbamoyloxymethylsulphonylmethyl)-6-(1-hydroxyethyl)-7-oxo-1-azabicyclo[3.2.0]hept-2-ene-2-carboxylic acid.
94. 3-(Carbamoylmethylsulphonylmethyl)-6-(1-hydroxyethyl)-7-oxo-1-azabicyclo[3.2.0]hept-2-ene-2-carboxylic acid.
95. 3-Carbazoylmethylsulphonylmethyl-6-(1-hydroxyethyl)-7-oxo-1-azabicyclo[3.2.0]hept-2-ene-2-carboxylic acid.
96. 3-(Aminothiomethylsulphonylmethyl)-6-(1-hydroxyethyl)-7-oxo-1-azabicyclo[3.2.0]hept-2-ene-2-carboxylic acid.
97. 3-(2-Aminoethylsulphonylmethyl)-6-(1-hydroxyethyl)-7-oxo-1-azabicyclo[3.2.0]hept-2-ene-2-carboxylic acid.
98. 3-(2-Formimidoylaminoethylsulphonylmethyl)-6-(1-hydroxyethyl)-7-oxo-1-azabicyclo[3.2.0]hept-2-ene-2-carboxylic acid.
99. 3-(2-Azidoethylsulphonylmethyl)-6-(1-hydroxyethyl)-7-oxo-1-azabicyclo[3.2.0]hept-2-ene-2-carboxylic acid.
100. 6-(1-Hydroxyethyl)-7-oxo-3-(2-ureidoethylsulphonylmethyl)-1-azabicyclo[3.2.0]hept-2-ene-2-carboxylic acid.
101. 3-(2-Aminooxyethylsulphonylmethyl)-6-(1-hydroxyethyl)-7-oxo-1-azabicyclo[3.2.0]hept-2-ene-2-carboxylic acid.
102. 3-(2-Carbamoyloxyethylsulphonylmethyl)-6-(1-hydroxyethyl)-7-oxo-1-azabicyclo[3.2.0]hept-2-ene-2-carboxylic acid.
103. 3-(2-Carbamoylethylsulphonylmethyl)-6-(1-hydroxyethyl)-7-oxo-1-azabicyclo[3.2.0]hept-2-ene-2-carboxylic acid.
104. 3-(2-Carbazoylethylsulphonylmethyl)-6-(1-hydroxyethyl)-7-oxo-1-azabicyclo[3.2.0]hept-2-ene-2-carboxylic acid.
105. 3-(2-Aminothioethylsulphonylmethyl)-6-(1-hydroxyethyl)-7-oxo-1-azabicyclo[3.2.0]hept-2-ene-2-carboxylic acid.
106. 3-(2-Amino-2-carboxyethyl)sulphonylmethyl-6-(1-hydroxyethyl)-7-oxo-1-azabicyclo[3.2.0]hept-2-ene-2-carboxylic acid.
107. 3-(2-Amino-2-carbamoylethyl)sulphonylmethyl-6-(1-hydroxyethyl)-7-oxo-1-azabicyclo[3.2.0]hept-2-ene-2-carboxylic acid.
108. 3-(2-Amino-2-carbazoylethyl)sulphonylmethyl-6-(1-hydroxyethyl)-7-oxo-1-azabicyclo[3.2.0]hept-2-ene-2-carboxylic acid.
109. 3-(2-Amino-1-methylethyl)sulphonylmethyl-6-(1-hydroxyethyl)-7-oxo-1-azabicyclo[3.2.0]hept-2-ene-2-carboxylic acid.
110. 3-(2-Formimidoylamino-1-methylethyl)sulphonylmethyl-6-(1-hydroxyethyl)-7-oxo-1-azabicyclo[3.2.0]hept-2-ene-2-carboxylic acid.
111. 3-(2-Azido-1-methylethyl)sulphonylmethyl-6-(1-hydroxyethyl)-7-oxo-1-azabicyclo[3.2.0]hept-2-ene-2-carboxylic acid.
112. 6-(1-Hydroxyethyl)-3-(1-methyl-2-ureidoethyl)sulphonylmethyl-7-oxo-1-azabicyclo[3.2.0]hept-2-ene-2-carboxylic acid.
113. 3-(2-Aminooxy-1-methylethyl)sulphonylmethyl-6-(1-hydroxyethyl)-7-oxo-1-azabicyclo[3.2.0]hept-2-ene-2-carboxylic acid.
114. 3-(2-Carbamoyloxy-1-methylethyl)sulphonylmethyl-6-(1-hydroxyethyl)-7-oxo-1-azabicyclo[3.2.0]hept-2-ene-2-carboxylic acid.
115. 3-(2-Carbamoyl-1-methylethyl)sulphonylmethyl-6-(1-hydroxyethyl)-7-oxo-1-azabicyclo[3.2.0]hept-2-ene-2-carboxylic acid.
116. 3-(2-Carbazoyl-1-methylethyl)sulphonylmethyl-6-(1-hydroxyethyl)-7-oxo-1-azabicyclo[3.2.0]hept-2-ene-2-carboxylic acid.
117. 3-(2-Aminothio-1-methylethyl)sulphonylmethyl-6-(1-hydroxyethyl)-7-oxo-1-azabicyclo[3.2.0]hept-2-ene-2-carboxylic acid.
118. 3-(2-Amino-2-carboxy-1-methylethyl)sulphonylmethyl-6-(1-hydroxyethyl)-7-oxo-1-azabicyclo[3.2.0]hept-2-ene-2-carboxylic acid.
119. 3-(2-Amino-2-methoxycarbonyl-1-methylethyl)sulphonylmethyl-6-(1-hydroxyethyl)-7-oxo-1-azabicyclo[3.2.0]hept-2-ene-2-carboxylic acid.
120. 3-(2-Amino-2-carbamoyl-1-methylethyl)sulphonylmethyl-6-(1-hydroxyethyl)-7-oxo-1-azabicyclo[3.2.0]hept-2-ene-2-carboxylic acid.
121. 3-(2-Amino-2-carbazoyl-1-methylethyl)sulphonylmethyl-6-(1-hydroxyethyl)-7-oxo-1-azabicyclo[3.2.0]hept-2-ene-2-carboxylic acid.
122. 3-(3-Aminopropylsulphonylmethyl)-6-(1-hydroxyethyl)-7-oxo-1-azabicyclo[3.2.0]hept-2-ene-2-carboxylic acid.
123. 3-(3-Formimidoylaminopropylsulphonylmethyl)-6-(1-hydroxyethyl)-7-oxo-1-azabicyclo[3.2.0]hept-2-ene-2-carboxylic acid.
124. 3-(3-Azidopropylsulphonylmethyl)-6-(1-hydroxyethyl)-7-oxo-1-azabicyclo[3.2.0]hept-2-ene-2-carboxylic acid.

125. 6-(1-Hydroxyethyl)-7-oxo-3-(3-ureidopropylsulphonylmethyl)-1-azabicyclo[3.2.0]hept-2-ene-2-carboxylic acid.
126. 3-(3-Aminooxypropylsulphonylmethyl)-6-(1-hydroxyethyl)-7-oxo-1-azabicyclo[3.2.0]hept-2-ene-2-carboxylic acid.
127. 3-(3-Carbamoyloxypropylsulphonylmethyl)-6-(1-hydroxyethyl)-7-oxo-1-azabicyclo[3.2.0]hept-2-ene-2-carboxylic acid.
128. 3-(3-Carbamoylpropylsulphonylmethyl)-6-(1-hydroxyethyl)-7-oxo-1-azabicyclo[3.2.0]hept-2-ene-2-carboxylic acid.
129. 3-(3-Carbazoylpropylsulphonylmethyl)-6-(1-hydroxyethyl)-7-oxo-1-azabicyclo[3.2.0]hept-2-ene-2-carboxylic acid.
130. 3-(3-Aminothiopropylsulphonylmethyl)-6-(1-hydroxyethyl)-7-oxo-1-azabicyclo[3.2.0]hept-2-ene-2-carboxylic acid.
131. 3-(Aminomethyloxymethyl)-6-(1-hydroxyethyl)-7-oxo-1-azabicyclo[3.2.0]hept-2-ene-2-carboxylic acid.
132. 3-(Formimidoylaminomethyloxymethyl)-6-(1-hydroxyethyl)-7-oxo-1-azabicyclo[3.2.0]hept-2-ene-2-carboxylic acid.
133. 3-(Azidomethyloxymethyl)-6-(1-hydroxyethyl)-7-oxo-1-azabicyclo[3.2.0]hept-2-ene-2-carboxylic acid.
134. 6-(1-Hydroxyethyl)-7-oxo-3-(ureidomethyloxymethyl)-1-azabicyclo[3.2.0]hept-2-ene-2-carboxylic acid.
135. 3-(Aminooxymethyloxymethyl)-6-(1-hydroxyethyl)-7-oxo-1-azabicyclo[3.2.0]hept-2-ene-2-carboxylic acid.
136. 3-(Carbamoyloxymethyloxymethyl)-6-(1-hydroxyethyl)-7-oxo-1-azabicyclo[3.2.0]hept-2-ene-2-carboxylic acid.
137. 3-(Carbamoylmethyloxymethyl)-6-(1-hydroxyethyl)-7-oxo-1-azabicyclo[3.2.0]hept-2-ene-2-carboxylic acid.
138. 3-(Carbazoylmethyloxymethyl)-6-(1-hydroxyethyl)-7-oxo-1-azabicyclo[3.2.0]hept-2-ene-2-carboxylic acid.
139. 3-(Aminothiomethyloxymethyl)-6-(1-hydroxyethyl)-7-oxo-1-azabicyclo[3.2.0]hept-2-ene-2-carboxylic acid.
140. 3-(2-Aminoethyloxymethyl)-6-(1-hydroxyethyl)-7-oxo-1-azabicyclo[3.2.0]hept-2-ene-2-carboxylic acid.
141. 3-(2-Formimidoylaminoethyloxymethyl)-6-(1-hydroxyethyl)-7-oxo-1-azabicyclo[3.2.0]hept-2-ene-2-carboxylic acid.
142. 3-(2-Azidoethyloxymethyl)-6-(1-hydroxyethyl)-7-oxo-1-azabicyclo[3.2.0]hept-2-ene-2-carboxylic acid.
143. 6-(1-Hydroxyethyl)-7-oxo-3-(2-ureidoethyloxymethyl)-1-azabicyclo[3.2.0]hept-2-ene-2-carboxylic acid.
144. 3-(2-Aminooxyethyloxymethyl)-6-(1-hydroxyethyl)-7-oxo-1-azabicyclo[3.2.0]hept-2-ene-2-carboxylic acid.
145. 3-(2-Carbamoyloxyethyloxymethyl)-6-(1-hydroxyethyl)-7-oxo-1-azabicyclo[3.2.0]hept-2-ene-2-carboxylic acid.
146. 3-(2-Carbamoylethyloxymethyl)-6-(1-hydroxyethyl)-7-oxo-1-azabicyclo[3.2.0]hept-2-ene-2-carboxylic acid.
147. 3-(2-Carbazoylethyloxymethyl)-6-(1-hydroxyethyl)-7-oxo-1-azabicyclo[3.2.0]hept-2-ene-2-carboxylic acid.
148. 3-(2-Aminothioethyloxymethyl)-6-(1-hydroxyethyl)-7-oxo-1-azabicyclo[3.2.0]hept-2-ene-2-carboxylic acid.
149. 3-(2-Amino-2-carboxyethyl)oxymethyl-6-(1-hydroxyethyl)-7-oxo-1-azabicyclo[3.2.0]hept-2-ene-2-carboxylic acid.
150. 3-(2-Amino-2-carbamoylethyl)oxymethyl-6-(1-hydroxyethyl)-7-oxo-1-azabicyclo[3.2.0]hept-2-ene-2-carboxylic acid.
151. 3-(2-Amino-2-carbazoylethyl)oxymethyl-6-(1-hydroxyethyl)-7-oxo-1-azabicyclo[3.2.0]hept-2-ene-2-carboxylic acid.
152. 3-(2-Amino-1-methylethyl)oxymethyl-6-(1-hydroxyethyl)-7-oxo-1-azabicyclo[3.2.0]hept-2-ene-2-carboxylic acid.
153. 3-(2-Formimidoylamino-1-methylethyl)oxymethyl-6-(1-hydroxyethyl)-7-oxo-1-azabicyclo[3.2.0]hept-2-ene-2-carboxylic acid.
154. 3-(2-Azido-1-methylethyl)oxymethyl-6-(1-hydroxyethyl)-7-oxo-1-azabicyclo[3.2.0]hept-2-ene-2-carboxylic acid.
155. 6-(1-Hydroxyethyl)-3-(1-methyl-2-ureidoethyl)oxymethyl-7-oxo-1-azabicyclo[3.2.0]hept-2-ene-2-carboxylic acid.
156. 3-(2-Aminooxy-1-methylethyl)oxymethyl-6-(1-hydroxyethyl)-7-oxo-1-azabicyclo[3.2.0]hept-2-ene-2-carboxylic acid.
157. 3-(2-Carbamoyloxy-1-methylethyl)oxymethyl-6-(1-hydroxyethyl)-7-oxo-1-azabicyclo[3.2.0]hept-2-ene-2-carboxylic acid.
158. 3-(2-Carbamoyl-1-methylethyl)oxymethyl-6-(1-hydroxyethyl)-7-oxo-1-azabicyclo[3.2.0]hept-2-ene-2-carboxylic acid.
159. 3-(2-Carbazoyl-1-methylethyl)oxymethyl-6-(1-hydroxyethyl)-7-oxo-1-azabicyclo[3.2.0]hept-2-ene-2-carboxylic acid.
160. 3-(2-Aminothio-1-methylethyl)oxymethyl-6-(1-hydroxyethyl)-7-oxo-1-azabicyclo[3.2.0]hept-2-ene-2-carboxylic acid.
161. 3-(2-Amino-2-carboxy-1-methylethyl)oxymethyl-6-(1-hydroxyethyl)-7-oxo-1-azabicyclo[3.2.0]hept-2-ene-2-carboxylic acid.
162. 3-(2-Amino-2-methoxycarbonyl-1-methylethyl)oxymethyl-6-(1-hydroxyethyl)-7-oxo-1-azabicyclo[3.2.0]hept-2-ene-2-carboxylic acid.
163. 3-(2-Amino-2-carbamoyl-1-methylethyl)oxymethyl-6-(1-hydroxyethyl)-7-oxo-1-azabicyclo[3.2.0]hept-2-ene-2-carboxylic acid.
164. 3-(2-Amino-2-carbazoyl-1-methylethyl)oxymethyl-6-(1-hydroxyethyl)-7-oxo-1-azabicyclo[3.2.0]hept-2-ene-2-carboxylic acid.
165. 3-(3-Aminopropyloxymethyl)-6-(1-hydroxyethyl)-7-oxo-1-azabicyclo[3.2.0]hept-2-ene-2-carboxylic acid.
166. 3-(3-Formimidoylaminopropyloxymethyl)-6-(1-hydroxyethyl)-7-oxo-1-azabicyclo[3.2.0]hept-2-ene-2-carboxylic acid.
167. 3-(3-Azidopropyloxymethyl)-6-(1-hydroxyethyl)-7-oxo-1-azabicyclo[3.2.0]hept-2-ene-2-carboxylic acid.
168. 6-(1-Hydroxyethyl)-7-oxo-3-(3-ureidopropyloxymethyl)-1-azabicyclo[3.2.0]hept-2-ene-2-carboxylic acid.
169. 3-(3-Aminooxypropyloxymethyl)-6-(1-hydroxyethyl)-7-oxo-1-azabicyclo[3.2.0]hept-2-ene-2-carboxylic acid.
170. 3-(3-Carbamoyloxypropyloxymethyl)-6-(1-hydroxyethyl)-7-oxo-1-azabicyclo[3.2.0]hept-2-ene-2-carboxylic acid.

171. 3-(3-Carbamoylpropyloxymethyl)-6-(1-hydroxyethyl)-7-oxo-1-azabicyclo[3.2.0]hept-2-ene-2-carboxylic acid.
172. 3-(3-Carbazoylpropyloxymethyl)-6-(1-hydroxyethyl)-7-oxo-1-azabicyclo[3.2.0]hept-2-ene-2-carboxylic acid.
173. 3-(3-Aminothiopropyloxymethyl)-6-(1-hydroxyethyl)-7-oxo-1-azabicyclo[3.2.0]hept-2-ene-2-carboxylic acid.
174. 3-(2-Aminoethylthiomethyl)-6-(1-hydroxy-1-methylethyl)-7-oxo-1-azabicyclo[3.2.0]hept-2-ene-2-carboxylic acid.
175. 3-(2-Ethoxyethylthiomethyl)-6-(1-hydroxyethyl)-7-oxo-1-azabicyclo[3.2.0]hept-2-ene-2-carboxylic acid.
176. 3-(Ethylthiomethyl)-7-oxo-1-azabicyclo[3.2.0]-hept-2-ene-2-carboxylic acid.
177. Pivaloyloxymethyl 3-(2-aminoethylthiomethyl)-6-(1-hydroxyethyl)-7-oxo-1-azabicyclo[3.2.0]hept-2-ene-2-carboxylate.
178. Pivaloyloxymethyl 3-(2-formimidoylaminoethylthiomethyl)-6-(1-hydroxyethyl)-7-oxo-1-azabicyclo[3.2.0]hept-2-ene-2-carboxylate.
179. Pivaloyloxymethyl 3-(2-carbamoylethylthiomethyl)-6-(1-hydroxyethyl)-7-oxo-1-azabicyclo[3.2.0]hept-2-ene-2-carboxylate.
180. Pivaloyloxymethyl 3-(2-aminoethylsulphinylmethyl)-6-(1-hydroxyethyl)-7-oxo-1-azabicyclo[3.2.0]hept-2-ene-2-carboxylate.
181. Pivaloyloxymethyl 3-(2-formimidoylaminoethylsulphinylmethyl)-6-(1-hydroxyethyl)-7-oxo-1-azabicyclo-[3.2.0]hept-2-ene-2-carboxylate.
182. Pivaloyloxymethyl 3-(2-carbamoylethylsulphinylmethyl)-6-(1-hydroxyethyl)-7-oxo-1-azabicyclo[3.2.0]-hept-2-ene-2-carboxylate.
183. Pivaloyloxymethyl 3-(2-aminoethylsulphonylmethyl)-6-(1-hydroxyethyl)-7-oxo-1-azabicyclo[3.2.0]hept-2-ene-2-carboxylate.
184. Pivaloyloxymethyl 3-(2-formimidoylaminoethylsulphonylmethyl)-6-(1-hydroxyethyl)-7-oxo-1-azabicyclo-[3.2.0]hept-2-ene-2-carboxylate.
185. Pivaloyloxymethyl 3-(2-carbamoylethylsulphonylmethyl)-6-(1-hydroxyethyl)-7-oxo-1-azabicyclo[3.2.0]hept-2-ene-2-carboxylate.
186. Pivaloyloxymethyl 3-(2-amino-1-methylethyl)thiomethyl-6-(1-hydroxyethyl)-7-oxo-1-azabicyclo[3.2.0]hept-2-ene-2-carboxylate.
187. Pivaloyloxymethyl 3-(2-formimidoylamino-1-methylethyl)thiomethyl-6-(1-hydroxyethyl)-7-oxo-1-azabicyclo-[3.2.0]hept-2-ene-2-carboxylate.
188. Pivaloyloxymethyl 3-(2-carbamoyl-1-methylethyl)thiomethyl-6-(1-hydroxyethyl)-7-oxo-1-azabicyclo[3.2.0]-hept-2-ene-2-carboxylate.
189. Pivaloyloxymethyl 3-(2-amino-1-methylethyl)sulphinylmethyl-6-(1-hydroxyethyl)-7-oxo-1-azabicyclo-[3.2.0]hept-2-ene-2-carboxylate.
190. Pivaloyloxymethyl 3-(2-formimidoylamino-1-methylethyl)sulphinylmethyl-6-(1-hydroxyethyl)-7-oxo-1-azabicyclo-[3.2.0]hept-2-ene-2-carboxylate.
191. Pivaloyloxymethyl 3-(2-carbamoyl-1-methylethyl)sulphinylmethyl-6-(1-hydroxyethyl)-7-oxo-1-azabicyclo-[3.2.0]hept-2-ene-2-carboxylate.
192. Pivaloyloxymethyl 3-(2-amino-1-methylethyl)sulphonylmethyl-6-(1-hydroxyethyl)-7-oxo-1-azabicyclo[3.2.0]-hept-2-ene-2-carboxylate.
193. Pivaloyloxymethyl 3-(2-formimidoylamino-1-methylethyl)sulphonylmethyl-6-(1-hydroxyethyl)-7-oxo-1-azabicyclo[3.2.0]hept-2-ene-2-carboxylate.
194. Pivaloyloxymethyl 3-(2-(carbamoyl-1-methylethyl)sulphonylmethyl-6-(1-hydroxyethyl)-7-oxo-1-azabicyclo[3.2.0]hept-2-ene-2-carboxylate.

Of these compounds, preferred compounds are Compounds No. 10, 11, 19, 20, 23, 24, 32, 33, 36, 37, 54, 55, 63, 66, 67, 75, 76, 97, 98, 106, 107, 109, 110, 118, 119, 140, 141, 149, 152, 153, 161, 162, 177, 178, 186 and 187. The more preferred compounds are Compounds No. 10 and its pivaloyloxymethyl ester (Compound No. 177), Compound No. 11 and its pivaloyloxymethyl ester (Compound No. 178), Compound No. 23 and its pivaloyloxymethyl ester (Compound No. 186) and Compound No. 24 and its pivaloyloxymethyl ester (Compound No. 187). The most preferred compound is Compound No. 10.

Preferred isomers of the compounds listed above are those having the (5R,6S) or (5R,6R) configuration and in those compounds where $R^1$ represents an alkyl group having a substituent (such as a hydroxy group, an amino group or an acetamido group) at the α-position, this α-substituent is preferably in the R configuration.

The compounds of formula (I) can be prepared by heating a phosphorus-ylide compound of formula (II):

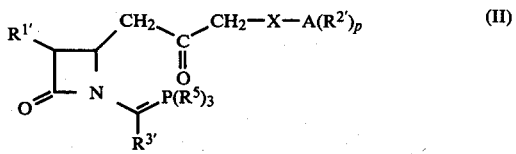

(in which $R^{1'}$, $R^{2'}$, $R^{3'}$, $R^5$, X, A and p are as defined above) to give a compound of formula (III):

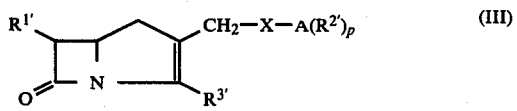

and then if necessary removing any protecting groups and, if necessary, converting a compound in which $R^{2'}$ represents an amino group to a compound in which $R^2$ represents a group of formula

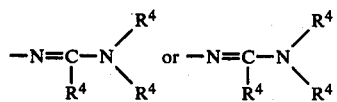

(in which $R^4$ is as defined above).

The ring closure reaction of compound (II) to give compound (III) is suitably carried out in a solvent, the nature of which is not critical, provided it has no adverse effect on the ring-closure reaction. Suitable solvents include: ethers, such as tetrahydrofuran or dioxan; halogenated hydrocarbons, such as methylene chloride or chloroform; and aromatic hydrocarbons, such as benzene or toluene. The temperature to which the phosphorus-ylide compound (II) is heated to effect ring closure may vary over a wide range but is preferably within the range from 30° C. to 200° C. The time required for this ring closure reaction will depend upon the reaction temperature but the reaction will normally be complete within from 1 to 40 hours. In order to prevent side reactions, the ring-closure reaction is preferably carried out under a stream of inert gas (such as argon or nitrogen) and in the presence of a catalytic amount of anti-oxidant (such as hydroquinone).

After completion of the reaction, the resulting compound of formula (III) may be recovered from the reaction mixture by conventional means, for example by distilling off the solvent and purifying the resulting residue by recrystallization, reprecipitation or column chromatography.

The compound of formula (III) thus recovered may then be subjected to reactions to remove any protecting groups, as is well-known in the art and described in greater detail hereafter.

Conversion of a compound of formula (III) or (I) in which $R^{2'}$ or $R^2$ represents an amino group or an alkyl-substituted amino group to a compound in which this group is a group of formula

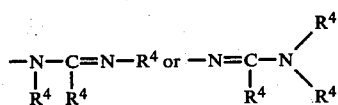

can be accomplished by reacting said compound of (III) or (I) with a compound of formula (IV):

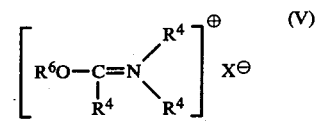

(in which $R^4$ is as defined above, $R^6$ represents a lower alkyl group, for example a methyl, ethyl, propyl, isopropyl, butyl or isobutyl group, and X-represents a halide ion). This reaction is described in more detail hereafter.

Preparation of the phosphorus-ylide compound of formula (II) used as the starting material in the process of the present invention and the various steps of the process of the invention are further illustrated with reference to the following reaction scheme:

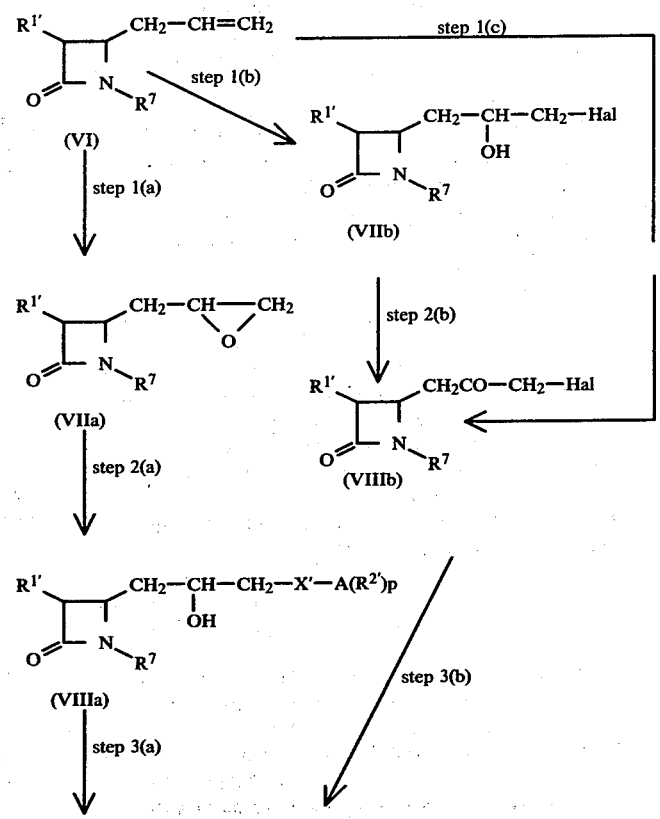

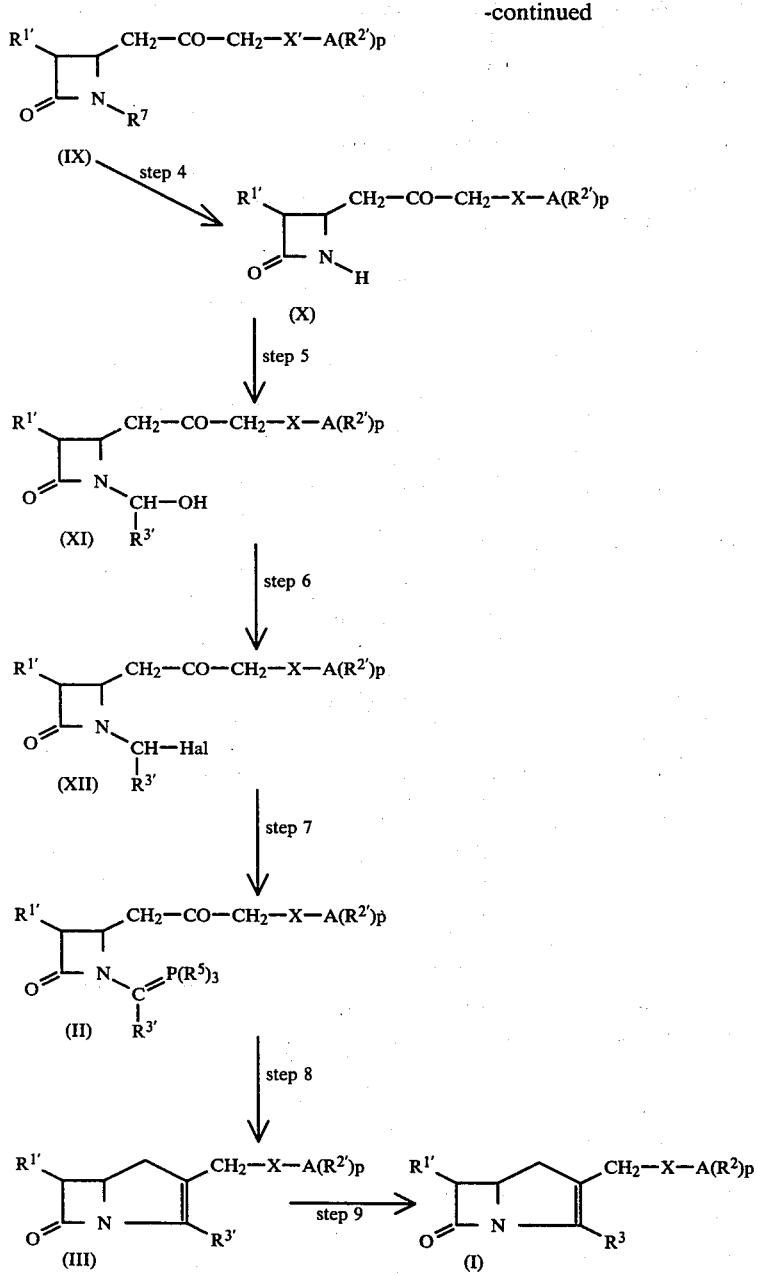

-continued

In the above formulae, $R^1$, $R^{1'}$, $R^2$, $R^{2'}$, $R^3$, $R^{3'}$, X, A, p and $R^5$ are as defined above;

$R^7$ represents a hydrogen atom or a protecting group for the β-lactam nitrogen atom;

Hal represents a halogen atom; and

X' represents an oxy group or a thio group.

Examples of groups which may be represented by $R^{1'}$ and $R^{2'}$ in the above formulae, apart from those corresponding to the groups already exemplified for $R^1$ and $R^2$, include: as protected hydroxy groups, alkanoyloxy groups (for example those already exemplified for $R^2$), aralkyloxycarbonyloxy groups (e.g. benzyloxycarbonyloxy or p-nitrobenzyloxycarbonyloxy) or tri(lower alkyl)silyloxy groups, (e.g. t-butyldimethylsilyloxy); as protected amino groups, substituted acetylamino groups (e.g. the lower alkanoylamino groups hitherto exemplified for $R^2$, or the phenylacetylamino and phenoxyacetaylamino groups) or aralkyloxycarbonylamino groups (e.g. benzyloxycarbonylamino or p-nitrobenzyloxycarbonylamino groups); as protected hydrazino groups, aralkoxycarbonylhydrazino groups (e.g. benzyloxycarbonylhydrazino or p-nitrobenzyloxycarbonylhydrazino); as protected mercapto groups, lower alkanoylthio groups (e.g. acetylthio, propionylthio, butyrylthio or isobutyrylthio; as protected hydroxyamino groups, lower alkanoyloxyamino groups (e.g. acetoxyamino or propionyloxyamino) or aralkyloxycarbonyloxyamino groups (e.g. benzyloxycarbonyloxyamino or p-nitrobenzyloxycarbonyloxyamino); as protected aminooxy groups, aralkyloxycarbonylaminooxy groups (e.g. benzyloxycarbonylaminooxy or p-nitrobenzyloxycarbonylaminooxy); as protected carboxy groups, lower alkoxycarbonyl groups (e.g. methoxycarbonyl, ethoxycarbonyl or propoxycarbonyl), aralkyloxycarbonyl groups (e.g. benzyloxycarbonyl, p-nitrobenzyloxycarbonyl or p-methoxybenzyloxycarbonyl), the benzhydryloxycarbonyl group, halogenated (lower alkoxy)-carbonyl groups (e.g. 2,2-dibromoethoxycarbonyl or 2,2,2-trichloroethoxycarbonyl) or substituted or unsubstituted phenacyloxycarbonyl groups (e.g. phenacyloxycarbonyl or p-bromophenacyloxycarbonyl); and, as the protected guanidinocarbonyl groups, benzyloxycarbonylguanidinocarbonyl or p-nitrobenzyloxycarbonylguanidinocarbonyl).

Examples of protected carboxy groups which may be represented by $R^{3'}$ include those mentioned above in relation to the groups represented by $R^{1'}$ and $R^{2'}$. Where $R^3$ represents a protected carboxy group, this may be any one of these groups which is capable of removal under physiological conditions.

Examples of the alkyl groups which may be $R^5$ include the butyl and octyl groups, whilst examples of the aryl groups which may be represented by $R^5$ include the phenyl and tolyl groups.

Examples of protecting groups for the β-lactam nitrogen atom which may be represented by $R^7$ include trialkylsilyl groups (e.g. t-butyldimethylsilyl) and the tetrahydropyranyl group.

Examples of the halogen atoms which may be represented by Hal include the chlorine and bromine atoms.

The 4-allylazetidinone compounds of formula (VI) which are used as starting materials in this reaction scheme may be synthesized by the process described in Japanese Patent Application Kokai (i.e. as laid-open to public inspection) No. 7251/1980.

The reaction scheme is now described in more detail below:

Step 1(a)

The compound of formula (VIIa) is prepared from the compound of formula (VI) by reaction with an epoxidizing agent in the presence of a solvent. There is no particular limitation on the nature of the epoxidizing agent used in this reaction, provided that it is capable of forming an epoxide from an ethylenic compound. Examples of preferred epoxidizing agents include: organic peroxides, such as performic acid, peracetic acid, perbenzoic acid, m-chloroperbenzoic acid or perphthalic acid; and hydrogen peroxide. The nature of the solvent is also not critical, provided that it has no adverse effect on the reaction. Examples of suitable solvents include: halogenated hydrocarbons, such as methylene chloride or chloroform; ethers, such as tetrahydrofuran or dioxan; aromatic hydrocarbons, such as benzene or toluene; and fatty acids, such as formic or acetic acid. There is also no particular limitation on the reaction temperature and the reaction will usually be carried out at a temperature which may vary from $-30°$ C. to $+50°$ C. The time required for the reaction will vary depending upon the nature of the starting material of formula (VI) and the epoxidizing agent as well as upon the reaction temperature, but the reaction will normally be complete within a period which may range from about 1 hour to 24 hours.

After completion of the reaction, the desired compound of formula (VIIa) may be recovered from the reaction mixture by conventional means. For example, excess epoxidizing agent can be decomposed by adding an aqueous solution of sodium hydrogen sulphite. The mixture is then poured into water and extracted with an organic solvent. The organic extract is washed, for example with aqueous sodium bicarbonate and saturated aqueous sodium chloride, after which it is dried over anhydrous sodium sulphate. After distilling off the solvent, the resulting residue can be purified by recrystallization and/or column chromatography.

Alternatively, although this is not shown in the above reaction scheme, the epoxide (VIIa) can be prepared by treating the halohydrin compound (VIIb) obtained in step 1(b) with an organic or inorganic base at a temperature of from 0° C. to 30° C. for a suitable period, e.g. from 10 to 60 minutes.

Step 2(a)

In this step, the expoxide (VIIa) obtained in step 1(a) is reacted with a nucleophilic agent of formula (XIV):

$$H-X'-A(R^{2'})_p \qquad (XIV)$$

(in which $R^{2'}$, p, X' and A are as defined above) or with a reactive derivative thereof, in a suitable solvent.

Suitable reactive derivatives of the nucleophilic agent (XIV) include alkali metal or alkaline earth metal salts (for example the lithium, sodium, potassium calcium or magnesium salts), the silver salt, or a salt with an organic base (for example a salt with triethylamine, N-methylmorpholine or tetraethylammonium hydroxide). The nature of the solvent used in this reaction is not critical, provided that it has no adverse effect upon the reaction. Suitable solvents include: halogenated hydrocarbons, such as methylene chloride and chloroform; and ethers, such diethyl ether and tetrahydrofuran. There is no particular limitation on the reaction temperature and the reaction is normally carried out at a temperature from $-10°$ C. to $+100°$ C. The time required for the reaction will vary depending upon the reagents and the reaction temperature, but the reaction will normally be complete within a period of from 10 minutes to 2 hours.

Alternatively, the reaction may be carried out by reacting the epoxide of formula (VIIa) with the nucleophilic agent of formula (XIV) in the presence of a base (such as n-butyllithium) or a Lewis acid (such as boron trifluoride diethyl etherate.

After completion of the reaction, the desired product of formula (VIIIa) may be recovered from the reaction mixture by conventional means. For example, the reaction mixture is first diluted with a water-immiscible organic solvent (such as ethyl acetate, diethyl ether, benzene or chloroform) and, if necessary, neutralized. The mixture is then washed with water and dried, after which the solvent is distilled off. Finally, the resulting residue is purified by recrystallization, reprecipitation or column chromatography to give the desired product.

Step 3(a)

In this step, a compound of formula (IX) is prepared by oxidizing the secondary alcohol of formula (VIIIa) to the corresponding ketone compound, in the presence of a suitable solvent.

The nature of the oxidizing agent used in this step is not critical, provided that it is capable of converting a secondary alcohol to a ketone. Examples of such oxidizing agents include chromates, manganates, hypohalogenous acid salts, halogens, N-haloamides, N-haloimides, oxygen and a combination of dimethyl sulphoxide with an acid anhydride. The nature of the solvent employed in this reaction is not critical, provided that it has no adverse effect on the reaction. Suitable solvents include: halogenated hydrocarbons, such as methylene chloride and chloroform; ketones, such as acetone and methyl ethyl ketone; ethers, such as tetrahydrofuran and dioxan, and esters, such as methyl acetate and ethyl acetate. The reaction is preferably carried out in acetone or dioxan at a temperature from 0° C. to 10° C. for a period of from 5 minutes to 2 hours using, as oxidizing agent, chromic anhydride (especially Jones' reagent, which is a solution of chromic anhydride in 6-10 N sulphuric acid) or pyridinium chlorochromate. Alternatively, the reaction may preferably be carried out at a temperature of from −20° C. to +30° C. for a period which may vary from 1 minute to 96 hours using a combined oxidizing agent which consists of dimethyl sulphoxide, a carbodiimide (such as dicyclohexylcarbodiimide) and an acid (such as phosphoric acid, acetic acid, trifluoroacetic acid or dichloroacetic acid)-Moffatt oxidation.

After completion of the reaction, the desired product of formula (IX) can be recovered from the reaction mixture by conventional means. For example, excess oxidizing agent is decomposed and then the reaction mixture is diluted with a water-immiscible organic solvent (such as those exemplified in the previous step), washed with water and dried. The solvent is then distilled off and the resulting residue is purified by recrystallization, reprecipitation or column chromatography to give the desired compound of formula (IX).

Step 1(b)

This is the first step of an alternative route for preparing the compound of formula (IX). In this step, the compound of formula (II) is reacted with a hypohalogenous acid-producing reagent in the presence of a suitable solvent.

Suitable hypohalogenous acid-producing reagents include: a combination of water with a halogenating agent such as N-bromosuccinimide, N-chlorosuccinimide or N-bromoacetamide; and hypohalogenous acid salts, such as sodium hypochlorite or potassium hypochlorite. Preferred solvents for use in this reaction include mixtures of water with water-miscible organic solvents, such as dialkyl sulphoxides (e.g. dimethyl sulphoxide) or glycol ethers (e.g. 1,2-dimethoxyethane).

After completion of this reaction, the desired product of formula (VIIb) may be recovered from the reaction mixture by conventional means. For example, any excess of the hypohalogenous acid-producing reagent is decomposed and then the reaction mixture is diluted with a water-immiscible organic solvent, washed with water and dried, after which the solvent is distilled off. The resulting residue is purified by recrystallization, reprecipitation or column chromatography, giving the desired product.

Step 2(b)

In this reaction, a compound of formula (VIIIb) is prepared from the compound of formula (VIIb) by oxidization. The reaction conditions, reagents and subsequent treatment of the reaction mixture are as described for step 3(a).

Step 3(b)

In this step, the compound of formula (VIIIb) prepared in step 2(b) is converted to the desired compound of formula (IX) by reaction with a nucleophilic reagent of formula (XIV) or a reactive derivative thereof in the presence of a suitable solvent. Reaction conditions, reagents and subsequent treatment of the reaction mixture are as already described for step 2(a).

Step 1(c)

The compound of formula (VIIIb) may also be prepared in a single step from the compound of formula (VI), eliminating steps 1(b) and 2(b), by treating the compound of formula (VI) with silver chromate and a halogen (such as chlorine, bromine or iodine). This reaction is preferably carried out in an aprotic organic solvent (such as methylene chloride, chloroform, benzene or tetrahydrofuran) at a temperature from −30° C. to +50° C. After completion of the reaction, the desired compound of formula (VIIIb) may be recovered from the reaction mixture by conventional means. For example, the solid substance formed is filtered off and the filtrate is washed with sodium thiosulphate to remove excess halogen. After this, the filtrate is washed with water and dried and then the solvent is distilled off. The residue may be purified by recrystallization, reprecipitation or column chromatography to give the desired compound of formula (VIIIb) in a substantially pure form.

Step 4

In this step, the compound of formula (IX) is, if necessary, converted to the compound of formula (X) by converting a thio group represented by X' to a sulphinyl or sulphonyl group and/or removing the protecting group $R^7$ on the β-lactam nitrogen atom.

Removal of the protecting group $R^7$ may be carried out by conventional means. Where this protecting group is a trialkylsilyl group (e.g. t-butyldimethylsilyl), it can be removed by treating the compound with a hydrohalogenic acid (e.g. hydrochloric acid, hydrobromic acid or hydrofluoric acid) or with a fluoride anion-producing compound, such as a tetraalkylammonium fluoride potassium fluoride or sodium fluoride. Where the protecting group is a tetrahydropyranyl group, it can be removed by treating the compound with an aqueous mineral acid solution, e.g. dilute hydrochloric acid or dilute sulphuric acid.

This removal action is preferably carried out in the presence of a polar solvent, for example: a fatty acid dialkylamide, such as dimethylformamide or diethylacetamide; dimethyl sulphoxide; an aqueous alcohol, such as aqueous methanol or aqueous ethanol; or an aqueous ether, such as aqueous tetrahydrofuran or aqueous dioxan. The reaction is preferably carried out at a temperature of from −10° C. to +30° C., for a period which may vary from 10 minutes to 3 hours. After completion of the reaction, the desired product may be recovered from the reaction mixture by conventional means, for example by diluting the reaction mixture with a water-immiscible solvent, neutralizing it, washing it with water and drying it, after which the solvent is distilled off. The resulting residue may then be purified by recrystallization, reprecipitation or column chromatography.

Conversion of the thio group represented by X' to a sulphinyl group or sulphonyl group may, if necessary, be effected by treating the compound in which X' represents a thio group with an oxidizing agent. Conditions, reagents and subsequent treatment of the product are the same as those already described in connection with step 1(a).

Step 5

In this step, the compound of formula (X) prepared in Step 4 is reacted with a glyoxylic acid ester of formula (XV):

$$\text{OCH—COOR}^{3'} \tag{XV}$$

(wherein $R^{3'}$ is as defined above) or with a hemi-acetal derivative of this ester (XV).

Where a hemi-acetal derivative is used, it is preferably a hemi-acetal of the ester (XV) with a lower alkanol, such as methanol or ethanol. The reaction is preferably effected in the presence of a solvent, for example: a fatty acid dialkylamide, such as dimethylformamide or dimethylacetamide; or an aromatic hydrocarbon, such as benzene, toluene or xylene. The reaction temperature is not critical, but we preferably employ a temperature from 25° C. to the reflux temperature of the solvent. The reaction is normally and preferably carried out under a stream of an inert gas (e.g. nitrogen or argon) in order to prevent side reactions. The time required for the reaction will depend upon the reaction temperature and other factors, such as the nature of the solvent and of the reagents, but generally the reaction will be complete within a period of from 2 to 10 hours. Where the glyoxylic acid ester (XV) is employed in the form of a hydrate, the water produced by the reaction may, if necessary, be removed by azeotropic distillation or by means of a molecular sieve.

After completion of the reaction, the desired product of formula (XI) may be recovered from the reaction mixture by conventional means. For example, the organic solvent is first distilled from the reaction mixture, after which the residue is purified by recrystallization, reprecipitation or chromatography.

Step 6

In this step, the compound of formula (XI) prepared in Step 5 is halogenated, normally in the presence of a solvent, to give the compound of formula (XII).

There is no particular limitation on the nature of the halogenating agent employed in this step, provided that it is capable of halogenating hydroxy compounds without damaging other parts of the molecule. Examples of preferred halogenating agents include: phosphorus trihalides, such as phosphorus trichloride or phosphorus tribromide; phosphorus pentahalides, such as phosphorus pentachloride or phosphorus pentabromide; phosphorus oxyhalides, such as phosphorus oxychloride or phosphorus oxybromide; thionyl halides, such as thionyl chloride or thionyl bromide; and oxalyl halides, such as oxalyl chloride or oxalyl bromide.

The reaction is preferably carried out in the presence of an acid binding agent, which is normally an organic base, such as triethylamine, pyridine or 2,6-lutidine.

The nature of the solvent employed in this reaction is not critical, provided that it has no adverse effect upon the reaction. Preferred solvents are: ethers, such as diethyl ether, tetrahydrofuran or dioxan; or halogenated hydrocarbons, such as methylene chloride or chloroform. The reaction temperature may vary over a wide range, preferably from −40° C. to +40° C., and the reaction time will depend upon the nature of the halogenating agent and the reaction temperature, but will, in general, be within from 15 minutes to 5 hours.

After completion of the reaction, the compound of formula (XII) may be recovered from the reaction mixture by conventional means. For example, the reaction mixture is first diluted with an inert organic solvent and the precipitated hydrohalide of the organic base used as acid binding agent is filtered off. The solvent is then distilled from the resulting filtrate and the residue is purified by recrystallization or reprecipitation to give the desired compound. However, this separation and purification procedure is not necessary and, if desired, the residue obtained by simply distilling off, under reduced pressure, the halogenating agent and the organic solvent can be employed in Step 7 without further purification.

Step 7

In this step, the compound of formula (XII) prepared in Step 6 is reacted with a phosphine compound of formula (XVI):

$$P(R^5)_3 \qquad (XVI)$$

(wherein $R^5$ is as defined above) in a solvent in the presence of a base to give a phosphorus-ylide compound of formula (II).

This reaction is part of a so-called Wittig reaction and the phosphorus-ylide compound obtained is the starting material for the process of the present invention leading to the preparation of the compounds of formula (I).

The most preferred phosphine of formula (XVI) for employment in this reaction is triphenylphosphine. There is no particular limitation on the base and examples of bases which may be used include: organic bases, such as triethylamine, pyridine and 2,6-lutidine; and alkali metal carbonates, such as sodium carbonate or potassium carbonate. The nature of the solvent employed is also not critical, provided that it has no adverse effect upon the reaction. Suitable solvents include: ethers, such as tetrahydrofuran or dioxan; aromatic hydrocarbons, such as benzene, toluene or xylene; halogenated hydrocarbons, such as methylene chloride or chloroform; fatty acid dialkylamines, such as dimethylformamide or dimethylacetamide; and dimethyl sulphoxide. The reaction temperature is also not critical and may vary over a wide range, for example from −30° C. to +120° C. The time required for the reaction will depend mainly upon the reaction temperature but the reaction will usually be complete within from 0.5 to 10 hours. It is preferred to incorporate a catalytic amount of an antioxidant (such as hydroquinone) into the reaction mixture, if necessary, in order to prevent oxidation.

After completion of the reaction, the phosphorus-ylide compound (II) may be recovered from the reaction mixture by conventional means. A suitable recovery scheme comprises: diluting the reaction mixture with water; diluting the mixture with a water-immiscible organic solvent; separating the organic solvent layer and washing it with water; drying the organic solvent solution; and distilling off the solvent. The resulting residue may be purified by recrystallization, reprecipitation or column chromatography to give the desired phosphorus-ylide compound (II).

Step 8

In this step, the phosphorus-ylide compound of formula (II) is subjected to a ring-closure reaction.

This reaction is preferably carried out in the presence of an inert solvent or mixture of solvents, for example: an ether, such as tetrahydrofuran or dioxan; a halogenated hydrocarbon, such as methylene chloride or chloroform; or an aromatic hydrocarbon, such as benzene, toluene or xylene. The temperature to which the phosphorus-ylide compound is heated is preferably from 30° C. to 200° C. The time required for the reaction will depend mainly upon the reaction temperature, but is generally from 1 to 40 hours. The reaction is preferably carried out under a stream of an inert gas (such as argon or nitrogen) to prevent side reactions. Also, in order to prevent oxidation reactions, the heating is preferably carried out in the presence of a catalytic amount of an antioxidant such as hydroquinone.

This ring-closure reaction may occur in the course of Step 7, if the temperature at which that step is carried out is suitable; in that case, of course, a separate Step 8 may not be required.

After completion of the reaction, the desired compound of formula (III) may be recovered from the reaction mixture by conventional means, for example by distilling off the solvent and then purifying the resulting residue by recrystallization, reprecipitation or column chromatography.

Step 9

This step may or may not be necessary, but is designed to remove protecting groups (if any) and, if desired, to convert an amino group represented by $R^2$ in the product to a group of formula

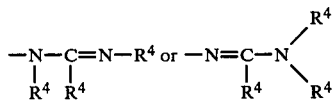

(in which $R^4$ is as defined above)

A carboxylic acid compound of formula (I) wherein $R^3$ represents a carboxy group may be obtained by removing the carboxy-protecting group forming part of the group $R^{3'}$ in the compound of formula (III). Removal of the protecting group may be carried out by conventional means which will, as is well-known in the art, vary according to the nature of the protecting group.

Where the protecting group is removable by reduction (for example if it is a halogenated alkyl group, aralkyl group or benzhydryl group), its removal may be effected simply by contacting the compound with a reducing agent, the nature of which will vary depending upon the nature of the protecting group to be removed. If the protecting group is a halogenated alkyl group (e.g. 2,2-dibromomethyl or 2,2,2-trichloroethyl), a preferred reducing agent is a combination of zinc with acetic acid. Where the protecting group is an aralkyl group (such as benzyl or p-nitrobenzyl) or a benzhydryl group, a preferred reducing agent is a combination of hydrogen with a suitable catalyst (such as palladium-on-carbon) or an alkali metal sulphide (such as sodium sulphide or potassium sulphide). Removal of the protecting group is preferably carried out in the presence of a solvent, the nature of which is not critical, provided that it does not adversely affect the reaction. Preferred solvents include: alcohols, such as methanol or ethanol; ethers, such as tetrahydrofuran or dioxan; fatty acids, such as acetic acid; and mixtures of water or of a phosphate buffer (pH value about 7.0) with these organic solvents. The reaction temperature will normally be within the range from 0° C. to about room temperature. The time required for the reaction will depend upon the nature of the starting material and of the reducing agent, but the reaction will generally be complete within from 5 minutes to 12 hours.

Where hydroxy groups, amino groups, hydroxyamino groups, aminooxy groups or guanidino groups represented by or included within the groups represented by $R^{1'}$ and/or $R^{2'}$ in the compound of formula (III) are protected by aralkyloxycarbonyl groups, then these protecting groups will be removed at the same time as the carboxy-protecting groups.

After completion of the reaction removing the carboxy-protecting group, the desired product can be recovered from the reaction mixture by conventional means. For example, insolubles precipitated in the reaction mixture are filtered off and the organic phase is washed with water, after which the solvent is distilled off. If necessary, the residue may then be purified by recrystallization, preparative thin layer chromatography or column chromatography. If the desired product of this step is soluble in water, insolubles are filtered off and, if necessary, the filtrate is concentrated under reduced pressure, after which the solution is subjected to column chromatography using a porous adsorbent resin (such as Diaion HP-20AG a product of Mitsubishi Chemical Industries, Limited). Fractions containing the desired product are then collected and lyophilized.

Where the group $R^{1'}$ in the compound of formula (III) includes a protected hydroxy group and/or the group $R^{2'}$ is or includes a protected hydroxy group, the protecting group is preferably an acyl group or a trialkylsilyl group.

Where the protected hydroxy group is a lower alkanoyloxy group (e.g. an acetoxy group), removal of the protecting group may be effected by treating the compound with a base in the presence of an aqueous solvent. There is no particular limitation on the nature of the solvent and any of those commonly used for hydrolysis reactions may be employed. Preferred solvents include water and mixtures of water with organic solvents, such as alcohols, (e.g. methanol, ethanol or propanol) or ethers (e.g. tetrahydrofuran or dioxan). There is also no particular limitation on the nature of the base, provided that it does not interfere with other parts of the compound, especially the β-lactam ring. Preferred bases are alkali metal carbonates, such as sodium carbonate or potassium carbonate. The reaction temperature is also not critical, although it is generally kept below room temperature (e.g. from 0° C. to room temperature) in order to control side reactions. The time required for the reaction will depend upon the nature of the starting materials and upon the reaction temperature, but it is generally from 1 to 6 hours.

If the protected hydroxy group is an aralkyloxycarbonyl group (e.g. benzyloxycarbonyloxy or p-nitrobenzyloxycarbonyloxy), removal of the protecting group may be carried out by contacting the compound with a reducing agent. Reducing agents and reaction conditions which may be used for this removal are the same as already described for the removal of aralkyl groups from protected carboxy groups represented by $R^{3'}$ and hence, provided that the protecting groups are chosen appropriately, the carboxy-protecting and hydroxy-protecting groups may be removed simultaneously.

Where the protected hydroxy group is a tri(lower alkyl)silyloxy group (e.g. t-butyldimethylsilyloxy), removal of the protecting group may be effected by treating the compound with tetrabutylammonium floride, normally in the presence of a solvent. There is no particular limitation on the nature of the solvent employed in this reaction, but preferred solvents are ethers, such as tetrahydrofuran or dioxan. The reaction is preferably carried out at about room temperature and will require a period of from 10 to 18 hours.

Where $R^{1'}$ in the compound of formula (III) includes a protected amino group and/or $R^{2'}$ is or includes a protected amino group, the protected groups are preferably substituted acetylamino or aralkyloxycarbonylamino groups.

Where the protected amino group is an acetylamino group (e.g. a phenylacetylamino or phenoxyacetylamino group), the protecting group may be removed by contacting the compound with an acylase.

This enzymatic reaction may be conducted according to the procedure described with respect to N-acyl-thienamycin in Japanese Patent Application Kokai No. 46890/79. The preferred acylase is penicillin amide hydrase, which is produced, for example, by *Escherichia coli*.

When the protected amino group is an aralkyloxycarbonylamino group (such as a benzyloxycarbonylamino or p-nitrobenzyloxycarbonylamino group), removal of the protecting group may be effected by contacting the compound with a reducing agent. The nature of the reducing agent employed and of the reaction conditions are the same as those already described in respect to the removal of aralkyl groups from protected carboxy groups $R^{3'}$ and, accordingly, such groups may be removed simultaneously with the removal of carboxy-protecting groups.

Where $R^{2'}$ in the compound of formula (III) is or includes a protected carboxy group, the protected carboxy group is preferably an alkoxycarbonyl group, an aralkyloxycarbonyl group or a benzhydryloxycarbonyl group.

Where the protected carboxy group is an alkoxycarbonyl group (e.g. methoxycarbonyl or ethoxycarbonyl) removal of the protecting group may be carried out using the same hydrolysis reaction with a base as described with respect to the conversion of lower alkanoyloxy groups to hydroxy groups for $R^{1'}$ and $R^{2'}$. Where the protected carboxy group is an aralkoxycarbonyl group (such as a benzyloxycarbonyl or p-nitrobenzyloxycarbonyl group) or a benzhydryloxycarbonyl group, removal of the protecting group may be carried out by means of the same reduction procedure as has already been described with respect to removal of aralkylcarboxy-protecting groups from the group $R^{3'}$.

Similarly, where $R^{2'}$ is or includes a protected hydrazino group, the protecting group is preferably an aralkyloxycarbonyl group and this may be removed by this same reduction procedure.

Where $R^{1'}$ in the compound of formula (III) is a protected mercapto group and/or $R^{2'}$ is or includes a protected mercapto group, the protecting group is preferably a lower alkanoyl group. The protecting group may be removed by the same hydrolysis reaction using a base as has already been described with respect to the conversion of lower alkanoyloxy (protected hydroxy) groups to free hydroxy groups for $R^{1'}$ and $R^{2'}$.

Where $R^{2'}$ is a protected hydroxyamino group, the protecting group is preferably a lower alkanoyl group or an aralkyloxycarbonyl group. Lower alkanoyl protecting group may be removed by this same hydrolysis procedure.

Where the protected hydroxyamino group is an aralkyloxycarbonyloxyamino group (e.g. benzyloxycarbonyloxyamino or p-nitrobenzyloxycarbonyloxyamino), the protecting group may be removed by the same reduction procedure as has already been described for the removal of aralkyl groups from protected carboxy groups $R^{3'}$.

Where $R^{2'}$ is protected aminooxy group, the protecting group is preferably an aralkyloxycarbonyl group and this may also be removed by the same reduction procedure as has been described for the removal of aralkyl groups from protected carboxy groups $R^{3'}$.

Where $R^{2'}$ in the compounds of formula (III) represents a protected guanidino group, the protecting group is preferably an aralkyloxycarbonyl group and this may be removed by the same reduction procedure as has already been described for the removal of aralkyl groups from protected carboxy groups $R^{3'}$.

Compounds of formula (I) in which $R^2$ represents a group of formula

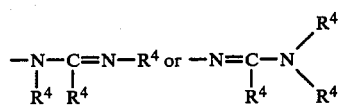

can be prepared by reacting the corresponding compound of formula (III) or (I) in which $R^2$ or $R^{2'}$ is an amino group or a lower alkyl-substituted amino group with an imide ester of formula (IV):

or of formula (V):

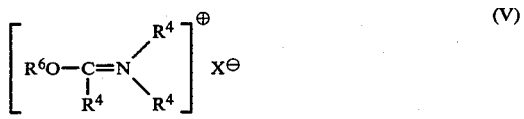

(in which $R^4$, $R^6$ and $X^-$ are as defined above).

This reaction may be carried out by contacting the compound of formula (I) or (III) in which $R^2$ or $R^{2'}$ represents an amino group or a lower alkyl-substituted amino group with the imide ester (IV) or (V) under alkaline conditions, preferably at a pH of from 8 to 9. There is no limitation on the nature of the alkaline reagent employed to achieve these alkaline conditions, but preferred reagents are: alkali metal hydroxides, such as sodium hydroxide or potassium hydroxide; alkaline earth metal hydroxides, such as calcium hydroxide or barium hydroxide; and alkali metal carbonates, such as sodium carbonate or potassium carbonate. The reaction is preferably carried out in an aqueous solvent. Preferred solvents are water and mixtures of water with organic solvents such as alcohols (e.g. methanol, ethanol or propanol), ethers (e.g. tetrahydrofuran or dioxan), fatty acid dialkylamides (e.g. dimethylformamide or dimethylacetamide) or nitriles (e.g. acetonitrile). The reaction is preferably carried out at a relatively low temperature, e.g. from 0° C. to room temperature. The time required for the reaction will depend upon the nature of the starting materials and on the reaction temperature, but it is generally from 5 minutes to 1 hour.

After completion of the reaction, the desired product may be recovered from the reaction mixture by conventional means. One such recovery sequence comprises: neutralizing the reaction mixture; subjecting it to column chromatography using a porous adsorbant resin (such as Diaion HP-20AG, a product of Mitsubishi Chemical Industries, Limited); collecting the fractions containing the desired product; and lyophilizing these fractions to give the product. After this, the product may be further purified by, for example, recrystallization or reprecipitation.

The compound thus obtained may, if necessary, be converted to the carboxylic acid derivative by removing the carboxy-protecting group according to conventional means.

When the groups X' and X in the compounds of the above reaction scheme represent thio groups, they may be converted to sulphinyl groups or sulphonyl groups by oxidation reaction, the reaction conditions and subsequent treatment being as described in Step 1(a).

If the phosphorus-ylide compound of formula (II) is subjected to an oxidation reaction, it is necessary to protect the phosphorus-ylide bond by protonation in the presence of more than 1 mole of a mineral acid (such as hydrochloric acid or hydrobromic acid) or of trifluoroacetic acid per mole of phosphorus-ylide compound.

The compounds of formula (I) and their salts have potent antibacterial activities. Their activities have been tested by an agar plate dilution method and the results show that they have antibacterial activity against a wide range of pathogenic microorganisms, including both gram- postive microorganisms (such as *Staphylococcus aureus* and *Bacillus subtilis*) and gram-negative microorganisms (such as *Escherichia coli, Shigella dysenteriae* Shiga, *Klebsiella pneumoniae,* slime mould and *Pseudomonas aeruginosa*). The minimal inhibitory concentrations of a representative compound of the invention, Compound No. 10, against a variety of microorganisms are shown in the following Table.

TABLE

| Microorganism | MIC μg/l |
|---|---|
| *Bacillus subtilis* | 0.05 |
| *Staphylococcus aureus* | ≧0.01 |
| *Staphylococcus epidermidis* | 0.01 |

TABLE-continued

| Microorganism | MIC μg/l |
|---|---|
| *Escherichia coli* | 0.20 |
| *Micro-coccus luteus* | ≧0.006 |
| *Klebsiella pneumoniae* | 0.20 |
| *Proteus mirabilis* | 0.78 |
| *Proteus vulgaris* | 0.39 |
| *Serratia marcescens* | 0.78 |
| *Enterobacter cloacae* | 0.78 |
| *Pseudomonas aeruginosa* | 3.13 |

Accordingly, the compounds of the invention may be used for the treatment of diseases caused by these pathogenic microorganisms. For this purpose, the compounds of the invention may be administered orally (e.g. in the form of tablets, capsules, granules, powers or syrups) or parenterally (e.g. by intravenous injection or intramuscular injection). The dose will vary depending upon the age, body weight and condition of the patient and on the route and type of administration but, in general, the compounds of the invention may be administered in a daily dose of from 250 to 3,000 mg for adults, either as a single dose or as divided doses.

The invention is further illustrated by the following Examples, which describe the preparation of various compounds of the invention.

EXAMPLE 1

Sodium 3-ethylthiomethyl-7-oxo-1-azabicyclo[3.2.0]hept-2-ene-2-carboxylate (Sodium salt of Compound No. 176)

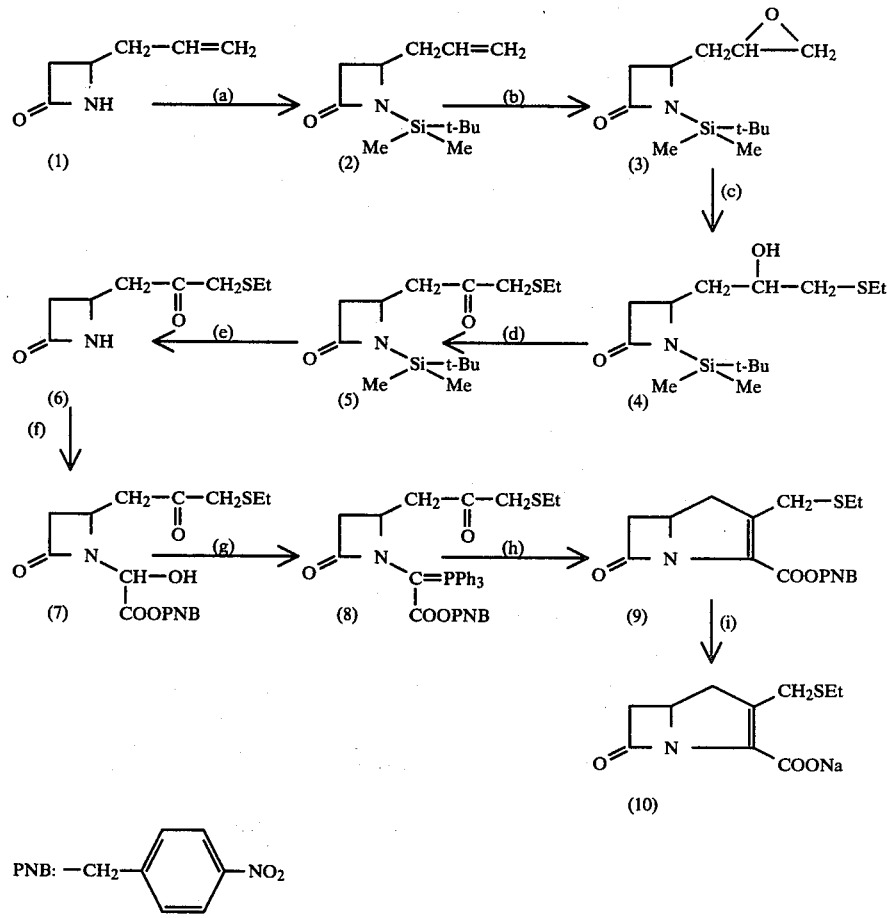

Me: methyl
Et: ethyl
t-Bu: t-butyl
Ph: phenyl (a) 4-Allyl-1-t-butyldimethylsilyl-azetidin-2-one 1.98 g. of 4-allyl-azetidin-2-one (1) were dissolved in 15 ml. of anhydrous N,N-dimethylformamide. To the solution were added successively 3.35 g. of t-butyldimethylsilyl chloride and 3.25 ml. of triethylamine, with ice cooling. The mixture was stirred, with ice cooling, for 2 hours and then diluted with ethyl acetate, washed five times with water and dried over magnesium sulphate. The solvent was distilled off and the resulting residue was purified by silica gel chromatography eluted with a 5:1 by volume mixture of benzene and ethyl acetate, to give 3.45 g. (yield 85.6%) of the desired silyl compound (2).

Nuclear Magnetic Resonance Spectrum (CDCl$_3$)δ ppm: 0.25 (6H, singlet); 0.95 (9H, singlet); 1.83–2.65 (2H, multiplet); 2.56 (1H, double doublet, J=15 and 3.5 Hz); 3.08 (1H, double doublet, J=15 and 6 Hz); 3.38–3.73 (1H, multiplet); 4.77–4.97 (1H, multiplet); 5.08 (1H, singlet); 5.32–5.97 (1H, multiplet).

(b) 1-t-Butyldimethylsilyl-4-(2,3-epoxypropyl)-azetidin-2-one 3.4 g. of the silyl compound (2) were dissolved in 70 ml. of chloroform, and 5.30 g. of m-chloroperbenzoic acid were added thereto at room temperature. After the mixture had produced a uniform solution, it was left to stand for 48 hours. The solution was then diluted with ethyl acetate, washed twice with an aqueous solution of sodium hydrogen sulphite (to remove excess peroxy acid), washed successively with an aqueous solution of sodium chloride, an aqueous solution of sodium bicarbonate and an aqueous solution of sodium chloride, and then dried over magnesium sulphate. The solvent was distilled off and the resulting mixture was purified by silica gel chromatography eluted with a 2:1 by volume mixture of benzene and ethyl acetate, to give 3.12 g. (yield 84.6%) of the desired epoxy compound (3).

Nuclear Magnetic Resonance Spectrum (CDCl$_3$)δ ppm: 0.23 (6H, singlet); 0.95 (9H, singlet); 1.63–2.93 (6H, multiplet); 3.22 (1H, double doublet, J=16 and 6 Hz); 3.53–3.93 (1H, multiplet).

(c) 1-t-Butyldimethylsilyl-4-(3-ethylthio-2-hydroxy)-propylazetidin-2-one 2.02 g. of the epoxy compound (3) were dissolved in 100 ml. of anhydrous tetrahydrofuran. To the solution were added slowly 1.24 ml. of ethyl mercaptan and 5.2 ml. of n-butyllithium (1 ml.=1.62 mmole), with ice cooling and stirring. Stirring was continued, with ice cooling, for 2 hours. The mixture was then diluted with ethyl acetate and, after the addition of 0.6 ml. of acetic acid, washed with water. The organic layer was successively washed with an aqueous solution of sodium chloride, an aqueous solution of sodium bicarbonate and an aqueous solution of sodium chloride, and dried over magnesium sulphate. The solvent was then distilled off under reduced pressure and the resulting residue was purified by silica gel chromatography eluted with a 1:1 by volume mixture of benzene and ethyl acetate, to afford 2.20 g. (yield 86.5%) of the desired hydroxy compound (4). This hydroxy compound (4) is a mixture of optical isomers, because there exist two optically active points in its molecule.

(d) 1-t-Butyldimethylsilyl-4-ethylthiomethylcarbonylmethylazetidin-2-one 1.75 g. of the hydroxy compound (4) were dissolved in 20 ml of anhydrous dimethyl sulphoxide. After addition of 4.19 g. of dicyclohexylcarbodiimide, the mixture was stirred at room temperature and five drops of dichloroacetic acid were added thereto. The mixture was then left to stand at room temperature for 10 minutes, after which it was diluted with ethyl acetate, washed five times with water and successively with an aqueous solution of sodium bicarbonate and an aqueous solution of sodium chloride, and then dried over magnesium sulphate. The solvent was distilled off under reduced pressure and the resulting residue was purified by silica gel chromatography eluted with a 5:1 by volume mixture of benzene and ethyl acetate, to give 1.23 g. (yield 70.9%) of the desired keto compound (5).

Nuclear Magnetic Resonance Spectrum (CDCl$_3$)δ ppm: 0.25 (6H, singlet); 0.92 (9H, singlet); 1.18 (3H, triplet, J=8 Hz); 2.45 (2H, quartet, J=8 Hz); 2.38–3.43 (6H, multiplet); 3.68–4.15 (1H, multiplet).

(e) 4-Ethylthiomethylcarbonylmethyl-azetidin-2-one 10 ml. of a solution of 0.25 N hydrochloric acid in methanol were added to 1.22 g. of the keto compound (5), and the mixture was stirred at room temperature for 3.5 hours. After completion of the reaction, the reaction mixture was poured into an aqueous solution of sodium bicarbonate and extracted three times with ethyl acetate. The combined extracts were dried over magnesium sulphate and the solvent was distilled off under reduced pressure. The resulting residue was purified by silica gel chromatography eluted with ethyl acetate, to afford 558 mg. (yield 73.6%) of the desired desilyl compound (6).

Nuclear Magnetic Resonance Spectrum (CDCl$_3$)δ ppm: 1.18 (3H, triplet, J=7.5 Hz); 2.40 (2H, quartet, J=7.5 Hz); 2.32–3.13 (6H, multiplet); 3.58–3.93 (1H, multiplet); 6.85 (1H, broad singlet).

(f) 4-Ethylthiomethylcarbonylmethyl-1-(1-hydroxy-1-p-nitrobenzyloxycarbonylmethyl)-azetidin-2-one 116 mg. of p-nitrobenzyl glyoxylate were dissolved in 40 ml. of benzene. The solution was then dehydrated for 3 hours using a Dien Stark apparatus. The resulting mixture was cooled to room temperature and 52 mg. of the desilyl azetidine compound (6) were added thereto. The mixture was then refluxed for 8 hours to dehydrate it. After completion of the reaction, the solvent was distilled off and the resulting residue was purified by preparative thin layer chromatography eluted with a 10:10:1 by volume mixture of diethyl ether, diisopropyl ether and isopropanol, to give 63.3. mg. (yield 57.5%) of the desired hydroxy compound (7).

(g) 4-Ethylthiomethylcarbonylmethyl-1-(1-p-nitrobenzyloxycarbonyl-1-triphenylphosphoranylidenemethyl)-azetidin-2-one 523 mg. of the hydroxy compound (7) were dissolved in 40 ml. of anhydrous tetrahydrofuran. 0.46 ml. of 2,6-lutidine and 0.29 ml. of thionyl chloride were added to the mixture under an argon atmosphere at −20° C. The mixture was then stirred at −10° to −20° C. for 45 minutes. After completion of the reaction, the solvent was distilled off under reduced pressure to give the crude chloro compound. This chloro compound was dissolved in 40 ml. of anhydrous tetrahydrofuran, and 702 mg. of triphenylphosphine and 0.31 ml. of 2,6-lutidine were added thereto. The mixture was stirred at 55°–60° C. for 20 hours. After dilution with ethyl acetate, the mixture was twice washed with water and then dried over magnesium sulphate. The solvent was distilled off and the resulting crude product was purified by preparative thin layer chromatography eluted with a 2:1 by volume mixture of benzene and acetone, to afford 218 mg. (yield 25.8%) of the desired phosphoran compound (8).

(h) p-Nitrobenzyl 3-ethylthiomethyl-7-oxo-1-azabicyclo[3.2.0]hept-2-ene-2-carboxylate A catalytic amount of hydroquinone was added to a solution of 121 mg. of the phosphoran compound (8) in 10 ml. of xylene. The mixture was refluxed on an oil bath at a bath temperature of 147° C. for 1 hour, whilst argon gas was passed into the mixture. The solvent was distilled off under reduced pressure and the residue was purifed by silica gel chromatography eluted with a 5:1 by volume mixture of benzene and ethyl acetate, to give 8.2 mg. (yield 11.9%) of the desired azabicycloheptene compound (9).

Ultraviolet Absorption Spectrum $\lambda_{max}$:276 nm.

Nuclear Magnetic Resonance Spectrum (CDCl$_3$) δppm: 1.20 (3H, triplet, J=7 Hz, S—CH$_2$—CH$_3$); 2.46 (2H, quartet, J=7 Hz, —S—CH$_2$CH$_3$); 2.73–3.83 (6H, multiplet, C$_4$—C$\underline{H}_2$, C$_6$—C$\underline{H}_2$, S—C$\underline{H}_2$—C=); 3.88–4.50 (1H, multiplet, C$_5$—H): 5.28 and 5.50 (2H, AB-quartet, J=14 Hz, benzyl CH$_2$); 7.70 (2H, doublet, J=8.5 Hz, PhNO$_2$); 8.30 (2H, doublet, J=8.5 Hz, PhNO$_2$).

(i) Sodium 3-ethylthiomethyl-7-oxo-1-azabicyclo[3.2.0]hept-2-ene-2-carboxylate (Sodium salt of Compound No. 176)

8.2 mg. of the azabicycloheptene compound (9) were dissolved in 2 ml. of anhydrous tetrahydrofuran. After the addition of 2 ml. of a pH 6.98 phosphate buffer, 27.2 mg. of 10% w/w palladium on carbon were added to the mixture and catalytic reduction was effected in a hydrogen atmosphere. The mixture was stirred for 2 hours, after which insolubles were filtered off and the resulting filtrate was washed twice, each time with 4 ml. of ethyl acetate, to give a phosphate buffer solution containing the desired compound (10) (i.e. the sodium salt of Compound No. 176). Ultraviolet Absorption Spectrum $\lambda_{max}$:267 nm.

EXAMPLE 2

Sodium (5R,6S)-3-(2-Ethoxyethylthiomethyl)-6-[1-(S)-hydroxyethyl]-7-oxo-1-azabicyclo[3.2.0]hept-2-ene-2-carboxylate (Sodium salt of Compound No. 175)

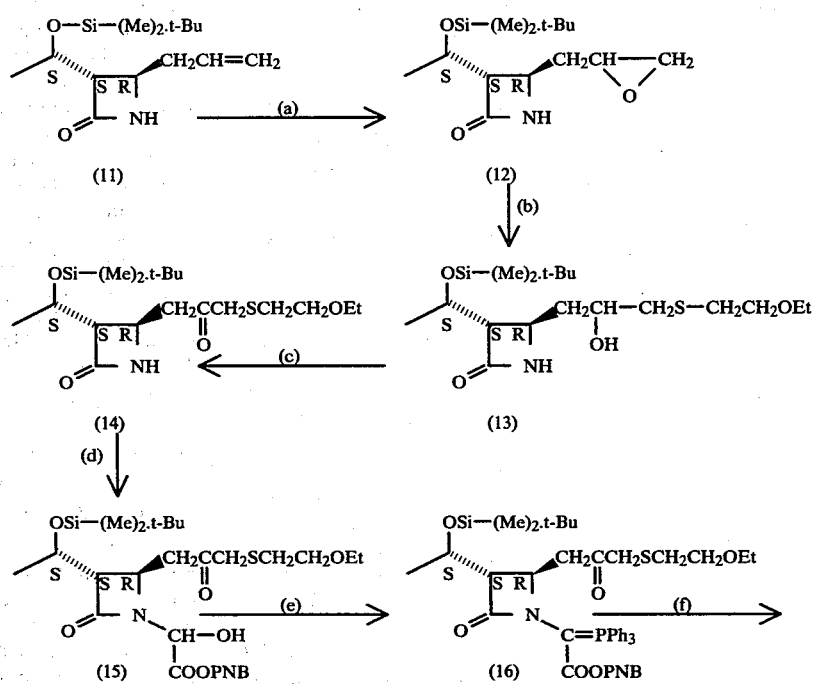

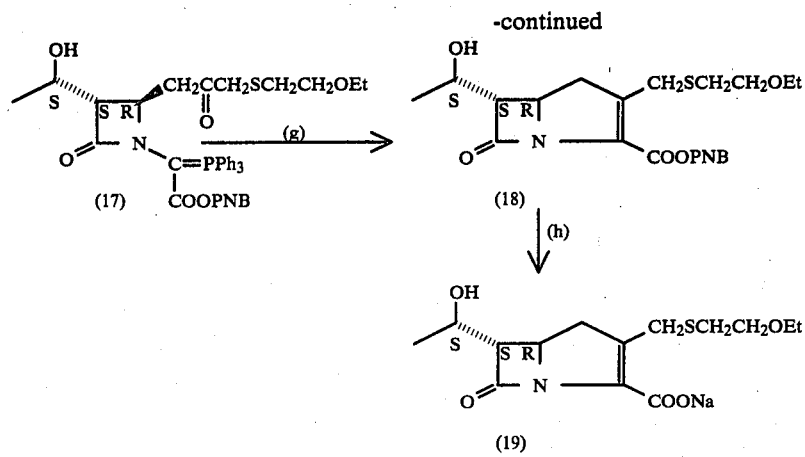

(a) (3S,4R)-3-[1-(S)-t-Butyldimethylsilyloxyethyl]-4-(2,3-epoxypropyl)-azetidin-2-one m-Chloroperbenzoic acid (954 mg., 5.53 mmole) was added to a solution of (3S, 4R)-4-allyl-3-[1-(S)-t-butyldimethylsilyloxyethyl]azetidin-2-one (11) (826 mg., 3.07 mmole) in 30 ml. of chloroform. The mixture was left to stand at room temperature for 15 hours and then diluted with ethyl acetate, washed successively with a saturated aqueous solution of sodium hydrogen sulphite (3 times), an aqueous solution of sodium chloride (1 time), an aqueous solution of sodium bicarbonate (2 times) and an aqueous solution of sodium chloride (2 times). It was then dried over sodium sulphate. The solvent was distilled off and the resulting residue was purified by rapid chromatography through 50 g. of silica gel eluted with a 3:2 by volume mixture of benzene and ethyl acetate, to afford 650 mg. (yield 74%) of the desired epoxyazetidine (12) as an oil.

Nuclear Magnetic Resonance Spectrum (CDCl$_3$) δppm: 0.10 [6H, singlet, OSi(Me)$_2$]; 0.85 (9H, singlet, t-Bu); 1.21 (3H, doublet, J=6.5 Hz, C$\underline{H}_3$CH.OSi); 1.5–3.0 (5H, multiplet, epoxypropyl); 2.88 (1H, multiplet, 3H); 3.52 (1H, multiplet, 4—CH); 4.00 (1H, multiplet, CH$_3$C$\underline{H}$.OSi); 6.82 (1H, doublet, J=4.5 Hz, NH).

(b) (3S,4R)-3-[1-(S)-t-Butyldimethylsilyloxyethyl]-4-[3-(2-ethoxyethyl)thio-2-hydroxypropyl]-azetidin-2-one To a solution of the epoxyazetidine (12) (591 mg., 2.07 mmole) in 12 ml. of dry tetrahydrofuran were added, with ice cooling, 0.264 g. (2.48 mmole) of 2-ethoxyethanethiol and then 1.5 ml. (2.48 mmole) of n-butyllithium in hexane, after which the mixture was stirred, with ice cooling, for 2 hours. To the reaction mixture were then added 0.3 ml. of acetic acid, ethyl acetate and water, and the organic layer was separated and successively washed with an aqueous solution of sodium chloride, an aqueous solution of sodium bicarbonate and an aqueous solution of sodium chloride; it was then dried over sodium sulphate. The solvent was distilled off and the resulting residue was purified by rapid chromatography through 35 g. of silica gel eluted with a 2:3 by volume mixture of benzene and ethyl acetate, to give 730 mg., (yield 90.4%) of the desired product (13) as an oil.

Nuclear Magnetic Resonance Spectrum (CDCl$_3$) δppm: 0.08 [6H, singlet, Si(CH$_3$)$_2$]; 0.84 (9H, singlet, t-Bu); 1.14 (3H, triplet, J=7.0 Hz, —OCH$_2$C$\underline{H}_3$); 1.20 (3H, doublet, J=6.5 Hz, C$\underline{H}_3$CH.OSi);

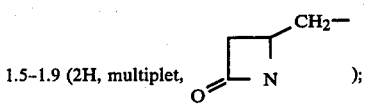

1.5–1.9 (2H, multiplet, 3.2–3.9 [7H, multiplet, CH$_2$OCH$_2$, —CH$_2$C$\underline{H}$OH, CH$_3$C$\underline{H}$(OSi)—]; 3.9–4.3 (1H, multiplet, 4—CH); 6.70 (1H, doublet, J=6.5 Hz, NH).

(c) (3S, 4R)-3-[1-(S)-t-Butyldimethylsilyloxyethyl]-4-(2-ethoxyethylthio)methylcarbonylmethyl-azetidin-2-one To a solution of 720 mg. (1.84 mmole) of the ethoxyethylthioazetidinone (13) in 16 ml. of dimethyl sulphoxide were added dicyclohexylcarbodiimide (1.33 g., 6.44 mmole) and dichloroacetic acid (0.16 ml.), after which the mixture was stirred at room temperature for 30 minutes. The reaction mixture was then diluted with ethyl acetate, washed successively with water, an aqueous solution of sodium bicarbonate and an aqueous solution of sodium chloride and dried over sodium sulphate. The solvent was then distilled off and the resulting residue was dissolved in 13 ml. of ethyl acetate. The solution was left to stand under ice cooling and insolubles were removed. The solubles in ethyl acetate were purified by rapid chromatography through 75 g. of silica gel eluted with a 1:1 by volume mixture of benzene and ethyl acetate, to give 560 mg. (yield 78.2%) of the desired product (14) as an oil.

Nuclear Magnetic Resonance Spectrum (CDCl$_3$) δppm: 0.1 [6H, singlet, Si(Me)$_2$]; 0.85 (9H, singlet, t-Bu); 1.12 (3H, triplet, J=6.5 Hz, —OCH$_2$C$\underline{H}_3$); 1.23 [3H, doublet, J=6.2 Hz, C$\underline{H}_3$CH(OSi)—]; 2.60 (2H, triplet, J=6.5 Hz, —CH$_2$SC$\underline{H}_2$CH$_2$); 3.25 (2H, singlet, —C$\underline{H}_2$SCH$_2$CH$_2$); 6.55 (1H, broad singlet, NH).

(d) (3S, 4R)-3-[1-(S)-t-Butyldimethylsilyloxyethyl]-4-(2-ethoxyethylthio)methylcarbonylmethyl-1-(1-hydroxy-1-p-nitrobenzyloxycarbonylmethyl)-azetidin-2-one p-Nitrobenzyl glyoxylate hydrate (715 mg., 3.146 mmole) was dehydrated in 350 ml. of benzene in a vessel equipped with a dehydrater, and then the mixture was concentrated to a volume of about 30 ml., and the ethoxyethylthioazetidinone (14) prepared in step (c) was added thereto. The mixture was refluxed for 4 hours, after which benzene was distilled off from the mixture and the resulting residue was purified by silica gel preparative thin layer chromatography (20×40 cm.×2 mm.) eluted with a 3:7 by volume mixture of benzene and ethyl acetate, to give 573 mg. (yield 61%) of the desired alcohol (15) as an oil.

Nuclear Magnetic Resonance Spectrum (CDCl₃) δppm: 0.05 [6H, singlet, Si(Me)₂]; 0.76 (9H, singlet, t-Bu); 1.05 (3H, triplet, J=6.5 Hz, CH₂C$\underline{H}$₃);
1.13 (3H, doublet, J=6.0 Hz, C$\underline{H}$₃CH.OSi); 2.55 (2H, triplet, J=6.0 Hz, CH₂SC$\underline{H}$₂CH₂); 3.18 (2H, singlet, CH₂SC$\underline{H}$₂CH₂); 5.20 (2H, singlet, —C$\underline{H}$₂.C₆H₄); 7.50 (2H, doublet, J=8.6 Hz, —C₆$\underline{H}$₄—NO₂); 8.16 (2H, doublet, J=8.5 Hz, —C₆$\underline{H}$₄—NO₂).

(e) (3S, 4R)-3-[1-(S)-t-Butyldimethylsilyloxyethyl]-4-(2-ethoxyethylthio)methylcarbonylmethyl-1-(1-p-nitrobenzyloxycarbonyl-1-triphenylphosphoranylidenemethyl)-azetidin-2-one To a solution of 570 mg. (0.952 mmole) of the alcohol (15) in 30 ml. of dry tetrahydrofuran were added 2,6-lutidine (306 mg., 2.856 mmole) and thionyl chloride (340 mg., 2.856 mmole) at −15°±5° C. under a stream of argon gas, and the mixture was stirred at −15°±5° C. for 20 minutes. The lutidine and tetrahydrofuran were distilled off under reduced pressure and to the resulting residue were added dry tetrahydrofuran (20 ml.), triphenylphosphine (499 mg., 1.904 mmole) and 2,6-lutidine (204 mg., 1.904 mmole) and the resulting mixture was stirred at 55° C. overnight. The reaction mixture was then diluted with ethyl acetate, washed with an aqueous solution of sodium chloride and dried over sodium sulphate. The solvent was distilled off and the resulting residue was purified by rapid chromatography through 100 g. of silica gel eluted with a 7:3 by volume mixture of benzene and ethyl acetate, to afford 239 mg. (yield 30%) of the desired triphenylphosphoran (16) as an oil.

(f) (3S, 4R)-4-(2-Ethoxyethylthio)methylcarbonylmethyl-3-[1-(S)-hydroxyethyl]-1-(1-p-nitrobenzyloxycarbonyl-1-triphenylphosphoranylidenemethyl)-azetidin-2-one To a solution of 100 mg. of the triphenylphosphoran (16) in 15 ml. of methanol was added 10% hydrochloric acid, with ice cooling; the mixture was then stirred, with ice cooling, for 30 minutes and then at room temperature for 40 minutes. 50 ml. of a saturated aqueous solution of sodium bicarbonate were added to the reaction mixture, with ice cooling. The mixture was then extracted with ethyl acetate, washed with an aqueous solution of sodium chloride and dried over sodium sulphate. The solvent was distilled off and the resulting residue was purified by rapid chromatography through 5 g. of silica gel eluted with ethyl acetate, to give 85 mg.

(yield 98.4%) of the desired hydroxyethylazetidinone (17) as an oil.

(g) p-Nitrobenzyl (5R, 6S)-3-(2-ethoxyethylthio)methyl-6-[1-(S)-hydroxyethyl]-7-oxo-1-azabicyclo[3.2.0]hept-2-ene-2-carboxylate Water was removed from 50 ml. of xylene in a vessel equipped with a dehydrater and then the xylene was concentrated to 35 ml. A catalytic amount of hydroquinone and 75 mg. of the ethoxyethylazetidinone (17) were then added and the mixture was refluxed for 40 minutes. The xylene was distilled off under reduced pressure and the resulting residue was purified by rapid chromatography through 13 g. of silica gel eluted with a 1:1 by volume mixture of benzene and ethyl acetate, to afford 24 mg. (yield 51.7%) of the desired azabicycloheptene (18).

Ultraviolet Absorption Spectrum (methylene chloride) λ$_{max}$: 270 nm.

Nuclear Magnetic Resonance Spectrum (CDCl₃) δppm: 1.04 (3H, doublet, J=6.5 Hz, CH₃CHOH); 1.23 (3H, triplet, J=7.5 Hz, OCH₂CH₃); 2.58 (2H, triplet, J=7.0 Hz, CH₂SCH₂CH₂—); 5.16 and 5.48 (2H, AB-quartet, J=14 Hz, Benzylic CH₂); 7.62 (2H, doublet, J=9.0 Hz, —C₆H₄—NO₂); 8.22 (2H, doublet, J=9.0 Hz, —C₆H₄—NO₂); 2.8–4.4 (12H, multiplet, miscellaneous).

Infrared Absorption Spectrum (CHCl₃) cm⁻¹: 3400, 1780, 1725.

(h) Sodium (5R, 6S)-3-(2-ethoxyethylthiomethyl)-6-[1-(S)-hydroxyethyl]-7-oxo-1-azabicyclo[3.2.0]hept-2-ene-2-carboxylate (sodium salt of Compound No. 175)

To a solution of 37 mg. of the p-nitrobenzyl ester (18) in 2.8 mg. of tetrahydrofuran were added 2.8 ml. of phosphate buffer (pH 7.1) and 10% palladium on carbon (80 mg.). The mixture was stirred under a stream of hydrogen for 3 hours. The palladium on carbon was then removed from the mixture, and the remaining solution was washed with ethyl acetate. The aqueous layer was concentrated to one-fourth of its original volume by evaporation under reduced pressure. The concentrate was purified using HP-20AG-chromatography (10 ml. capacity; solvent 5% aqueous acetone) to afford 8 mg. (from the 5% acetone fraction) and 3 mg. (from the water fraction) of the desired product (19). Yield was 29%.

Nuclear Magnetic Resonance Spectrum (D₂O) δppm: 1.00 (3H, triplet, J=6.0 Hz, —OCH₂C$\underline{H}$₃); 1.10 (3H, doublet, J=6.5 Hz, C$\underline{H}$₃CHOH); 2.3–4.3 (13H, multiplet).

EXAMPLE 3

(5R,6S)-3-(2-Aminoethylthiomethyl)-6-[1-(R)-hydroxyethyl]-7-oxo-1-azabicyclo[3.2.0]hept-2-ene-2-carboxylic acid (Compound No. 10)

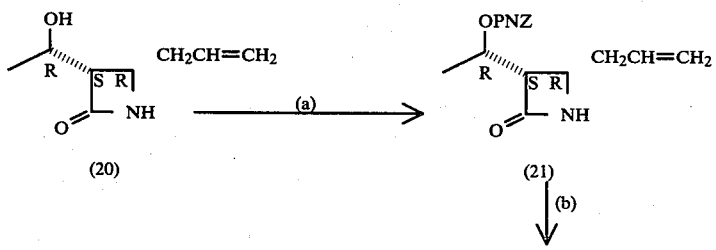

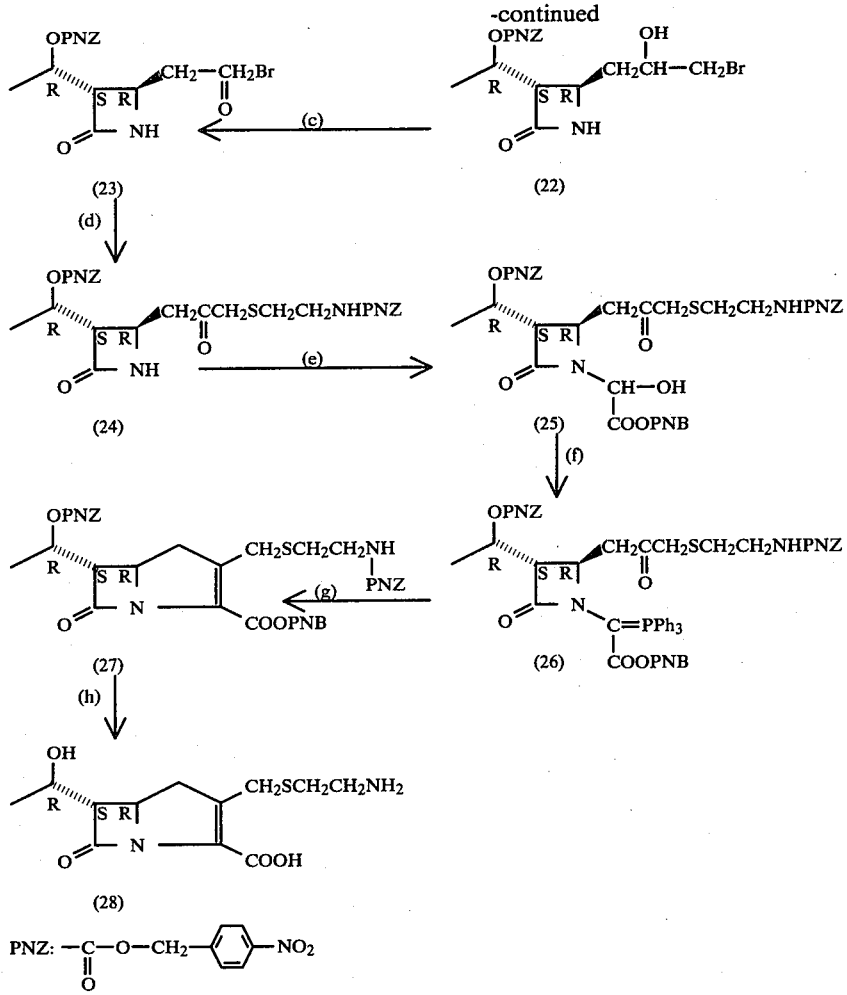

PNZ: —C(=O)—O—CH₂—C₆H₄—NO₂

(a) (3S, 4R)-4-Allyl-3-[1-(R)-p-nitrobenzyloxycarbonyloxyethyl]-azetidin-2-one

To a solution of (3S, 4R)-4-allyl-3-[1-(R)-hydroxyethyl]-azetidin-2-one (20) (592 mg., 3.815 mmole) in dry methylene chloride (10 ml.) was added dimethylaminopyridine (932 mg., 7.63 mmole), with ice cooling. To the mixture was then added very slowly (over 6 hours) a solution of p-nitrobenzyloxycarbonyl chloride (4.11 g.,19.08 mmole) in dry methylene chloride at room temperature. After stirring for 1 hour, the reaction mixture was diluted with 600 ml. of ethyl acetate, washed successively with an aqueous solution of sodium chloride, a 5% w/v aqueous solution of copper sulphate, an aqueous solution of sodium bicarbonate and an aqueous solution of sodium chloride, after which it was dried over sodium sulphate. The solvent was distilled off and the resulting residue was purified by silica gel column chromatography through 60 g. of silica gel, to give 776 mg. (yield 60.9%) of the desired product (21) as an oil from a fraction eluted with a 9:1 by volume mixture of benzene and ethyl acetate.

Nuclear Magnetic Resonance Spectrum (CDCl₃) δppm: 1.35 (3H, doublet, J=6.0 Hz, C$\underline{H}$₃CH.OSi); 2.26 (2H, triplet, J=6.5 Hz, —C$\underline{H}$₂CH=CH₂); 2.86 (1H, double doublet, J=7.0 and 2.0 Hz, 3—CH); 3.50 (1H, triplet, doublet, J=6.5 and 2.0 Hz, 4—CH); 5.17 (2H, singlet, —OC$\underline{H}$₂—C₆H₄—NO₂); 6.44 (1H, broad singlet, NH); 7.50 (2H, doublet, J=9.0 Hz, —C₆H₄—NO₂); 8.20 (2H, doublet, J=9.0 Hz, —C₆H₄—NO₂).

(b) (3S, 4R)-4-(3-Bromo-2-hydroxypropyl)-3-[1-(R)-p-nitrobenzyloxycarbonyloxyethyl]-azetidin-2-one To a solution of 4-allylazetidin-2-one (21) (0.755 g.) in dimethyl sulphoxide (10 ml.) were added N-bromosuccinimide (0.644 g.) and water (0.102 ml.) at room temperature, and the resulting mixture was stirred for 1.5 hours. The reaction mixture was then diluted with chloroform (200 ml.), washed successively with water, an aqueous solution of sodium hydrogen sulphite, water and an aqueous solution of sodium chloride, after which it was dried over sodium sulphate. The solvent was distilled off under reduced pressure and the resulting oily residue was subjected to rapid chromatography using silica gel and eluted with a 1:4 by volume mixture of benzene and ethyl acetate, to give 0.65 g. (yield 48%) of hydroxyazetidin-2-one (22).

Nuclear Magnetic Resonance Spectrum (CDCl₃) δppm: 1.37 (3H, doublet, J=6.5 Hz, CH₃); 1.6–2.1 (2H, multiplet, —C$\underline{H}$₂CHOHCH₂Br); 3.5–4.1 (2H, multiplet, 4—CH,—CH₂C$\underline{H}$OHCH₂Br); 5.22 (2H, singlet, —C$\underline{H}$₂—C₆H₄—NO₂); 6.87 (1H, doublet, J=8.0 Hz, NH);

7.55 (2H, doublet, J=9.0 Hz, C$_6$H$_4$—NO$_2$); 8.26 (2H, doublet, J=9.0 Hz, C$_6$H$_4$—NO$_2$).

(c) (3S, 4R)-4-Bromomethylcarbonylmethyl-3-[1-(R)-p-nitrobenzyloxycarbonyloxyethyl]-acetidin-2-one An aqueous solution of chromic acid (1.78 ml.) was added to a mixture of 0.592 g. of the hydroxyazetidin-2-one (22), tetrahydrofuran (1.5 ml.), benzene (1.5 ml.) and diethyl ether (30 ml.) at room temperature, after which the mixture was stirred for 3 hours. Methanol (0.13 g.) was added to the reaction mixture to remove excess chromic acid. The mixture was then diluted with ethyl acetate (360 ml.), washed successively with water and an aqueous solution of sodium chloride, and dried over sodium sulphate. The solvent was then distilled off under reduced pressure and the resulting oily residue was subjected to rapid chromatography using silica gel and eluted with a 1:1 by volume mixture of benzene and ethyl acetate, to afford 0.461 g. (yield 78%) of the desired bromomethylazetidin-2-one (23).

Nuclear Magnetic Resonance Spectrum (CDCl$_3$) δppm: 1.36 (3H, doublet, J=6.0 Hz, CH$_3$); 2.95 (2H, singlet, CH$_2$CO); 3.77 (2H, singlet, CH$_2$Br); 5.12 (2H, singlet, —CH$_2$—C$_6$H$_4$—NO$_2$); 6.48 (1H, singlet, NH); 7.44 (2H, doublet, J=9.0 Hz, —C$_6$H$_4$—NO$_2$); 8.20 (2H, doublet, J=9.0 Hz, —C$_6$H$_4$—NO$_2$).

(d) (3S, 4R)-4-(2-p-Nitrobenzyloxycarbonylaminoethyl)thiomethylcarbonylmethyl-3-[1-(R)-p-nitrobenzyloxycarbonyloxyethyl]-azetidin-2-one 2-(p-Nitrobenzyloxycarbonylaminoethyl) mercaptan (0.036 g.) was added to a mixture of 0.05 g. of the bromomethylazetidin-2-one (23) and dry tetrahydrofuran (1.5 ml.). The mixture was cooled to −78° C. and a solution (0.079 ml.) of n-butyllithium in n-hexane was added thereto. The mixture was stirred at that temperature for 1.5 hours, after which acetic acid (0.016 g.) was added. The mixture was diluted with ethyl acetate (30 ml.), washed successively with water and an aqueous solution of sodium chloride, and then dried over sodium sulphate. The solvent was distilled off under reduced pressure and the resulting oily residue was subjected to rapid chromatography using silica gel and eluted with a 1:4 by volume mixture of benzene and ethyl acetate, to afford 0.065 g. (yield 92%) of the desired azetidin-2-one (24).

Nuclear Magnetic Resonance Spectrum (CDCl$_3$) δppm: 1.34 (3H, doublet, J=6.0 Hz, CH$_3$); 2.56 (2H, triplet, J=7.0 Hz SCH$_2$CH$_2$); 2.8–3.1 (2H, multiplet, CH$_2$COCH$_2$S); 3.18 (2H, singlet, COCH$_2$S); 3.40 (2H, tripled doublet J=7.0 Hz, CH$_2$CH$_2$NH); 3.7–4.2 (1H, multiplet, 4—CH); 5.14 (2H, singlet, —OCOO—CH$_2$—C$_6$H$_4$—NO$_2$); 5.19 (2H, singlet, —NHCOO—CH$_2$—C$_6$H$_4$—NO$_2$); 5.54 (1H, triplet, J=7.0 Hz, CH$_2$NH); 6.70 (1H, singlet, azetidinone —NH); 7.48 (2H, doublet, J=9.0 Hz —C$_6$H$_4$—NO$_2$) and 8.15 (2H, doublet, J=9.0 Hz,—C$_6$H$_4$—NO$_2$); 7.50 (2H, doublet, J=9.0 Hz, —C$_6$H$_4$—NO$_2$) and 8.18 (2H, doublet, J=9.0 Hz, —C$_6$H$_4$—NO$_2$).

(e) (3S, 4R)-1-(1-Hydroxy-1-p-nitrobenzyloxycarbonylmethyl)-4-(2-p-nitrobenzyloxycarbonylaminoethyl)thiomethylcarbonylmethyl-3-[1-(R)-p-nitrobenzyloxycarbonyloxyethyl]-azetidin-2-one A solution of p-nitrobenzyl glyoxylate hydrate (0.0377 g.) in benzene (22 ml.) was refluxed in a vessel equipped with a dehydrater (Dien Stark apparatus) and concentrated to about 1 ml. of benzene volume. A solution of 0.05 g. of the azetidin-2-one (24) in dioxan (0.3 ml.) was added and the mixture was stirred for 2 hours. The solvent was distilled off under reduced pressure and the resulting oily residue was subjected to rapid chromatography and eluted with a 1:1 by volume mixture of benzene and ethyl acetate, to give 0.042 g. (yield 62%) of the desired hydroxyazetidin-2-one (25).

Nuclear Magnetic Resonance Spectrum (CDCl$_3$) δppm: 1.33 (3H, doublet, J=5.5 Hz, CH$_3$); 5.15 (2H, singlet, OCOOCH$_2$—C$_6$H$_4$—NO$_2$); 5.20 (2H, singlet, NHCOOCH$_2$—C$_6$H$_4$—NO$_2$); 5.33 (2H, singlet CHCOOCH$_2$—C$_6$H$_4$—NO$_2$); 7.52 (6H, doublet, J=9.0 Hz, —C$_6$H$_4$—NO$_2$×3); 8.19 (6H, doublet, J=9.0 Hz, —C$_6$H$_4$—NO$_2$×3).

(f) (3S, 4R)-4-(2-p-Nitrobenzyloxycarbonylaminoethyl)thiomethylcarbonylmethyl-3-[1-(R)-p-nitrobenzyloxycarbonyloxyethyl]-1-(1-p-nitrobenzyloxycarbonyl-1-triphenylphosphoranylidenemethyl)-azetidin-2-one A solution of 0.042 g. of the hydroxyazetidin-2-one (25) in 3 ml. of dry tetrahydrofuran was cooled to −15° C. under an argon atmosphere. 2,6-Lutidine (0.0166 g.) and a solution of thionyl chloride (0.0184 g.) in dry tetrahydrofuran (2 ml.) were successively added to the above solution, after which the mixture was stirred at the same temperature for 20 minutes. The reaction mixture was then concentrated to dryness at room temperature under reduced pressure to remove tetrahydrofuran, thionyl chloride and 2,6-lutidine. To the resulting residue were added dry tetrahydrofuran (2 ml.), triphenylphosphine (0.027 g.) and 2,6-lutidine (0.011 g.) and then the mixture was stirred over an oil bath at a bath temperature of 55° C. for 5 hours. The reaction mixture was then diluted with ethyl acetate (30 ml.), washed with an aqueous solution of sodium chloride and dried over sodium sulphate. The solvent was evaporated off under reduced pressure and the resulting oily residue was subjected to rapid chromatography using silica gel eluted with a 3:7 by volume mixture of benzene and ethyl acetate, to give 0.045 g. (yield 83%) of the desired phosphoranylideneazetidinone (26).

(g) p-Nitrobenzyl (5R, 6S)-3-(2-p-nitrobenzyloxycarbonylaminoethyl)thiomethyl-6-[1-(R)-p-nitrobenzyloxycarbonyloxyethyl]-7-oxo-1-azabicyclo[3.2.0]hept-2-ene-2-carboxylate Toluene (250 ml.) was refluxed in a vessel equipped with a dehydrater (Dien Stark apparatus) and concentrated to about 160 ml. A catalytic amount of hydroquinone and 0.34 g. of the phosphoranylidene-azetidin-2-one (26) were added to the above concentrate and then the mixture was refluxed under an argon atmosphere for 30 minutes. Toluene was distilled off from the reaction mixture at room temperature under reduced pressure and the resulting oily residue was subjected to rapid chromatography using silica gel eluted with a 7:3 by volume mixture of benzene and ethyl acetate, to give 0.21 g. (yield 83%) of the desired azabicycloheptene (27).

Nuclear Magnetic Resonance Spectrum (CDCl₃) δppm 1.49 (3H, doublet, J=6.5 Hz, CH₃); 2.60 (2H, triplet, J=6.0 Hz, SCH₂C$\underline{H}$₂); 2.8-3.9 (7H, multiplet, 4—CH, 6—CH, C$\underline{H}$₂SCH₂C$\underline{H}$₂); 3.9-4.4 (1H, multiplet, 5—CH); 5.26 (2H, singlet, OCOOC$\underline{H}$₂—C₆H₄—NO₂); 5.34 (2H, singlet, NHCOOC$\underline{H}$₂—C₆H₄—NO₂); 5.26 and 5.59 (2H, AB-quartet, J=14 Hz, COOC$\underline{H}$₂—C₆H₄—NO₂); 5.76 (1H, triplet J=7.0 Hz, NH); 7.35-7.90 (6H, multiplet, —C₆H₄—NO₂×3); 8.30 (6H, doublet, J=9.0 Hz, —C₆H₄—NO₂×3).

(h) (5R, 6S)-3-(2-Aminoethylthiomethyl)-6-[1-(R)hydroxyethyl]-7-oxo-1-azabicyclo[3.2.0]hept-2-ene-2-carboxylic acid nal volume at room temperature under reduced pressure and the resulting concentrate was subjected to HP-20AG chromatography eluted with a 2% v/v aqueous acetone solution to give 0.022 g. (yield 60%) of the desired carboxylic acid (28).

Ultraviolet Absorption Spectrum (ethanol): λ$_{max}$=273 nm (ε=6500).

Nuclear Magnetic Resonance Spectrum (D₂O) δppm: 1.30 (3H, doublet, J=6.5 Hz, CH₃); 2.40-4.50 (11H, multiplet); 4.75 (NH₃ and OH).

EXAMPLE 4

(5R, 6S)-3-(2-Aminoethylthiomethyl)-6-(1-hydroxy-1-methylethyl)-7-oxo-1-azabicyclo[3.2.0]hept-2-ene-2-carboxylic acid (Compound No. 174)

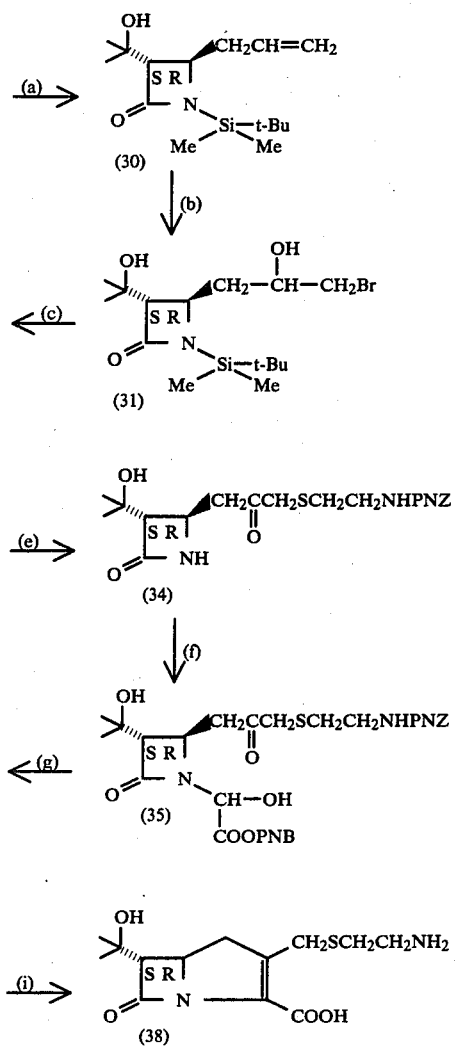

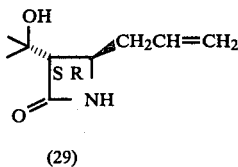

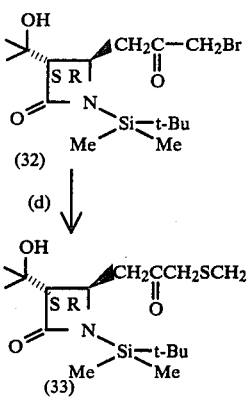

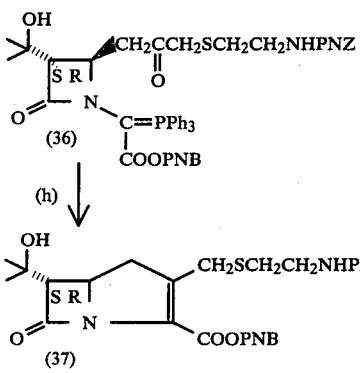

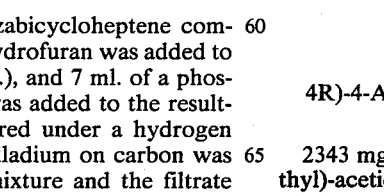

A solution of 0.1 g. of the azabicycloheptene compound (27) in 7 ml. of dry tetrahydrofuran was added to 10% palladium on carbon (0.1 g.), and 7 ml. of a phosphate buffer solution (pH 7.0) was added to the resulting mixture. This was then stirred under a hydrogen atmosphere for 2 hours. The palladium on carbon was filtered off from the reaction mixture and the filtrate was washed with ethyl acetate in a separating funnel. The solution was concentrated to one third of its origi- (a) (3S, 4R)-4-Allyl-1-t-butyldimethylsilyl-3-(1-hydroxy-1-methylethyl)-azetidin-2-one 2343 mg. of (3S, 4R)-4-allyl-3-(1-hydroxy-1-methylethyl)-acetidin-2-one (29) were dissolved in 50 ml. of anhydrous dimethylformamide. To the solution were added 5259 mg. of t-butyldimethylsilyl chloride and 500 ml. of triethylamine, with ice cooling and stirring. The mixture was then left to stand under ice cooling for 2 hours and then at room temperature for 22 hours. After completion of the reaction, the reaction mixture was diluted with ethyl acetate, washed five times with water and dried over magnesium sulphate. The solvent was distilled off under reduced pressure and the resulting residue was purified by silica gel chromatography eluted with a 5:1 by volume mixture of benzene and ethyl acetate, to give 3455 mg. (yield 88.0%) of the desired silyl compound (30) as an oil.

Nuclear Magnetic Resonance Spectrum (CDCl$_3$) δppm: 0.21 (3H, singlet, Me$_2$Si) and 0.25 (3H, singlet, Me$_2$Si); 0.93 (9H, singlet, t-BuSi); 1.18 (3H, singlet, Me$_2$C) and 1.24 (3H, singlet, Me$_2$C); 1.83–2.54 (3H, multiplet, —CH—CH$_2$—CH= and OH); 2.75 (1H, doublet, J=2 Hz, 3—CH); 3.25–3.71 (1H, multiplet, 4—CH); 4.80–5.23 (2H, multiplet, —CH=CH$_2$); 5.35–6.09 (1H, multiplet, CH$_2$—CH=CH$_2$).

(b) (3S, 4R)-4-(3-Bromo-2-hydroxypropyl)-1-t-butyldimethylsilyl-3-(1-hydroxy-1-methylethyl)-azetidin-2-one 619 mg. of the silyl-protected allylazetidin-2-one (30) were dissolved in 12 ml. of anhydrous dimethyl sulphoxide. To the solution were added 0.11 ml. of water and 621 mg. of N-bromosuccinimide, with ice cooling. The mixture was stirred at room temperature for 1.5 hours. After completion of the reaction, the reaction mixture was diluted with ethyl acetate, washed with water and then twice with a saturated aqueous solution of sodium hydrogen sulphite to decompose excess N-bromosuccinimide. The mixture was then washed successively five times with water and once with a saturated aqueous solution of sodium chloride, and then dried over sodium sulphate. The solvent was distilled off under reduced pressure and the resulting residue was purified by silica gel chromatography eluted with a 1:1 by volume mixture of benzene and ethyl acetate, to afford 753 mg. (yield 90.7%) of the desired bromohydrin compound (31).

(c) (3S, 4R)-4-Bromomethylcarbonylmethyl-1-t-butyldimethylsilyl-3-(1-hydroxy-1-methylethyl)-azetidin-2-one 741 mg. of the bromohydrin compound (31) were dissolved in 50 ml. of anhydrous methylene chloride. 2.12 g. of pyridinium chlorochromate were added to the above solution and the mixture was then stirred at room temperature for 4 hours. After completion of the reaction, the reaction mixture was diluted with ethyl acetate and passed over a Celite (Trade Mark) filter aid to remove insolubles. The resulting organic layer was washed five times with water and dried over sodium sulphate. The solvent was distilled off under reduced pressure and the resulting residue was purified by silica gel chromatography eluted with a 2:1 by volume mixture of benzene and ethyl acetate, to afford 385 mg. (yield 52.1%) of the desired 2-ketone compound (32) as an oil.

Nuclear Magnetic Resonance Spectrum (CDCl$_3$) δppm: 0.21 (3H, singlet, Me$_2$Si) and 0.25 (3H, singlet, Me$_2$Si); 0.93 (9H, singlet, t-BuSi); 1.23 (6H, singlet, Me$_2$C);
2.78 (1H, double doublet, J=9 and 16 Hz, —CH$_2$S—) and 3.20 (1H, double doublet, J=4 and 16 Hz, —CH$_2$S—); 2.83 (1H, broad singlet, OH); 2.85 (1H, doublet, J=2 Hz, 3—CH); 3.80 (2H, singlet, BrCH$_2$S); 3.58–3.90 (1H, multiplet, 4—CH).

(d) (3S, 4R)-1-t-Butyldimethylsilyl-3-(1-hydroxy-1-methylethyl)-4-(2-p-nitrobenzyloxycarbonylaminoethyl)thiomethylcarbonylmethyl-azetidin-2-one In 10 ml. of anhydrous tetrahydrofuran were dissolved 364 mg. of the 2-ketone compound (32) and 296 mg. of 2-p-nitrobenzyloxycarbonylaminomethylmercaptan and then the mixture was cooled to −78° C. under an argon atmosphere. 0.65 ml. of a solution of n-butyllithium in hexane (1.62 mmole/ml.) was added slowly to the above solution and stirring was continued at −78° C. for 1.5 hours. After completion of the reaction, 0.15 ml. of acetic acid was added to the reaction mixture at −78° C. The mixture was diluted with ethyl acetate, washed twice with a saturated aqueous solution of sodium chloride and dried over sodium sulphate. The solvent was distilled off under reduced pressure and the resulting residue was purified by silica gel chromatography eluted with a 1:1 by volume mixture of benzene and ethyl acetate, to give 328 mg. (yield 61.6%) of the desired cysteamine compound (33) as an oil.

Nuclear Magnetic Resonance Spectrum (CDCl$_3$) δppm: 0.24 (6H, singlet, Me$_2$Si); 0.94 (9H, singlet, t-BuSi); 1.26 (6H, singlet, Me$_2$C); 2.45–3.18 (4H, multiplet, CH—CH$_2$—CO, 3—CH and OH); 2.63 (2H, triplet, J=6 Hz, —S—CH$_2$CH$_2$—); 3.28 (2H, singlet, CO—CH$_2$—S); 3.36 (2H, quartet, J=6 Hz, NH—CH$_2$CH$_2$—); 3.68–3.90 (1H, multiplet, 4—CH); 5.20 (2H, singlet, benzyl CH$_2$); 5.68 (1H, broad singlet, NH); 7.55 (2H, doublet, J=10 Hz, —C$_6$H$_4$—NO$_2$) and 8.28 (2H, doublet, J=10 Hz, —C$_6$H$_4$—NO$_2$).

(e) (3S, 4R)-3-(1-Hydroxy-1-methylethyl)-4-(2-p-nitrobenzyloxycarbonylaminoethyl)thiomethylcarbonylmethyl-azetidin-2-one To 327 mg. of the cysteamine compound (33) were added 32 ml. of a solution of 0.25 N hydrochloric acid in methanol and the mixture was stirred at room temperature for 2 hours. After completion of the reaction, the reaction mixture was poured into a mixture of a saturated aqueous solution of sodium chloride and ethyl acetate. The mixture was stirred for 30 minutes. The aqueous layer was then extracted twice with ethyl acetate. The resulting ethyl acetate layer was dried over sodium sulphate and the solvent was distilled off. The resulting residue was purified by silica gel chromatography (eluent:ethyl acetate), to afford 182 mg. (yield 70.2%) of the desired desilyl compound (34).

Nuclear Magnetic Resonance Spectrum (CDCl$_3$) δppm: 1.21 (3H, singlet, Me$_2$C) and 1.30 (3H, singlet, Me$_2$C); 2.40–3.15 (4H, multiplet, CH—CH$_2$—CO, OH and 3—CH); 2.63 (2H, triplet, J=7 Hz, —S—CH$_2$CH$_2$); 3.30 (2H, singlet, CO—CH$_2$—S—); 3.35 (2H, quartet, J=7 Hz, NH—CH$_2$CH$_2$); 3.68–4.13 (1H, multiplet, 4—CH); 5.20 (2H, singlet, benzyl CH$_2$); 5.79 (1H, triplet, J=7 Hz, NH—CH$_2$—CH$_2$); 6.85 (1H, broad singlet, NH-1); 7.55 (2H, doublet, J=10 Hz, —C$_6$H$_4$—NO$_2$) and 8.24 (2H, doublet, J=10 Hz, —C$_6$H$_4$—NO$_2$).

(f) (3S, 4R)-3-(1-Hydroxy-1-methylethyl)-1-(1-hydroxy-1-p-nitrobenzyloxycarbonylmethyl)-4-(2-p-nitrobenzyloxycarbonylaminoethyl)thiomethylcarbonylmethyl-azetidin-2-one A solution of 1328 mg. of p-nitrobenzyl glyoxylate in 200 ml. of benzene was refluxed for 3 hours with a Dien Stark apparatus to dehydrate it and concentrate it to 20 ml. The solution was cooled to room temperature, and then a solution of 1269 mg. of the desilyl compound (34) in 10 ml. of anhydrous tetrahydrofuran and 200 ml. of benzene were added. The mixture was refluxed for 9 hours with a Dien Stark apparatus for dehydration and concentrated to 20 ml. After completion of the reaction, the solvent was distilled off and the residue was purified by silica gel chromatography (eluent:ethyl acetate), to give 1626 mg. (yield 86.8%) of the desired hydroxy compound (35).

(g) (3S, 4R)-3-(1-Hydroxy-1-methylethyl)-1-(1-p-nitrobenzyloxycarbonyl-1-triphenylphosphoranylidenemethyl)-4-(2-p-nitrobenzyloxycarbonylaminoethyl)thiomethylcarbonylmethyl-azetidin-2-one In 32 ml. of anhydrous tetrahydrofuran were dissolved 802 mg. of the hydroxy compound (35). A solution of 0.19 ml. of 2,6-lutidine and 0.11 ml. of thionyl chloride in 3 ml. of tetrahydrofuran was added to the above solution at −20° C. under an argon atmosphere. The mixture was stirred at from −20° to −25° C. for 20 minutes and then at room temperature for 20 minutes. After completion of the reaction, the mixture was diluted with 100 ml. of benzene and insolubles were filterd off. The filtrate was concentrated by evaporation under reduced pressure. The concentrate was diluted with toluene by azeotropy. The resulting crude chloro compound was dissolved in 40 ml. of anhydrous tetrahydrofuran. 658 mg. of triphenylphosphine and 0.28 ml. of 2,6-lutidine were added to the above solution. The mixture was then stirred at 40°–45° C. for 4.5 hours and then left to stand at room temperature overnight. The mixture was diluted with ethyl acetate, washed twice with water and dried over sodium sulphate. The solvent was distilled off under reduced pressure and the resulting crude product was purified by silica gel chromatography (eluent:ethyl acetate), to afford 514 mg. (yield 46.5%) of the desired phosphoran compound (36). There were also obtained 194 mg. (25.6%) of the azabicycloheptene compound (37), which was formed from the phosphoran compound (36) by ring-closure.

(h) p-Nitrobenzyl (5R, 6S)-6-(1-hydroxy-1-methylethyl)-3-(2-p-nitrobenzyloxycarbonylaminoethyl)thiomethyl-7-oxo-1-azabicyclo[3.2.0]hept-2-ene-2-carboxylate A solution of 507 mg. of the phosphoran compound (36) in 10 ml. of anhydrous tetrahydrofuran was added to 200 ml. of benzene. After addition of 25.3 mg. of hydroquinone, the mixture was refluxed under an argon atmosphere for 3.5 hours with a Dien Stark apparatus for dehydration and concentrated to 50 ml. The solvent was distilled off under reduced pressure and the resulting residue was purified by silica gel chromatography eluted with a 1:2 by volume mixture of benzene and ethyl acetate, to give 334 mg. (yield 95.8%) of the desired azabicycloheptene compound (37).

Nuclear Magnetic Resonance Spectrum (CDCl$_3$) δppm: 1.26 (3H, singlet, Me$_2$C) and 1.35 (3H, singlet, Me$_2$C); 1.93 (1H, broad singlet, OH); 2.35 (2H, triplet, J=7 Hz, —S—CH$_2$—CH$_2$); 2.85–3.73 (7H, multiplet, 4—CH$_2$, S—CH$_2$—C=, NH—CH$_2$CH$_2$, 6—CH); 3.83–4.33 (1H, multiplet, 5—CH); 5.09 (2H, singlet, NH—CO—O—CH$_2$); 5.09 and 5.38 (2H, AB-quartet, J=13 Hz, COOCH$_2$); 7.41 (2H, doublet, J=9 Hz, —C$_6$H$_4$—NO$_2$); 7.63 (1H, singlet, NH); 8.10 (2H, doublet, J=9 Hz, —C$_6$H$_4$—NO$_2$).

(i) (5R, 6S)-3-(2-Aminoethylthiomethyl)-6-(1-hydroxy-1-methylethyl)-7-oxo-1-azabicyclo[3.2.0]hept-2-ene-2-carboxylic acid 37 ml. of phosphate buffer (pH 6.98) and 1611 mg. of 10% palladium on carbon were added to a solution of 529 mg. of the azabicycloheptene compound (37) in 37 ml. of anhydrous tetrahydrofuran. The mixture was subjected to catalytic reduction, with stirring, under a hydrogen atmosphere at room temperature for 2 hours. After completion of the reduction insolubles were filtered off using a Celite (Trade Mark) filter aid. The insolubles were further washed three times, each time with 10 ml. of phosphate buffer. The resulting filtrate was washed three times, each time with 20 ml. of ethyl acetate, and the aqueous layer was concentrated to 15 ml. The concentrate was charged onto an HP-20AG chromatography column (200 ml. content) and, after enough washing with water, eluted with a 2% v/v aqueous acetone solution. Fractions showing a positive ninhydrin reaction were collected and concentrated to afford 104 mg. (yield 40.1%) of the desired azabicycloheptene compound (38).

Nuclear Magnetic Resonance Spectrum (D$_2$O) δppm: 1.28 (3H, singlet, Me$_2$C) and 1.32 (3H, singlet, Me$_2$C); 2.53–4.35 (10H, multiplet).

Ultraviolet Absorption Spectrum (H$_2$O) $\lambda_{max}$:275 nm.

EXAMPLE 5

(5R,6S)-3-[2-Amino-1-(R)-methylethyl]thiomethyl-6-[1-(R)-hydroxyethyl]-7-oxo-1-azabicyclo[3.2.0]hept-2-ene-2-carboxylic acid (Compound No. 23)

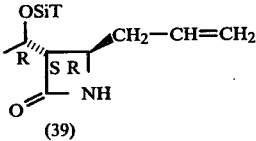

(39)

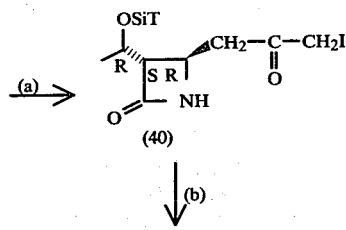

(40)

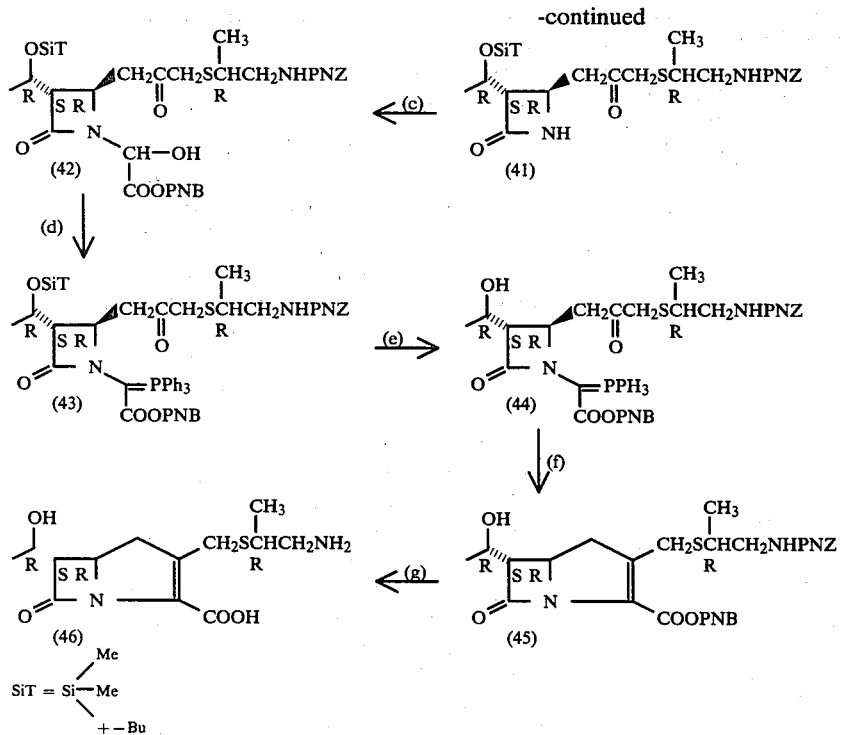

SiT = Si(Me)(Me)(t-Bu)

(a)
(3S,4R)-3-[1-(R)-t-Butyldimethylsilyloxyethyl]-4-iodomethylcarbonylmethyl-azetidin-2-one (40)

To a suspension of silver chromate (6.57 g) and a 4A molecular sieve (9.0 g) in 90 ml of methylene chloride were added iodine (6.97 g) and pyridine (0.25 ml) at 0° C. and the mixture was stirred for 10 minutes. A solution of 1.62 g. of (3S,4R)-4-allyl-3-[1-(R)-t-butyldimethylsilyloxyethyl]-azetidin-2-one (39) in 10 ml of methylene chloride was added dropwise over 5 minutes to the ice-cooled suspension, and the mixture was then stirred for 60 minutes at 0° C.. The cooling bath was then removed and the reaction mixture was stirred for 2 hours at room temperature. The resulting dark-brown mixture was filtered through a pad of a Celite (Trade Mark) filter aid. The filtrate was washed with a 5% w/w aqueous solution of sodium thiosulphate and a saturated aqueous solution of sodium chloride, and dried over sodium sulphate. The crude product obtained after concentration was purified by rapid silica gel column chromatography eluted with a 3:2 by volume mixture of cyclohexane and ethyl acetate, to give 1.78 g (yield 71.9%) of the desired 2-keto compound (40) as an oil.

Infrared Absorption Spectrum (CHCl$_3$), cm$^{-1}$: 1760 ($\beta$-lactam), 1710 (Ketone).

Nuclear Magnetic Resonance Spectrum (CDCl$_3$) $\delta$ppm: 0.08 (6H, singlet, CH$_3$—Si—CH$_3$); 0.90 (9H, singlet, t-Bu); 1.25 (3H, doublet, J=6.0 Hz, C$\underline{H}_3$—CH—OSi); 2.67–3.48 (3H, multiplet); 3.68–4.38 (2H, multiplet); 3.83 (2H, singlet, COCH$_2$I); 6.53 (1H, broad singlet, NH).

(b)
(3S,4R)-3-[1-(R)-t-Butyldimethylsilyloxyethyl]-4-[1-(R)-methyl-2-p-nitrobenzyloxycarbonylaminoethyl]thiomethylcarbonylmethyl-azetidin-2-one (41)

To a solution of [1-(R)-methyl-2-p-nitrobenzyloxycarbonylaminoethyl]mercaptan (4.21 g) in tetrahydrofuran (16 ml) and methanol (32 ml) were successively added solid NaHCO$_3$ (1.31 g) and a solution of silver nitrate (2.65 g) in methanol (130 ml), with ice-water cooling; the mixture was then stirred for 5 minutes. To the resulting suspension was added a solution of 3.20 g. of the 2-keto compound (40) in methanol (32 ml) at 0° C. The reaction mixture was then stirred on an oil bath (at 40° C.) for 16 hours. The resulting mixture was diluted with ethyl acetate and filtered through a pad of a Celite (Trade Mark) filter aid. The filtrate was washed twice with a saturated aqueous solution of sodium chloride, and dried over sodium sulphate. The crude product obtained after concentration was purified by rapid silica gel column chromatography eluted with a 1:2 by volume mixture of cyclohexane and ethyl acetate, to give 2.90 g (yield 67.3%) of the desired azetidin-2-one (41) as an oil.

Infrared Absorption Spectrum (CHCl$_3$) cm$^{-1}$: 1760 ($\beta$-lactam), 1725 (ester).

Nuclear Magnetic Resonance Spectrum (CDCl$_3$) $\delta$ppm: 0.05 (6H, singlet, CH$_3$—Si—CH$_3$); 0.83 (9H, singlet, t-Bu); 1.22 (3H, doublet, J=6.0 Hz, CH$_3$—C$\underline{H}$—OSi); 1.27 (3H, doublet, J=6.0 Hz, CH$_3$—C$\underline{H}$—S); 2.60–3.43 (6H, multiplet); 3.33 (2H, broad singlet, —CO—CH$_2$—S—); 3.77–4.38 (2H, multiplet); 5.16 (2H, singlet, benzyl CH$_2$); 5.57 (1H, triplet, C$\underline{H}_2$NH); 6.47 (1H, singlet, azetidine NH); 7.45 (2H, doublet, J=9.0 Hz, —C$_6$H$_4$—NO$_2$); 8.17 (2H, doublet, J=9.0 Hz, —C$_6$H$_4$—NO$_2$)

(c)
(3S,4R)-3-[1-(R)-t-Butyldimethylsilyloxyethyl]-1-(1-hydroxy-1-p-nitrobenzyloxycarbonylmethyl)-4-[1-(R)-methyl-2-p-nitrobenzyloxycarbonylaminoethyl]thiomethylcarbonylmethyl-azetidin-2-one (42)

A solution of p-nitrobenzyl glyoxylate hydrate (2.37 g) in benzene (700 ml) was refluxed in a vessel equipped with a dehydrater (Dien Stark apparatus) and concentrated to a benzene volume of about 500 ml. A solution of 2.89 g. of the azetidin-2-one (41) in 20 ml. of tetrahydrofuran was added and the mixture was refluxed for 7 hours. The solvent was distilled off under reduced pressure and the resulting oily residue was subjected to rapid chromatography through silica gel eluted with a 3:2 by volume mixture of cyclohexane and ethyl acetate, to give 3.88 g. (yield 97.5%) of the desired hydroxyazetidin-2-one (42).

Infrared Absorption Spectrum (CHCl$_3$) cm$^{-1}$: 1770 (β-lactam), 1730(ester).

(d) (3S,4R)-3-[1-(R)-t-Butyldimethylsilyloxyethyl]-4-[1-(R)-methyl-2-p-nitrobenzyloxycarbonylaminoethyl]thiomethylcarbonylmethyl)-1-(1-p-nitrobenzyloxycarbonyl-1-triphenylphosphoranylidenemethyl)-azetidin-2-one (43)

A solution of 3.87 g. of the hydroxyazetidin-2-one (42) in 100 ml. of dry tetrahydrofuran was cooled to −24° C. under an argon atmosphere. 2, 6-Lutidine (1.8 ml.) and thionyl chloride (1.1 ml) were successively added to the above solution and the mixture was then stirred at the same temperature for 20 minutes and at room temperature for 20 minutes. The reaction mixture was then diluted with benzene and filtered through a pad of a Celite (Trade Mark) filter aid. The filtrate was then concentrated to dryness at room temperature under reduced pressure. To the resulting residue were added dry tetrahydrofuran (100 ml), triphenylphosphine (2.67 g) and 2, 6-lutidine (1.20 ml) and then the mixture was stirred at a bath temperature of 40° C. for 5 hours. The reaction mixture was diluted with ethyl acetate (500 ml), washed with a saturated aqueous solution of sodium chloride and dried over sodium sulphate. The solvent was evaporated under reduced pressure and the resulting oily residue was subjected to rapid chromatography using silica gel eluted with a 4:1 by volume mixture of benzene and acetone, to give 2.75 g (yield 53.9%) of the desired phosphoranylideneazetidinone (43) as an amorphous powder.

Infrared Absorption Spectrum (CHCl$_3$) cm$^{-1}$: 1735 (β-lactam, ester).

(e) (3S,4R)-3-[1-(R)-Hydroxyethyl]-4-[1-(R)-methyl-2-p-nitrobenzyloxycarbonylaminoethyl]thiomethylcarbonylmethyl-1-(1-p-nitrobenzyloxycarbonyl-1-triphenylphosphoranylidenemethyl)azetidin-2-one (44)

To a solution of 2.71 g of the ylide compound (43) in 270 ml of methanol were added 108 ml of 10% hydrochloric acid, with ice-water cooling. The cooling bath was then removed and the reaction mixture was stirred for 2 hours at room temperature. The reaction mixture was poured dropwise into a mixture of 50 g of sodium hydrogen carbonate, 500 ml of water and 500 ml of ethyl acetate, with ice-water cooling, and the mixture was then saturated with sodium chloride. The aqueous layer was separated and extracted with more ethyl acetate. The combined organic phases were washed with an aqueous solution of sodium hydrogen carbonate and a saturated aqueous solution of sodium chloride, and dried over sodium sulphate. The crude product obtained after concentration was purified by rapid silica gel column chromatography eluted with a 1:1 by volume mixture of cyclohexane and acetone, to give 2.16 g (yield 89.8%) of compound (44) as an amorphous powder.

Infrared Absorption Spectrum (CHCl$_3$) cm$^{-1}$: 1735 (β-lactam, ester).

(f) p-Nitrobenzyl (5R,6S)-6-[1-(R)-hydroxyethyl]-3-[1-(R)-methyl-2-p-nitrobenzyloxycarbonylaminoethyl]thiomethyl-7-oxo-1-azabicyclo[3.2.0]hept-2-ene-2-carboxylate (45)

Benzene (700 ml) was refluxed in a vessel equipped with a dehydrater (Dien Stark apparatus) and concentrated to about 500 ml. A catalytic amount of hydroquinone and 2.14 g of the phosphoranylidene-azetidin-2-one (44) were added to the concentrate and the mixture was then refluxed in an argon atmosphere for 3 hours. Benzene was distilled from the reaction mixture at room temperature under reduced pressure and the resulting oily residue was subjected to rapid chromatography using silica gel eluted with 2:1 by volume mixture of benzene and acetone, to give 1.23 g. (yield 83.4%) of the desired azabicycloheptene (45).

Infrared Absorption Spectrum (CHCl$_3$) cm$^{-1}$: 1780 (β-lactam), 1730 (ester).

Nuclear Magnetic Resonance Spectrum (CDCl$_3$) δppm: 1.23 (3H, doublet, J=6.0 Hz CH$_3$CH—Si); 1.33 (3H, doublet, J=6.0 Hz, CH$_3$—CH—S—); 2.58–3.43 (7H, multiplet); 3.75 (2H, broad singlet, CH$_2$—S); 3.88–4.40 (2H, multiplet); 5.13 (2H, singlet—NH-COOCH$_2$—); 5.12 and 5.43 (2H, AB-quartet, J=14.0 Hz, —COOCH$_2$—); 7.43 (2H, doublet, J=8.0 Hz, —C$_6$H$_4$—NO$_2$); 7.57 (2H, doublet, J=8.0 Hz, —C$_6$H$_4$—NO$_2$); 8.18 (4H, doublet, J=8.0 Hz, —C$_6$H$_4$—NO$_2$X2).

(g) (5R,6S)-3-[2-Amino-1-(R)-methylethyl]thiomethyl-6-[1-(R)-hydroxyethyl]-7-oxo-1-azabicyclo[3.2.0]hept-2-ene-2-carboxylic acid (46)

A solution of 502 mg. of the azabicycloheptene compound (45) in 35 ml of dry tetrahydrofuran were added to 1.5 g of 10% palladium on carbon, and 35 ml of a phosphate buffer solution (pH 7.0) were then added to the mixture. The resulting mixture was then hydrogenated under a hydrogen pressure of 40 p.s.i. and at a temperature of 10° C. for 30 minutes. The palladium on carbon was filtered off from the reaction mixture and the filtrate was washed with diethyl ether in a separating funnel. The solution was concentrated to one half of its original volume at 10° C. under reduced pressure and the resulting concentrate was subjected to HP-20AG chromatography eluted with a 2% v/v aqueous acetone solution, to give 76.9 mg (yield 31.3%) of the desired carboxylic acid (46), Compound No. 23.

Infrared Absorption Spectrum (KBr disc) cm$^{-1}$: 1755.

Ultraviolet Absorption Spectrum (H$_2$O)λ$_{max}$: 274 nm (ε=7028).

Nuclear Magnetic Resonance Spectrum (D$_2$O) δppm: 1.33 (3H, doublet, J=6.0 Hz, CH$_3$—CH—Si); 1.37 (3H, doublet, J=6.0 Hz, CH$_3$—CH—S); 2.95–3.53 (6H, multiplet); 3.53 (2H, broad singlet, CH$_2$—S—); 4.00–4.47 (2H, multiplet, 6—CH and S—CH—CH$_2$).

EXAMPLE 6

(5R,6S)-3-(2-Aminoethylthiomethyl)-6-[1-(R)-hydroxyethyl]-7-oxo-1-azabicyclo[3.2.0]hept-2-ene-2-carboxylic acid (Compound No. 10) and
(5R,6S)-3-(2-formimidoylaminoethylthiomethyl)-6-[1-(R)-hydroxyethyl]-7-oxo-1-azabicyclo[3.2.0]hept-2-ene-2-carboxylic acid (Compound No. 11)

ature. The reaction mixture was then diluted with ethyl acetate, washed successively with water, an aqueous solution of sodium hydrogen sulphite, water and an aqueous solution of sodium chloride, and dried over sodium sulphate. The solvent was distilled off under reduced pressure and the resulting oily residue was subjected to rapid chromatography using silica gel eluted with a 1:1 by volume mixture of cyclohexane and

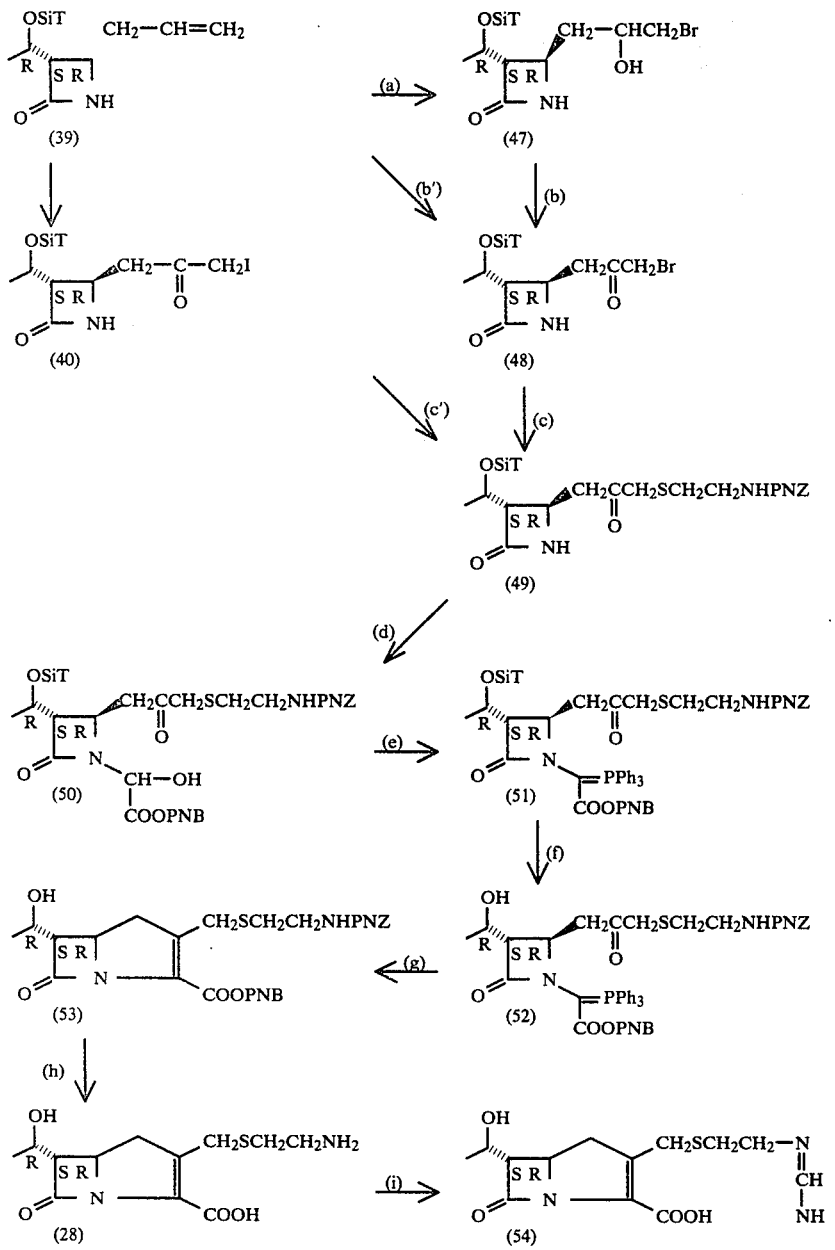

(a)
(3S,4R)-4-(3-Bromo-2-hydroxypropyl)-3-[1-(R)-t-butyldimethylsilyloxyethyl]-azetidin-2-one (47)

To a solution of 3.01 g of (3S,4R)-4-allyl-3-[1-(R)-t-butyldimethylsilyloxyethyl]-azetidin-2-one (39) in 60 ml. of dimethyl sulphoxide were added, over a period of 10 minutes, 3.19 g. of N-bromosuccinimide and 0.53 ml. of water, whilst cooling on an ice-water bath; the resulting mixture was then stirred for 2 hours at room temperethyl acetate, to give 1.85 g. (yield 45.2%) of the desired bromohydrin compound (47). This product was a diastereomeric mixture as a result of the newly formed hydroxy group, and the compound was submitted to the next reaction without separation of the isomers.

(b)
(3S,4R)-4-Bromomethylcarbonylmethyl-3-[1-(R)-t-butyldimethylsilyloxyethyl]-azetidin-2-one (48)

1.85 g of the bromohydrin compound (47) were dissolved in 200 ml of anhydrous methylene chloride. 7.61 g. of pyri-dinium chlorochromate were added to the resulting solution and the mixture was then stirred at room temperature overnight. After completion of the reaction, the reaction mixture was diluted with ethyl acetate and passed over a pad of a Celite (Trade Mark) filter aid to remove insolubles. The resulting organic layer was washed five times with water and then dried over sodium sulphate. The solvent was distilled off under reduced pressure and the resulting residue was purified by silica gel chromatography eluted with a 1:1 by volume mixture of cyclohexane and ethyl acetate, to afford 1.44 g. (yield 77.2%) of the desired 2-ketone compound (48) as an oil.

Nuclear Magnetic Resonance Spectrum (CDCl$_3$) δppm: 0.07 (6H, singlet, CH$_3$—SiCH$_3$); 0.87 (9H, singlet, t-Bu); 1.20 (3H, doublet, J=6.0 Hz, C$\underline{H}_3$—CH—OSi); 2.77–3.22 (3H, multiplet); 3.63–4.45 (2H, multiplet); 3.97 (2H, singlet, COCH$_2$Br); 6.32 (1H, broad singlet, NH).

(b')
(3S,4R)-4-Bromomethylcarbonylmethyl-3-[1-(R)-t-butyldimethylsilyloxyethyl]-azetidin-2-one (48)

To a suspension of 1.10 g. of silver chromate and 1.5 g. of a 4 A molecular sieve in 10 ml. of methylene chloride were added bromine (0.46 ml) and pyridine (0.04 ml) at 0° C. and the mixture was stirred for 10 minutes. A solution of 274 mg. of (3S,4R)-4-allyl-3-[1-(R)-t-butyldimethylsilyloxyethyl]-azetidin-2-one (39) in 5 ml. of methylene chloride was then added, whilst ice-cooling, dropwise over a period of 5 minutes. The mixture was then stirred at 0° C. for 1 hour. The cooling bath was then removed and the reaction mixture was stirred for 2 hours at room temperature.

The resulting dark-brown mixture was filtered through a pad of a Celite (Trade Mark) filter aid. The filtrate was washed with a 5% w/w aqueous solution of sodium thiosulphate and a saturated aqueous solution of sodium chloride, and dried over sodium sulphate. The crude product obtained after concentration was purified by rapid silica gel column chromatography eluted with a 1:1 by volume mixture of cyclohexane and ethyl acetate to give 147 mg. (yield 39.8%) of the desired 2-keto compound (48) as an oil having the same properties as the product of step (b).

(c)
(3S,4R)-3-[1-(R)-t-Butyldimethylsilyloxyethyl]-4-(2-p-nitrobenzyloxycarbonylaminoethyl)thiomethylcarbonylmethylazetidin-2-one (49)

0.536 g. of 2-(p-nitrobenzyloxycarbonylamino)ethylmercaptan was added to a mixture of 0.635 g. of bromomethylazetidin-2-one (48) and 20 ml. of dry tetrahydrofuran. The mixture was cooled to −78° C. and a solution of 1.18 ml of n-butyllithium in n-hexane was added thereto. The mixture was stirred at that temperature for 1.5 hours. Acetic acid (0.22 ml) was added to the reaction mixture. The mixture was then diluted with 380 ml of ethyl acetate and washed successively with water and an aqueous solution of sodium chloride, and was then dried over sodium sulphate. The solvent was distilled off under reduced pressure and the resulting oily residue was subjected to rapid chromatography using silica gel eluted with a 1:4 by volume mixture of benzene and ethyl acetate, to afford 0.718 g. (yield 76.3%) of the desired azetidin-2-one (49).

Nuclear Magnetic Resonance Spectrum (CDCl$_3$) δppm: 0.10 (6H, singlet, CH$_3$SiCH$_3$); 0.83 (9H, singlet, t-Bu); 1.16 (3H, doublet, J=6.0 Hz, C$\underline{H}_3$—CH—OSi); 2.58 (2H, triplet, J=5.0 Hz, —SC$\underline{H}_2$CH$_2$);
2.8–3.0 (2H, multiplet, C$\underline{H}_2$—CO—CH$_2$S); 3.15 (2H, singlet, COCH$_2$S); 3.6–4.3 (1 H, multiplet, 4—CH); 5.10 (2H, singlet, benzyl CH$_2$); 5.52 (1H, triplet, J=7.0 Hz, CH$_2$N$\underline{H}$); 6.56 (1H, broad singlet, azetidine NH); 7.56 (2H, doublet, J=9.0 Hz, —C$_6$H$_4$—NO$_2$); 8.22 (2H, doublet, J=9.0 Hz, —C$_6$H$_4$—NO$_2$).

(c')
(3S,4R)-3-[1-(R)-t-Butyldimethylsilyloxyethyl]-4-(2-p-nitrobenzyloxycarbonylaminoethyl)thiomethylcarbonylmethylazetidin-2-one (49)

To a solution of 2-(p-nitrobenzyloxycarbonylamino)ethylmercaptan (523 mg. 2.042 mmole) in tetrahydrofuran (2 ml) and methanol (4 ml) were successively added solid sodium bicarbonate (172 mg, 2.042 mmole) and a solution of silver nitrate (347 mg. 2.042 mmole) in methanol (16 ml), with ice-water cooling. To the resulting suspension was added a solution of (3S, 4R)-3-[1-(R)-t-butyldimethylsilyloxyethyl]-4-iodomethylcarbonylmethylazetidin-2-one (40) (420 mg. 1.021 mmole) in methanol (4 ml). The reaction mixture was stirred on an oil bath (35°–45° C.) for 16 hours. The mixture was then diluted with ethyl acetate and filtered through a Celite (Trade Mark) filter aid. The filtrate was washed once with water and once with a saturated aqueous solution of sodium chloride, and dried over sodium sulphate. The solvent was then evaporated off to give an oil (530 mg). This crude substance was chromatographed on silica gel (15 g) to afford 397 mg of (3S, 4R)-3-[1-(R)-t-butyldimethylsilyloxyethyl]-4-(2-p-nitrobenzyloxycarbonylaminoethyl)thiomethylcarbonylmethyl-azetidin-2-one (49) as an oil having the same properties as the product of step (c).

(d)
(3S,4R)-3-[1-(R)-t-Butyldimethylsilyloxyethyl]-1-(1-hydroxy-1-p-nitrobenzyloxycarbonylmethyl)-4-(2-p-nitrobenzyloxycarbonylaminoethyl)thiomethylcarbonylmethyl-azetidin-2-one (50)

A solution of 0.604 g. of p-nitrobenzyl glyoxylate hydrate in 300 ml of benzene was refluxed in a vessel equipped with a dehydrater (Dien Stark apparatus) and concentrated to a benzene volume of about 12 ml. A solution of 0.718 g. of the azetidin-2-one (49) in 2 ml of benzene was added and the mixture was then refluxed for 6 hours. The solvent was distilled off under reduced pressure and the resulting oily residue was subjected to rapid chromatography and eluted with a 1:1:2 by volume mixture of n-hexane, acetone and ethyl acetate, to give 0.62 g. (yield 66.2%) of the desired hydroxyazetidin-2-one (50).

(e)
(3S,4R)-3-[1-(R)-t-Butyldimethylsilyloxyethyl]-4-(2-p-nitrobenzyloxycarbonylaminoethyl)thiomethylcarbonylmethyl-1-(1-p-nitrobenzyloxycarbonyl-1-triphenylphosphoranylidene)methyl-azetidin-2-one (51)

A solution of 0.05 g. of the hydroxyazetidin-2-one (50) in 3 ml. of dry tetrahydrofuran was cooled to −24° C. in an argon atmosphere. 2,6-Lutidine (0.0214 g.) and thionyl chloride (0.0238 g) were successively added to the above solution and the resulting mixture was stirred at the same temperature for 20 minutes and then at room temperature for 20 minutes. The reaction mixture was then diluted with benzene and filtered through a pad of a Celite (Trade Mark) filter aid. The filtrate was concentrated to dryness at room temperature under reduced pressure. To the resulting residue were added 2 ml. of dry tetrahydrofuran, 34.9 mg of triphenylphosphine and 14.3 mg of 2,6-lutidine, after which the mixture was stirred at a bath temperature of 55° C. for 5 hours. The reaction mixture as diluted with 30 ml of ethyl acetate, washed with a saturated aqueous solution of sodium chloride and dried over sodium sulphate. The solvent was evaporated off under reduced pressure and the resulting oily residue was subjected to rapid chromatography using silica gel eluted with a 4:1 by volume mixture of benzene and acetone, to give 25 mg. (yield 37.7%) of the desired phosphoranylideneazetidinone (51) as an amorphous powder.

(f)
(3S,4R)-3-[1-(R)-Hydroxyethyl]4-(2-p-nitrobenzyloxycarbonylaminoethyl)thiomethylcarbonylmethyl-1-(1-p-nitrobenzyloxycarbonyl-1-triphenylphosphoranylidenemethyl)azetidin-2-one (52)

To a solution of 24 mg. of the ylide compound (51) in 3 ml. of methanol was added, whilst cooling in a bath of ice-water, 1 ml. of 10% hydrochloric acid. The cooling bath was then removed and the reaction mixture was stirred for 40 minutes at room temperature. The reaction mixture was then poured dropwise into an aqueous mixture of 1 g. of sodium bicarbonate, 10 ml. of water and 10 ml. of ethyl acetate, and the mixture was then saturated with sodium chloride. The aqueous layer was separated and extracted with more ethyl acetate. The combined organic phases were washed with sodium hydrogen carbonate and saturated aqueous sodium chloride, and dried over sodium sulphate. The crude product obtained after concentration was purified by rapid silica gel column chromatography eluted with a 1:1 by volume mixture of cyclohexane and acetone, to give 16 mg. (yield 75.5%) of the desired hydroxy compound (52) as an amorphous powder.

(g) p-Nitrobenzyl (5R,6S)-6-[1-(R)-hydroxyethyl]-3-(2-p-nitrobenzyloxycarbonylaminoethyl)thiomethyl-7-oxo-1-azabicyclo[3.2.0]hept-2-ene-2-carboxylate (53)

Benzene (150 ml) was refluxed in a vessel equipped with a dehydrater (Dien Stark apparatus) and concentrated to about 100 ml. A catalytic amount of hydroquinone and 170 mg. of the phosphoranylidene-azetidin-2-one (52) were added to the above concentrate and the mixture was then refluxed in an argon atmosphere for 3 hours. The benzene was distilled off from the reaction mixture at room temperature under reduced pressure and the resulting oily residue was subjected to rapid chromatography using silica gel eluted with a 7:3 by volume mixture of benzene and acetone, to give 90 mg (yield 78%) of the desired azabicycloheptene (53).

Nuclear Magnetic Resonance Spectrum (CDCl₃) δppm: 1.35 (3H, doublet, J=6.5 Hz, CH₃CHO); 2.60 (2H, triplet, J=6.5 Hz, —CH₂CH₂); 2.9–3.4 (6H, multiplet); 3.6–3.8 (2H, multiplet); 4.0–4.4 (2H, multiplet); 5.18 (2H, singlet, NHCOOCH₂); 5.15 and 5.48 (2H, AB-quartet, J=14.0 Hz, C—COOCH₂); 7.60 (4H, doublet, J=8.5 Hz, —C₆H₄—NO₂); 8.18 (4H, doublet, J=8.5 Hz, —C₆H₄—NO₂ X 2).

(h)
(5R,6S)-3-(2-Aminoethylthiomethyl)-6-[1-(R)-hydroxyethyl]-7-oxo-1-azabicyclo[3.2.0]hept-2-ene-2-carboxylic acid (28)

A solution of 935 mg. of the azabicycloheptene compound (53) in 62 ml. of dry tetrahydrofuran was added to 2.8 g. of 10% palladium on carbon, and then 62 ml of a phosphate buffer solution (pH 7.0) were added to the mixture. The resulting mixture was then hydrogenated under a hydrogen pressure of 40 p.s.i. and a temperature of 10° C. for 30 minutes. The palladium on carbon was filtered off from the reaction mixture and the filtrate was washed with diethyl ether in a separating funnel. The aqueous solution was concentrated to one half of its original volume at 10° C. under reduced pressure and the resulting concentrate was subjected to HP-20AG chromatography eluted with a 2% v/v aqueous acetone solution to give 201 mg. (yield 45.1%) of the desired carboxylic acid (28), Compund No. 10.

Nuclear Magnetic Resonance Spectrum (D₂O) δppm: 1.28 (3H, doublet, J=6.0 Hz, CH₃CHO); 2.5–4.4 (11H, multiplet).

(i)
(5R,6S)-3-(2-Formimidoylaminoethylthiomethyl)-6-[1-(R)-hydroxyethyl]-7-oxo-1-azabicyclo[3.2.0]hept-2-ene-2-carboxylic acid (54)

A solution of 40 mg. of (5R,6S)-3-(2-aminoethylthiomethyl)-6-[1-(R)-hydroxyethyl]-7-oxo-1-azabicyclo[3.2.0]hept-2-ene-2-carboxylic acid in 15 ml of a phosphate buffer (pH 7.0, 0.1 N) was adjusted to pH 8.5 by the addition of a 2 N aqueous solution of sodium hydroxide at 0° C. To this solution was added methyl formimidate hydrochloride (220 mg) whilst the pH of the mixture was maintained at 8.5 and stirring was continued for 10 minutes at 0° C. The solution was chromatogaphed on HP-20AG (high porous adsorbent) (wet 40 ml) and the fraction eluted with 2% v/v acetone-water was lyophylized to give 12 mg. of (5R, 6S)-3-(2-formimidoylaminoethylthiomethyl)-6-[1-(R)-hydroxyethyl]-7-oxo-1-azabicyclo[3.2.0]hept-2-ene-2-carboxylic acid, Compound No. 11.

Nuclear Magnetic Resonance Spectrum (D₂O) δppm: 1.28 (3H, doublet, J=6.0 Hz); 2.5–4.4 (11H); 7.81 (1H, singlet).

EXAMPLE 7

(a)
p-Nitrobenzyl(5R,6S)-6-[1-(R)-hydroxyethyl]-3-(2-p-nitrobenzyloxycarbonylaminoethylsulphinylmethyl)-7-oxo-1-azabicyclo[3.2.0]hept-2-ene-2-carboxylate A solution of 22 mg of m-chloroperbenzoic acid in 2 ml of methylene chloride was added dropwise to 60 mg of p-nitrobenzyl (5R,6S)-6-[1-(R)-hydroxyethyl]-3-(2-p-nitrobenzyloxycarbonylaminoethyl)thiomethyl-7-oxo-1-azabicyclo[3.2.0]hept-2-ene-2-carboxylate (53), prepared as described in step (g) of Example 6, in 3 ml of methylene chloride, whilst cooling with ice-water. When the addition was complete, the reaction mixture was stirred at 0°–5° C. for 30 minutes. The resulting mixture containing precipitated material was diluted with 100 ml of ethyl acetate and then the solution was washed successively with a 5% w/v aqueous solution of sodium hydrogen sulphite (once), a saturated aqueous solution of sodium bicarbonate (twice) and a saturated aqueous solution of sodium chloride (three times). The solution was then dried over sodium sulphate, after which the solvents were evaporated under reduced pressure at room temperature, to give a solid substance. This crude substance was dissolved in dimethyl sulphoxide and then reprecipitated by the addition of benzene, to give 55 mg of the title compound as an amorphous powder.

Nuclear Magnetic Resonance Spectrum (hexadeuterated dimethyl sulphoxide) δppm:

1.17 (3H, doublet, J=6.0 Hz); 2.65–4.50 (11H, multiplet); 3.52 (2H and trace water in deuterated dimethyl sulphoxide); 5.18 (2H, singlet); 5.35 and 5.50 (2H, AB-quartet, J=15.0 Hz); 7.40–8.45 (8H, multiplet).

(b)
(5R,6S)-6-[1-(R)-Hydroxyethyl]-3-(2-p-nitrobenzyloxycarbonylaminoethylsulphinylmethyl)-7-oxo-1-azabicyclo[3.2.0]hept-2-ene-2-carboxylic acid Following the procedure described in step (h) of Example 6, the title compound was prepared from the product of step (a) of this Example.

Nuclear Magnetic Resonance Spectrum (D₂O) δppm: 1.29 (3H, doublet, J=6.0 Hz); 2.5–4.6 (11H, multiplet).

EXAMPLE 8

(a)
p-Nitrobenzyl(5R,6S)-6-[1-(R)-hydroxyethyl]-3-(2-p-nitrobenzyloxycarbonylaminoethylsulphonylmethyl)-7-oxo-1-azabicyclo[3.2.0]hept-2-ene-2-carboxylate A solution of 44 mg of m-chloroperbenzoic acid in 3 ml of methylene chloride was added dropwise to 60 mg of p-nitrobenzyl(5R,6S)-6-[1-(R)-hydroxyethyl]-3-(2-p-nitrobenzyloxycarbonylaminoethyl)thiomethyl-7-oxo-1-azabicyclo[3.2.0]hept-2-ene-2-carboxylate (53), prepared as described in step (g) of Example 6, whilst cooling with ice-water. The reaction mixture was then stirred at 0°–5° C. for 3 hours. Since some of the precipitates which appeared during this reaction showed the presence of both sulphoxide and sulphone, a further 30 ml of methylene chloride were added and stirring was continued at 0°–5° C. for 15 hours. The mixture was then diluted with 150 ml of ethyl acetate and then successively washed with a 10% w/v aqueous solution of sodium hydrogen sulphite (once), a saturated aqueous solution of sodium bicarbonate (twice) and a saturated aqueous solution of sodium chloride (three times). After drying the resulting solution over sodium sulphate, the solvents were removed by evaporation under reduced pressure at room temperature to give a solid substance. This crude substance was dissolved in ethyl acetate and passed through a short column packed with 2 g of silica gel. The column was eluted with ethyl acetate and the solvent was evaporated from the fractions containing the desired compound to give 42 mg of the title compound as a powder.

Nuclear Magnetic Resonance Spectrum (CDCl₃) δppm: 1.32 (3H, doublet, J=7.0 Hz); 2.30–4.85 (12H, multiplet);

5.20 (2H, singlet); 5.27 and 5.47 (2H, AB-quartet, J=15.0 Hz); about 5.6 (1H, broad singlet); 7.30–8.35 (8H, multiplet).

(b)
(5R,6S)-6-[1-(R)-Hydroxyethyl]-3-(2-p-nitrobenzyloxycarbonylaminoethylsulphonylmethyl)-7-oxo-1-azabicyclo[3.2.0]hept-2-ene-2-carboxylic acid Following the procedure described in step (h) of Example 6, the title compound was prepared from the product of step (a) of this Example.

Nuclear Magnetic Resonance Spectrum (D₂O) δppm: 1.30 (3H, doublet, J=6.0 Hz); 2.6–4.7 (11H, multiplet).

We claim:

1. Compounds selected from the group consisting of:
3-(2-aminoethylthiomethyl)-6-(1-hydroxyethyl)-7-oxo-1-azabicyclo[3.2.0]hept-2-ene-2-carboxylic acid;
3-(2-formimidoylaminoethylthiomethyl)-6-(1-hydroxyethyl)-7-oxo-1-azabicyclo[3.2.0]hept-2-ene-2-carboxylic acid;
3-(2-amino-1-methylethyl)thiomethyl-6-(1-hydroxyethyl)-7-oxo-1-azabicyclo[3.2.0]hept-2-ene-2-carboxylic acid;
3-(2-formimidoylamino-1-methylethyl)thiomethyl-6-(1-hydroxyethyl)-7-oxo-1-azabicyclo[3.2.0]hept-2-ene-2-carboxylic acid;
3-(3-aminopropylthiomethyl)-6-(1-hydroxyethyl)-7-oxo-1-azabicyclo[3.2.0]hept-2-ene-2-carboxylic acid;
3-(3-formimidoylaminopropylthiomethyl)-6-(1-hydroxyethyl)-7-oxo-1-azabicyclo[3.2.0]hept-2-ene-2-carboxylic acid;
3-(2-aminoethylsulphinylmethyl)-6-(1-hydroxyethyl)-7-oxo-1-azabicyclo[3.2.0]hept-2-ene-2-carboxylic acid;
3-(2-formimidoylaminoethylsulphinylmethyl)-6-(1-hydroxyethyl)-7-oxo-1-azabicyclo[3.2.0]hept-2-ene-2-carboxylic acid;
3-(2-amino-1-methylethyl)sulphinylmethyl-6-(1-hydroxyethyl)-7-oxo-1-azabicyclo[3.2.0]hept-2-ene-2-carboxylic acid;
3-(2-formimidoylamino-1-methylethyl)sulphinylmethyl-6-(1-hydroxyethyl)-7-oxo-1-azabicyclo[3.2.0]hept-2-ene-2-carboxylic acid;
3-(2-aminoethylsulphonylmethyl)-6-(1-hydroxyethyl)-7-oxo-1-azabicyclo[3.2.0]hept-2-ene-2-carboxylic acid;
3-(2-formimidoylaminoethylsulphonylmethyl)-6-(1-hydroxyethyl)-7-oxo-1-azabicyclo[3.2.0]hept-2-ene-2-carboxylic acid;
3-(2-amino-1-methylethyl)sulphonylmethyl-6-(1-hydroxyethyl)-7-oxo-1-azabicyclo[3.2.0]hept-2-ene-2-carboxylic acid;
3-(2-formimidoylamino-1-methylethyl)sulphonylmethyl-6-(1-hydroxyethyl)-7-oxo-1-azabicyclo[3.2.0]hept-2-ene-2-carboxylic acid;
pivaloyloxymethyl 3-(2-aminoethylthiomethyl)-6-(1-hydroxyethyl)-7-oxo-1-azabicyclo[3.2.0]hept-2-ene-2-carboxylate;
pivaloyloxymethyl 3-(2-formimidoylaminoethylthiomethyl)-6-(1-hydroxyethyl)-7-oxo-1-azabicyclo[3.2.0]hept-2-ene-2-carboxylate;
pivaloyloxymethyl 3-(2-amino-1-methylethyl)thiomethyl-6-(1-hydroxyethyl)-7-oxo-1-azabicyclo[3.2.0]hept-2-ene-2-carboxylate; and
pivaloyloxymethyl 3-(2-formimidoylamino-1-methylethyl)thiomethyl-6-(1-hydroxyethyl)-7-oxo-1-azabicyclo[3.2.0]hept-2-ene-2-carboxylate; and
pharmaceutically accepted salts of said carboxylic acids.

2. The compounds of claim 1 which are 3-(2-aminoethylthiomethyl)-6-(1-hydroxyethyl)-7-oxo-1-azabicyclo[3.2.0]hept-2-ene-2-carboxylic acid and pharmaceutically acceptable salts thereof.

3. The compound of claim 1 which is the pivaloyloxymethyl 3-(2-aminoethylthiomethyl)-6-(1-hydroxyethyl)-7-oxo-1-azabicyclo[3.2.0]hept-2-ene-2-carboxylate.

4. The compounds of claim 1 which are 3-(2-formimidoylaminoethylthiomethyl)-6-(1-hydroxyethyl)-7-oxo-1-azabicyclo[3.2.0]hept-2-ene-2-carboxylic acid and pharmaceutically acceptable salts thereof.

5. The compound of claim 1 which is the pivaloyloxymethyl 3-(2-formimidoylaminoethylthiomethyl)-6-(1-hydroxyethyl)-7-oxo-1-azabicyclo[3.2.0]hept-2-ene-2-carboxylate.

6. The compounds of claim 1 which are 3-(2-amino-1-methylethyl)thiomethyl-6-(1-hydroxyethyl)-7-oxo-1-azabicyclo[3.2.0]hept-2-ene-2-carboxylic acid and pharmaceutically acceptable salts thereof.

7. The compound of claim 1 which is the pivaloyloxymethyl 3-(2-amino-1-methylethyl)thiomethyl-6-(1-hydroxyethyl)-7-oxo-1-azabicyclo[3.2.0]hept-2-ene-2-carboxylate.

8. The compounds of claim 1 which are 3-(2-formimidoylamino-1-methylethyl)thiomethyl-6-(1-hydroxyethyl)-7-oxo-1-azabicyclo[3.2.0]hept-2-ene-2-carboxylic acid and pharmaceutically acceptable salts thereof.

9. The compound of claim 1, which is the pivaloyloxymethyl 3-(2-formimidoylamino-1-methylethyl)thiomethyl-6-(1-hydroxyethyl)-7-oxo-1-azabicyclo[3.2.0]hept-2-ene-2-carboxylate.

10. The compounds of any one of claims 1, 2, 3, 4, 5, 6, 7, 8, or 9 wherein said compounds are in the (5R, 6S) configuration.

11. The compounds of any one of claims 1, 2, 3, 4, 5, 6, 7, 8, or 9 wherein said compounds are in the (5R, 6R) configuration.

12. The compound of claim 1 which is (5R, 6S)-3-(2-aminoethylthiomethyl)-6-[1-(R)-hydroxyethyl]-7-oxo-1-azabicyclo[3.2.0]hept-2-ene-2-carboxylic acid.

13. A pharmaceutical composition comprising an antibiotically effective amount of at least one compound of any one of claims 1, 2, 3, 4, 5, 6, 7, 8, 9, or 12 together with a pharmaceutically acceptable carrier.

14. The composition of claim 13 wherein said antibiotic is selected from:
(5R, 6S)-3-(2-aminoethylthiomethyl)-6-[1-(R)-hydroxyethyl]-7-oxo-1-azabicyclo[3.2.0]hept-2-ene-2-carboxylic acid and pharmaceutically acceptable salts thereof.

* * * * *